US008420314B2

(12) United States Patent
Karlsen

(10) Patent No.: US 8,420,314 B2
(45) Date of Patent: *Apr. 16, 2013

(54) METHOD FOR DETECTING HUMAN PAPILLOMAVIRUS MRNA

(75) Inventor: Frank Karlsen, Klokkarstua (NO)

(73) Assignee: Norchip A/S, Klokkarstua (NO)

( * ) Notice: Subject to any disclaimer, the term of this patent is extended or adjusted under 35 U.S.C. 154(b) by 0 days.

This patent is subject to a terminal disclaimer.

(21) Appl. No.: 12/483,860

(22) Filed: Jun. 12, 2009

(65) Prior Publication Data

US 2009/0275044 A1    Nov. 5, 2009

Related U.S. Application Data

(63) Continuation of application No. 10/500,832, filed as application No. PCT/GB03/00034 on Jan. 7, 2003, now Pat. No. 7,553,623.

(30) Foreign Application Priority Data

Jan. 7, 2002  (GB) .................................. 0200239.2
Jun. 19, 2002 (GB) .................................. 0214124.0

(51) Int. Cl.
*C12Q 1/68* (2006.01)

(52) U.S. Cl.
USPC ........................................................ 435/6.1

(58) Field of Classification Search ........................ None
See application file for complete search history.

(56) References Cited

U.S. PATENT DOCUMENTS

| | | | |
|---|---|---|---|
| 5,474,796 A | 12/1995 | Brennan | |
| 5,506,105 A | 4/1996 | Haydock | |
| 5,580,970 A | 12/1996 | Hendricks et al. | |
| 5,639,871 A | 6/1997 | Bauer et al. | |
| 5,654,416 A | 8/1997 | Cummins et al. | |
| 5,750,334 A | 5/1998 | Cerutti et al. | |
| 6,027,891 A | 2/2000 | Von Knebel-Doberitz et al. | |
| 6,027,981 A | 2/2000 | Wu | |
| 2001/0053519 A1 | 12/2001 | Fodor et al. | |
| 2004/0214302 A1 | 10/2004 | Anthony et al. | |
| 2005/0118568 A1 | 6/2005 | Karlsen | |
| 2005/0244813 A1 | 11/2005 | Karlsen | |
| 2007/0281295 A1 | 12/2007 | Karlsen | |
| 2007/0292841 A1 | 12/2007 | Karlsen | |

FOREIGN PATENT DOCUMENTS

| | | |
|---|---|---|
| DE | 4431174 A1 | 3/1996 |
| EP | 0 243 221 A1 | 10/1987 |
| EP | 0 402 132 A2 | 12/1990 |
| EP | 0 662 518 A2 | 7/1995 |
| EP | 0 774 518 A2 | 5/1997 |
| WO | WO 90/02821 A1 | 3/1990 |
| WO | WO 91/08312 A2 | 6/1991 |
| WO | WO 94/26934 A2 | 11/1994 |
| WO | WO 99/29890 A2 | 6/1999 |
| WO | WO 9929890 A2 * | 6/1999 |
| WO | WO 00/00638 A2 | 1/2000 |
| WO | WO 01/73135 A2 | 11/2001 |
| WO | WO 02/08460 A2 | 1/2002 |
| WO | WO 03/057914 A2 | 7/2003 |
| WO | WO 03/057927 A2 | 7/2003 |

OTHER PUBLICATIONS

Leone et al. ("Molecular beacon probes combined with amplification by NASBA enable homogeneous, real-time detection of RNA" Nucleic Acids Res. May 1, 1998;26(9):2150-5).*

[Author Unknown] http://www.biotech.ist.unige.it/cldb/c14900.html; web page regarding SiHa cells, May 27, 2004.

In Re Deuel 34 USPQ 2d 1210 (Fed. Cir. 1995).

Anderson et al., Human papillomavirus and cervical cancer. Clin Microbiol Newslett. Aug. 1, 2002;24(15):113.

Arbeit, J. M. et al., Neuroepithelial Carcinomas in Mice Transgenic with Human Papillomavirus Type 16 E6/E7 ORFs, American Journal of Pathology 1993; 142(4):1187-1197.

Bosch et al., Papillomavirus research update: highlights of the Barcelona HPV 2000 international papillomavirus conference. J Clin Pathol. Mar. 2001;54(3):163-75.

Bosch, F.X. et al., Prevalence of Human papillomavirus in cervical cancer: a worldwide perspective. Journal of the National Cancer Institute Jun. 7, 1995; 87(11):796-802.

Bosch, F. X. et al., The causal relation between human papillomavirus and cervical cancer, J. Clin. Pathol. 2002; 55:244-265.

Buck et al. (1999) Design strategies and performance of custom DNA sequencing primers. Biotechniques. vol. 27, pp. 528-536.

Clifford et al., Human papillomavirus types in invasive cervical cancer worldwide: a meta-analysis. Br J Cancer. Jan. 13, 2003;88(1):63-73.

Cornelissen, M.T. et al., Uniformity of the splicing pattern of the E6/E7 transcripts in human papillomavirus type 16-transformed human fibroblasts, human cervical premalignant lesions and carcinomas. Journal of General Virology, Society for General Microbiology, Reading, GB, May 1, 1990; 71(No. Part 5):1243-1249.

Coutlee, F. et al., Detection of transcripts of human papillomaviruses 16 and 18 in Cancer-derived cell lines and cervical biopsies by enzyme immunoassay for DNA-RNA hybrids following solution hybridization. J. Clin. Micro. 1991; 29:968-974.

Cuschieri et al., Human papillomavirus type specific DNA and RNA persistence—implications for cervical disease progression and monitoring. J Med Virol. May 2004;73(1):65-70.

(Continued)

*Primary Examiner* — Christopher M. Babic
(74) *Attorney, Agent, or Firm* — Wolf, Greenfield & Sacks, P.C.

(57) ABSTRACT

An in vitro method is provided for screening human female subjects to assess their risk of developing cervical carcinoma which comprises screening the subject for expression of mRNA transcripts from the E6 and optionally the L1 gene of human papillomavirus, wherein subjects positive for expression of L1 and/or E6 mRNA are scored as being at risk of developing cervical carcinoma. Kits for carrying out such methods are also provided.

15 Claims, 6 Drawing Sheets

OTHER PUBLICATIONS

Figure 1A:
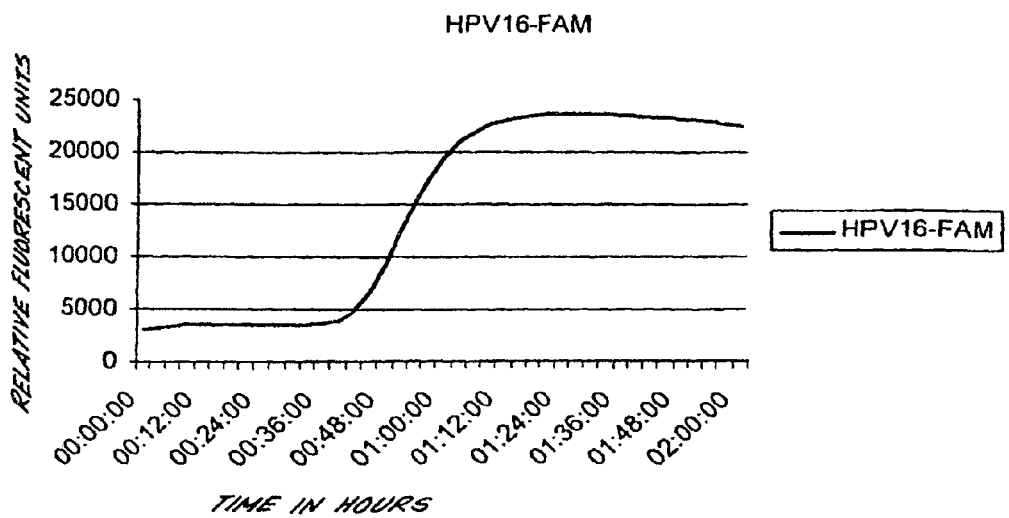

Database, HPV sequence Database, 'Online! Los Alamos National Laboratory; Sep. 1997, Los Alomos National Laboratory; "Human papilloma viruses 1997 compendium," pp. E6-10-E6-24.

Doeberitz, M. New molecular tools for efficient screening of cervical cancer. 2001; 17:123-128.

Duensing et al., Mechanisms of genomic instability in human cancer: insights from studies with human papillomavirus oncoproteins. Int J Cancer. Mar. 20, 2004;109(2):157-62.

Iwasawa, A. et al. Human papillomavirus DNA in uterine cervix squamous cell carcinoma and adenocarcinoma detected by polymerase chain reaction. American Cancer Society 1996; 77(11):2275-2279.

Jeon et al., Integration of human papillomavirus type 16 into the human genome correlates with a selective growth advantage of cells. J Virol. May 1995;69(5):2989-97.

Jeon et al., Integration of human papillomavirus type 16 DNA into the human genome leads to increased stability of E6 and E7 mRNAs: Implications for cervical carcinogenesis. Proceedings of the National Academy of Sciences of the U.S.; 1995; 92(5):1654-1658.

Karlsen et al., Use of multiple PCR primer sets for optimal detection of human papillomavirus. J Clin Microbiol. Sep. 1996;34(9):2095-100.

Kado, S. et al., Detection of human papillomavirus in cervical neoplasias using multiple sets of generic polymerase chain reaction primers. Gynecologic Oncology Apr. 2001; 81(1):47-52.

Kievits et al. (1991) NASBA isothermal enzymatic in vitro nucleic acid amplification optimized for the diagnosis of HIV-1 infection. Journal of Virological Methods. vol. 35, pp. 273-286.

Klaes et al., Detection of high-risk cervical intraepithelial neoplasia and cervical cancer by amplification of transcripts derived from integrated papillomavirus oncogenes. Cancer Res. Dec. 15, 1999;59(24):6132-6.

Kraus et al., Human papillomavirus oncogenic expression in the dysplastic portio; an investigation of biopsies from 190 cervical cones. Br J Cancer. Apr. 5, 2004;90(7):1407-13.

Kraus et al., Presence of E6 and E7 mRNA from human papillomavirus types 16, 18, 31, 33, and 45 in the majority of cervical carcinomas. J Clin Microbiol. Apr. 2006;44(4):1310-7.

Lanham, S. et al., NPV detection and measurement of HPV-16, telomerase, and survivin transcripts in colposcopy clinic patients. J. Clin. Pathol. 2001; 54:304-308.

Leone et al., Molecular beacon probes combined with amplification by NASBA enable homogeneous, real-time of RNA. Nucleic Acids Research 1998; 26(9):2150-2155.

Lie et al., DNA versus RNA based methods for HPV testing in Norway. Evaluation of Hybrid Capture II and PreTesct HPV-Proofer, a validation study. 21$^{st}$ International Papillomavirus Conference Feb. 20-26, Mexico City, Mexico.

McNicol, P. et al., Expression of human papillomavirus type 16 E6-E7 open reading frame varies, quantitatively in biopsy tissue from different grades of cervical intraepithelial neoplasia. Journal of Clinical Microbiology 1995; 33(5):1169-1173.

Molden et al., Comparison of human papillomavirus messenger RNA and DNA detection: a cross-sectional study of 4,136 women >30 years of age with a 2-year follow-up of high-grade squamous intraepithelial lesion. Cancer Epidemiol Biomarkers Prey. Feb. 2005;14(2):367-72.

Molden et al., Human papillomavirus E6/E7 mRNA expression in women younger than 30 years of age. Gynecol Oncol. Jan. 2006;100(1):95-100. Epub Sep. 8, 2005.

Munoz et al., Against which human papillomavirus types shall we vaccinate and screen? The international perspective. Int J Cancer. Aug. 20, 2004;111(2):278-85.

Muñoz, N. Human papillomavirus and cancer: the epidemiological evidence, Journal of Clinical Virology 2000; 19:1-5.

Pim et al., Alternatively spliced HPV-18 E6* protein inhibits E6 mediated degradation of p53 and suppresses transformed cell growth. Oncogene. Jul. 17, 1997;15(3):257-64.

Schneider-Gadicke et al., Different human cervical carcinoma cell lines show similar transcription patterns of human papillomavirus type 18 early genes. EMBO J. Sep. 1986;5(9):2285-92.

Schneider, A. et al., Importance of Human Papillomavirus Detection in Screening, 2001; Deutsches Arzteblatt 2001; Jg. 98, 39:2517-2521, Abstract.

Simpkins et al. (Jan. 2000) An RNA transcription-based amplification technique (NASBA) for the detection of viable *Salmonella enterica*. Letters in Applied Microbiology. vol. 30, pp. 75-79.

Soltar et al., Detection of high-risk human papillomavirus E6 and E7 oncogene transcripts in cervical scrapes by nested RT-polymerase chain reaction. J Med Virol. Sep. 2004;74(1):107-16.

Smits, H.L. et al., Application of the NASBA nucleic acid amplification method for the detection of human papillomavirus type 16 E6-E7 transcripts. Journal of Virological Methods, Amsterdam, NL. 1995; 54(1):75-81.

Tyagi et al. (1996) Molecular Beacons: Probes that Fluoresce upon Hybridization. Nature Biotechnology. 14: 303-308.

Van Den Brule et al., Difference in prevalence of human papillomavirus genotypes in cytomorphologically normal cervical smears is associated with a history of cervical intraepithelial neoplasia. Int J Cancer. May 30, 1991;48(3):404-8.

Walboomers, J.M.M. et al. Human papillomavirus is a necessary cause of invasive cervical cancer worldwide. Journal of Pathology, J. Pathol. 1999; 189:12-19.

Werness, B. A. et al., Association of Human Papillomavirus Types 16 and 18 E6 Proteins with p53, Science 1990; 248:76-79.

Wu Shuenn-Jue L. et al., Detection of dengue viral RNA using a nucleic acid sequence-based amplification assay. Journal of Clinical Microbiology Aug. 2001; 39(8): 2794-2798.

Yates et al. (Oct. 2001) Quantitative detection of Hepatitis B Virus DNA by real-time nucleic acid sequence-based amplification with molecular beacon detection. Journal of Clinical Microbiology. vol. 39, pp. 3656-3665.

NCBI (Accession No. X74479; Aug. 22, 1993).

NCBI (Accession No. X74481; Aug. 22, 1993).

NCBI (Accession No. D90400; Apr. 17, 1992).

Stratagene ("Gene Chracterization Kits" 1988).

Böhm et al., The predominant mRNA class in HPV16-infected genital neoplasias does not encode the E6 or the E7 protein. Int J Cancer. Nov. 11, 1993;55(5):791-8.

Falcinelli et al., Detection of the human papilloma virus type 16 mRNA-transcripts in cytological abnormal scrapings. J Med Virol. Jun. 1992;37(2):93-8.

Forslund et al., HPV 16 DNA and mRNA in cervical brush samples quantified by PCR and microwell hybridization. J Virol Methods. Dec. 1997;69(1-2):209-22.

Nakagawa et al., Ubiquitous presence of E6 and E7 transcripts in human papillomavirus—positive cervical carcinomas regardless of its type. J Med Virol. Apr. 2000; 62:251-56.

Sasagawa et al., Cervical/vaginal dysplasias of transgenic mice harbouring human papillomavirus type 16 E6-E7genes. J Gen Virol. Nov. 1994;75 ( Pt 11):3057-65.

Sedman et al., The full-length E6 protein of human papillomavirus type 16 has transforming and trans-activating activities and cooperates with E7 to immortalize keratinocytes in culture. J Virol. Sep. 1991;65(9):4860-6.

Shally et al., The E6 variant proteins E6I-E6IV of human papillomavirus 16: expression in cell free systems and bacteria and study of their interaction with p53. Virus Res. Jun. 1996;42(1-2):81-96.

Sherman et al., Expression and splicing patterns of human papillomavirus type-16 mRNAs in pre-cancerous lesions and carcinomas of the cervix, in human keratinocytes immortalized by HPV 16, and in cell lines established from cervical cancers. Int J Cancer. Feb. 1, 1992;50(3):356-64.

Shirasawa et al., Quantitative detection of spliced E6-E7 transcripts of human papillomavirus type 16 in cervical premalignant lesions. Virology. Oct. 1991;184(2):795-8.

* cited by examiner

METHOD FOR DETECTING HUMAN PAPILLOMAVIRUS MRNA

RELATED APPLICATIONS

This application is a continuation of U.S. application Ser. No. 10/500,832, filed Jan. 6, 2005 and now U.S. Pat. No. 7,553,623, which is a national stage filing under 35 U.S.C. §371 of PCT International application PCT/GB2003/000034, filed Jan. 7, 2003, which was published under PCT Article 21(2) in English.

FIELD OF THE INVENTION

The present invention relates to in vitro methods of screening human subjects in order to assess their risk of developing cervical carcinoma.

BACKGROUND TO THE INVENTION

Cervical carcinoma is one of the most common malignant diseases world-wide and is one of the leading causes of morbidity and mortality among women (Parkin D M, Pisani P, Ferlay J (1993) Int J Cancer 54: 594-606; Pisani P, Parkin D M, Ferlay J (1993) Int J Cancer 55: 891-903). 15,700 new cases of invasive cervical cancer were predicted in the United States in 1996, and the annual world-wide incidence is estimated to be 450,000 by the World Health Organization (1990). The annual incidence rate differs in different parts of the world, ranging from 7.6 per 100,000 in western Asia to 46.8 per 100,000 in southern Africa (Parkin et al., 1993 ibid).

The current conception of cervical carcinoma is that it is a multistage disease, often developing over a period of 10-25 years. Invasive squamous-cell carcinoma of the cervix is represented by penetration through the basal lamina and invading the stroma or epithelial lamina propria. The clinical course of cervical carcinoma shows considerable variation. Prognosis has been related to clinical stage, lymph node involvement, primary tumour mass, histology type, depth of invasion and lymphatic permeation (Delgado G, et al., (1990) Gynecol Oncol 38: 352-357). Some patients with less favourable tumour characteristics have a relatively good outcome, while others suffer a fatal outcome of an initially limited disease. This shows a clear need for additional markers to further characterise newly diagnosed cervical carcinomas, in order to administer risk-adapted therapy (Ikenberg H, et al., Int. J. Cancer 59:322-6. 1994).

The epidemiology of cervical cancer has shown strong association with religious, marital and sexual patterns. Almost 100 case-control studies have examined the relationship between HPV and cervical neoplasia and almost all have found positive associations (IARC monographs, 1995). The association is strong, consistent and specific to a limited number of viral types (Munoz N, Bosch F X (1992) HPV and cervical neoplasia: review of case-control and cohort studies. IARC Sci Publ 251-261). Among the most informative studies, strong associations with HPV 16 DNA have been observed with remarkable consistency for invasive cancer and high-grade CIN lesions, ruling out the possibility that this association can be explained by chance, bias or confounding (IARC monographs, 1995). Indirect evidence suggested that HPV DNA detected in cancer cells is a good marker for the role of HPV infection earlier in the carcinogenesis. Dose-response relationship has been reported between increasing viral load and risk of cervical carcinoma (Munoz and Bosch, 1992 ibid). In some larger series up to 100% of the tumours were positive for HPV but the existence of virus-negative cervical carcinomas is still debatable (Meijer C J, et al., (1992) Detection of human papillomavirus in cervical scrapes by the polymerase chain reaction in relation to cytology: possible implications for cervical cancer screening. IARC Sci Publ 271-281; Das B C, et al., (1993) Cancer 72: 147-153).

The most frequent HPV types found in squamous-cell cervical carcinomas are HPV 16 (41%-86%) and 18 (2%-22%). In addition HPV 31, 33, 35, 39, 45, 51, 52, 54, 56, 58, 59, 61, 66 and 68 are also found (IARC, monographs, 1995). In the HPV2000 International conference in Barcelona HPV 16, 18, 31 and 45 were defined as high risk, while HPV 33, 35, 39, 51, 52, 56, 58, 59, 68 were defined as intermediate risk (Keerti V. Shah. P71). The 13 high risk plus intermediate risk HPVs are together often referred to as cancer-associated HPV types.

A number of studies have explored the potential role of HPV testing in cervical screening (see Cuzick et al. A systematic review of the role of human papillomavirus testing within a cervical screening programme. Health Technol Assess 3:14. 1999).

Reid et al., (Reid R, et al., (1991) Am J Obstet Gynecol 164: 1461-1469) where the first to demonstrate a role for HPV testing in a screening context. This study was carried out on high-risk women from sexually transmitted disease clinics and specialist gynaecologists, and used a sensitive (low stringency) Southern blot hybridisation for HPV detection. A total of 1012 women were enrolled, and cervicography was also considered as a possible adjunct to cytology. Twenty-three CIN II/III lesions were found altogether, but only 12 were detected by cytology (sensitivity 52%, specificity 92%). HPV testing found 16 high-grade lesions.

Bauer et al. (Bauer H M, et al., (1991) JAMA 265: 472-477) report an early PCR-based study using MY09/11 primers (Manos M, et al., (1990) Lancet 335: 734) in young women attending for routine smears (college students). They found a positive rate of 46% in 467 women, which was much higher than for dot blot assay (11%).

In a study using PCR with GP5/6 primers (Van Den Brule A J, et al., (1990) J Clin Microbiol 28: 2739-2743) van der Brule et al. (Van Den Brule A J, et al., (1991) Int J Cancer 48: 404-408) showed a very strong correlation of HPV positivity with cervical neoplasia as assessed by cytology. In older women (aged 35-55 years) with negative cytology the HPV positivity rate was only 3.5%, and this was reduced to 1.5% if only types 16, 18, 31 and 33 were considered, while women with histological carcinoma in situ were all HPV-positive, and 90% had one of the four above types. Women with less severe cytological abnormalities had lower HPV positivity rates in a graded way, showing a clear trend.

Roda Housman et al. (Roda Housman A M, et al., (1994) Int J Cancer 56: 802-806) expanded these observations by looking at a further 1373 women with abnormal smears. This study also confirmed increasing positivity rate with increasing severity of smear results. They also noted that the level of HPV heterogeneity decreased from 22 types for low-grade smears to ten "high-risk" types for high grade smears. This paper did not include any cytologically negative women, nor was cytological disease confirmed histologically.

Cuzick et al. (Cuzick J, et al., (1992) Lancet 340: 112-113; Cuzick J, et al., (1994) Br J Cancer 69: 167-171) were the first to report that HPV testing provided useful information for the triage of cytological abnormalities detected during random screening. In a study of 133 women, referral for colposcopy they found a positive predictive value of 42%, which was similar to that for moderate dyskaryosis. The results were most striking for HPV 16, where 39 of 42 HPV 16 positive women were found to have high-grade CIN on biopsy. This study pointed out the importance of assessing viral load and only considered high levels of high-risk types as positive.

Cox et al. (Cox J T, et al., (1995) Am J Obstet Gynecol 172: 946-954) demonstrated a role for HPV testing using the Hybrid Capture™ system (DIGENE Corporation, Gaithersburg, Md., USA) for triaging women with borderline smears. This test was performed on 217 such women from a college referral service, and a sensitivity of 93% was found for CINII/III compared with 73% for repeat cytology. High viral load was found to further improve performance by reducing false positives. When 5 RLU was taken as a cut-off, a PPV of approximately 24% was found with no loss of sensitivity.

Cuzick et al. (Cuzick J, et al., (1995) Lancet 345: 1533-1536) evaluated HPV testing in a primary screening context in 1985 women attending for routine screening at a family planning clinic. Sensitivity using type-specific PCR for the four common HPV types (75%) exceeded that of cytology (46%), and the PPV for a positive HPV test (42%) was similar to that for moderate dyskaryosis (43%).

WO 91/08312 describes methods for determining the prognosis of individuals infected with HPV which comprise measuring the level of HPV activity by detecting transcripts of all or a portion of the E6 and/or E7 HPV genes in a sample and comparing the measurements of HPV activity with a previously established relationship between activity and risk of progression to serious cervical dysplasia or carcinoma.

WO 99/29890 describes methods for the assessment of HPV infection based on the measurement and analysis of gene expression levels. In particular, WO 99/29890 describes methods which are based on measuring the levels of expression of two or more HPV genes (e.g. HPV E6, E7, L1 and E2) and then comparing the ratio of expression of combinations of these genes to provide an indication of the stage of HPV-based disease in a patient.

The present inventors have determined that it is possible to make a clinically useful assessment of HPV-associated disease based only on a simple positive/negative determination of expression of HPV L1 and E6 mRNA transcripts, with no requirement for accurate quantitative measurements of expression levels or for determination of differences in the levels of expression of the two transcripts. This method is technically simple and, in a preferred embodiment, is amenable to automation in a mid-to-high throughput format. Furthermore, on the basis of results obtained using the method of the invention the inventors have defined a novel scheme for classification of patients on the basis of risk of developing cervical carcinoma which is related to disease-relevant molecular changes in the pattern of HPV gene expression and is independent of CIN classification.

Therefore, in a first aspect the invention provides an in vitro method of screening human subjects to assess their risk of developing cervical carcinoma which comprises screening for expression of mRNA transcripts from the L1 gene and the E6 gene of human papillomavirus, wherein subjects positive for expression of L1 and/or full length E6 mRNA are scored as being at risk of developing cervical carcinoma.

A positive screening result in the method of the invention is indicated by positive expression of L1 mRNA and/or E6 mRNA in cells of the cervix. Positive expression of either one of these mRNAs or both mRNAs is taken as an indication that the subject is "at risk" for development of cervical carcinoma. Women who express E6 mRNA are at high risk of developing cell changes because oncogenic E6 and E7 bind to cell cycle regulatory proteins and act as a switch for cell proliferation. Clear expression of E6 mRNA provides a direct indication of cell changes in the cervix. Expression of L1 mRNA, with or without expression of E6 mRNA is also indicative of the presence of an active HPV.

In the wider context of cervical screening, women identified as positive for L1 and/or E6 mRNA expression may be selected for further investigation, for example using cytology. Thus, at one level the method of the invention may provide a technical simple means of pre-screening a population of women in order to identify HPV-positive subjects who may be selected for further investigation.

In a specific embodiment, the method of the invention may be used to classify subjects into four different classes of risk for developing cervical carcinoma on the basis of positive/negative scoring of expression of L1 and E6 mRNA.

Accordingly, in a further aspect the invention provides an in vitro method of screening human subjects to assess their risk of developing cervical carcinoma which comprises screening the subject for expression of mRNA transcripts of the L1 gene of HPV and mRNA transcripts of the E6 gene of HPV, and sorting the subject into one of four categories of risk for development of cervical carcinoma based on expression of L1 and/or E6 mRNA according to the following classification:

Risk category 1: subjects negative for expression of L1 mRNA but positive for expression of E6 mRNA from at least one of HPV types 16, 18, 31, 33, 35, 39, 45, 52, 56, 58, 59, 66 or 68. Those individuals positive for expression of E6 mRNA from at least one of HPV types 16, 18, 31 or 33 are scored as being at higher risk, for example in comparison to individuals negative for these types but positive for expression of E6 mRNA from at least one of HPV types 35, 39, 45, 52, 56, 58, 59, 66 or 68.

Risk category 2: subjects positive for expression of L1 mRNA and positive for expression of E6 mRNA from at least one of HPV types 16, 18, 31, 33, 35, 39, 45, 52, 56, 58, 59, 66 or 68. Those individuals positive for expression of E6 mRNA from at least one of HPV types 16, 18, 31 or 33 are scored as being at higher risk, for example in comparison to individuals negative for these types but positive for expression of E6 mRNA from at least one of HPV types 35, 39, 45, 52, 56, 58, 59, 66 or 68.

Risk category 3: subjects positive for expression of L1 mRNA but negative for expression of E6 mRNA from the cancer-associated HPV types, (e.g. negative for expression of E6 mRNA from HPV types 16, 18, 31, 33, 35, 39, 45, 52, 56, 58, 59, 66 and 68).

Risk category 4: subjects negative for expression of L1 mRNA and negative for expression of E6 mRNA.

In a preferred embodiment, positive expression is indicated by the presence of more than 50 copies of the transcript per ml (or total volume of the sample) and negative expression is indicated by the presence of less than 1 copy of the transcript per ml (or total volume of the sample).

The above classification is based on molecular events which are relevant to risk of developing cervical carcinoma and is independent of the CIN status of the subjects. Thus, this method of classification may provide an alternative to the use of cytology in the routine screening of women to identify those at potential risk of developing cervical carcinoma. The method may also be used as an adjunct to cytology, for example as a confirmatory test to confirm a risk assessment made on the basis of cytology.

Women positive for expression of high risk E6 mRNA from one of HPV types 16, 18, 31 or 33 but negative for expression of L1 are in the highest level of risk of developing severe cell changes and cell abnormalities. This is due to the fact that a negative result for L1 mRNA expression is directly indicative of integrated HPV, and therefore a higher probability of high and constant expression of E6 and E7. Integration of a virus in the human genome has also a direct impact on the stability of the cells. Integration of HPV also reduces the possibility of regression of cell changes.

Women positive for expression of E6 mRNA from one of HPV types 16, 18, 31 or 33 and positive for expression of L1 mRNA have a "high risk" HPV expression and it is still possible that the HPV has been integrated. However, the risk of these women is not classed as high as those who are L1 negative and E6 positive, since there is a reasonable probability that they do not have integrated HPV.

Women negative for expression of E6 mRNA from HPV types 16, 18, 31 or 33 but positive for expression of E6 mRNA from another HPV type, e.g. 35, 39, 45, 52, 56, 58, 59, 66 and 68, are still considered "at risk" and may therefore be placed in risk categories 1 or 2 (as defined above) depending on whether they are positive or negative for expression of L1 mRNA.

Women positive for L1 mRNA but negative for E6 mRNA are scored as being at moderate risk. There may be high-risk HPV types in the sample and L1 expression is indicative of lytic activity. There may also be integrated HPV types but only with viruses that are rare. However, detection of lytic activity may show that the cell may soon develop some changes.

In the wider context of cervical screening the method of the invention may be used to classify women according to risk of developing cervical carcinoma and therefore provide a basis for decisions concerning treatment and/or further screening. By way of example: women in risk category 1, particularly those who exhibit positive expression of E6 mRNA from at least one of HPV types 16, 18, 31 or 33, might be identified as requiring "immediate action", meaning conisation or colposcopy, including a biopsy and histology.

Women in risk category 2, as defined above, might be scored as requiring immediate attention, meaning colposcopy alone or colposcopy including a biopsy and histology.

Women in risk category 3, as defined above, might be scored as requiring immediate re-test, meaning recall for a further test for HPV expression immediately or after a relatively short interval, e.g. six months.

Women in risk category 4, as defined above, might be returned to the screening program, to be re-tested for HPV expression at a later date.

In a further embodiment the invention provides an in vitro method of screening human subjects for the presence of integrated HPV or a modified episomal HPV genome, which method comprises screening the subject for expression of mRNA transcripts from the L1 gene and the E6 gene of human papillomavirus, wherein subjects negative for expression of L1 mRNA but positive for expression of E6 mRNA are scored as carrying integrated HPV.

The term "integrated HPV" refers to an HPV genome which is integrated into the human genome.

The term "modified episomal HPV genome" is taken to mean an HPV genome which is retained within a cell of the human subject as an episome, i.e. not integrated into the human genome, and which carries a modification as compared to the equivalent wild-type HPV genome, which modification leads to constitutive or persistent expression of transcripts of the E6 and/or E7 genes. The "modification" will typically be a deletion, a multimerisation or concatermerisation of the episome, a re-arrangement of the episome etc affecting the regulation of E6/E7 expression.

As aforesaid, the presence of integrated HPV or a modified episomal HPV genome is indicated by a negative result for L1 mRNA expression, together with a positive result for expression of E6 mRNA in cells of the cervix. Therefore, the ability to predict the presence of integrated HPV or a modified episomal HPV genome in this assay is critically dependent on the ability to score a negative result for L1 mRNA expression. This requires a detection technique which has maximal sensitivity, yet produces minimal false-negative results. In a preferred embodiment this is achieved by using a sensitive amplification and real-time detection technique to screen for the presence or absence of L1 mRNA. The most preferred technique is real-time NASBA amplification using molecular beacons probes, as described by Leone et al., Nucleic Acids Research., 1998, Vol 26, 2150-2155. Due to the sensitivity of this technique the occurrence of false-negative results is minimised and a result of "negative L1 expression" can be scored with greater confidence.

In a further embodiment, a method of screening human subjects for the presence of integrated HPV or a modified episomal HPV genome may be based on screening for expression of E6 mRNA alone. Thus, the invention relates to an in vitro method of screening human subjects for the presence of integrated HPV or a modified episomal HPV genome, which method comprises screening the subject for expression of mRNA transcripts from the E6 gene of human papillomavirus, wherein subjects positive for expression of E6 mRNA are scored as carrying integrated HPV or a modified episomal HPV genome.

Moreover, individuals may be sorted into one of two categories of risk for development of cervical carcinoma based on an "on/off" determination of expression of E6 mRNA alone. Therefore, the invention provides an in vitro method of screening human subjects to assess their risk of developing cervical carcinoma, which method comprises screening the subject for expression of mRNA transcripts of the E6 gene of HPV and sorting the subject into one of two categories of risk for development of cervical carcinoma based on expression of E6 mRNA, wherein individuals positive for expression of E6 mRNA are scored as carrying integrated HPV or a modified episomal HPV genome and are therefore classified as "high risk" for development of cervical carcinoma, whereas individuals negative for expression of E6 mRNA are scored as not carrying integrated HPV or a modified episomal HPV genome and are therefore classified as "no detectable risk" for development of cervical carcinoma.

Subjects are sorted into one of two categories of risk for development of cervical carcinoma based on an "on/off" determination of expression of E6 mRNA in cells of the cervix. Individuals positive for expression of E6 mRNA are scored as carrying integrated HPV or a modified episomal HPV genome and are therefore classified "high risk" for development of cervical carcinoma, whereas individuals negative for expression of E6 mRNA are scored as not carrying integrated HPV a modified episomal HPV genome and are therefore classified as "no detectable risk" for development of cervical carcinoma.

In the context of cervical screening classification of subjects into the two groups having "high risk" or "no detectable risk" for development of cervical carcinoma provides a basis for decisions concerning treatment and/or further screening. For example subjects in the high risk category may be scored as requiring immediate further analysis, e.g. by histological colposcopy, whilst those in the no detectable risk category may be referred back to the screening program at three or five year intervals.

These methods are particularly useful for assessing risk of developing carcinoma in subjects known to be infected with HPV, e.g. those testing positive for HPV DNA, or subjects who have previously manifested a cervical abnormality via cytology or pap smear. Subjects placed in the "no detectable risk" category on the basis of E6 mRNA expression may have HPV DNA present but the negative result for E6 expression indicates that HPV is unrelated to oncogene activity at the time of testing.

The presence of integrated HPV or a modified episomal HPV genome, as indicated by a positive result for E6 mRNA expression, is itself indicative that the subject has abnormal cell changes in the cervix. Therefore, the invention also relates to an in vitro method of identifying human subjects having abnormal cell changes in the cervix, which method comprises screening the subject for expression of mRNA transcripts of the E6 gene of HPV, wherein individuals positive for expression of E6 mRNA are identified as having abnormal cell changes in the cervix.

The term "abnormal cell changes in the cervix" encompasses cell changes which are characteristic of more severe disease than low-grade cervical lesions or low squamous intraepithelial lesions, includes cell changes which are characteristic of disease of equal or greater severity than high-grade CIN (defined as a neoplastic expansion of transformed cells), CIN (cervical intraepithelial neoplasia) III, or high squamous intraepithelial neoplasia (HSIL), including lesions with multiploid DNA profile and "malignant" CIN lesions with increased mean DNA-index values, high percentage of DNA-aneuploidy and 2.5c Exceeding Rates (Hanselaar et al., 1992, Anal Cell Pathol., 4:315-324; Rihet et al., 1996, J. Clin Pathol 49:892-896; and McDermott et al., 1997, Br. J. Obstet. Gynaecol. 104:623-625).

Cervical Intraepithelial Neoplasia (abbreviated "CIN"), also called Cervical Dysplasia, is a cervical condition caused Human Papilloma Virus. CIN is classified as I, II or III depending on its severity. It is considered a pre-cancerous abnormality, but not an actual cancer. The mildest form, CIN I, usually goes away on its own, although rarely it can progress to cancer. The more severe forms, CIN II and CIN III, most often stay the same or get worse with time. They can become a cancer, but almost never do if treated adequately.

HPV has been identified as a causative agent in development of cellular changes in the cervix, which may lead to the development of cervical carcinoma. These cellular changes are associated with constitutive or persistent expression of E6/E7 proteins from the HPV viral genome. Thus, it is possible to conclude that subjects in which expression of E6 mRNA can be detected, particularly those subjects who exhibit persistent E6 expression when assessed over a period of time, already manifest cellular changes in the cervix. These changes may have taken place in only a very few cells of the cervix, and may not be detectable by conventional cytology. Nevertheless, with the use of sensitive, specific and accurate methods for detection of E6 mRNA it is possible to identify those subjects who already exhibit cellular changes in the cervix at a much earlier stage than would be possible using conventional cytological screening. This will allow earlier intervention with treatments aimed at preventing the development of cervical carcinoma.

As a result of HPV integration into the human genome or as a result of the "modification" in a modified episomal HPV genome, normal control of the viral E6/E7 oncogene transcription is lost (Durst et al., 1985, J Gen Virol, 66(Pt 7): 1515-1522; Pater and Pater, 1985 Virology 145:313-318; Schwarz et al., 1985, Nature 314: 111-114; Park et al., 1997, ibid). In contrast, in premalignant lesions and HPV-infected normal epithelium papillomaviruses predominate in "unmodified" episomal forms, hence oncogene (E6/E7) transcription may be absent or efficiently down-regulated (Johnson et al., 1990, J Gen Virol, 71(Pt 7): 1473-1479; Falcinelli et al., 1993, J Med Virol, 40: 261-265). Integration of human papillomavirus type 16 DNA into the human genome is observed to lead to a more unstable cell activity/genome, and increased stability of E6 and E7 mRNAs (Jeon and Lambert, 1995, Proc Natl Acad Sci USA 92: 1654-1658). Thus HPV integration, typically found in cervical cancers but only infrequently found in CIN lesions (Carmody et al., 1996, Mol Cell Probes, 10: 107-116), appears to be an important event in cervical carcinogenesis.

The present methods detect E6/E7 viral mRNA expression in the cervix instead of DNA. E6/E7 viral expression in cervical cells is a much more accurate assessment of the risk of developing cancer than simply showing that the HPV virus is present. Furthermore, the detection of HPV oncogene transcripts may be a more sensitive indicator of the direct involvement of viral oncogenes in carcinogenesis (Rose et al., 1994, Gynecol Oncol, 52: 212-217; Rose et al., 1995, Gynecol Oncol, 56: 239-244). Detection of E6/E7 transcripts by amplification and detection is a useful diagnostic tool for risk evaluations regarding the development of CIN and its progression to cervical cancer, especially in high-risk HPV type-infected patients with ASCUS and CIN I (Sotlar et al., 1998, Gynecol Oncol, 69: 114-121; Selinka et al., 1998, Lab Invest, 78: 9-18).

The expression of E6/E7 transcripts of HPV-16/18 is uniformly correlated with the physical status of HPV DNAs (Park et al., 1997, Gynecol Oncol, Vol: 65(1), 121-9). In most cervical carcinoma cells the E6 and E7 genes of specific human papillomaviruses are transcribed from viral sequences integrated into host cell chromosomes (von Kleben Doeberitz et al., 1991, Proc Natl Acad Sci USA. Vol: 88(4), 1411-5). Viral load and integration has been evaluated in a large series of CIN lesions (Pietsaro et al., 2002, J Clin Microbiol, Vol: 40(3), 886-91). Only one sample contained exclusively episomal HPV16 DNA, and this lesion regressed spontaneously. Seventeen of 37 invasive cervical carcinoma samples were identified previously as containing the completely integrated HPV16 genome by using PCR covering the entire E1/E2 gene, and this was confirmed by rliPCR in 16 cases. One case, however, showed a low level of episomal deoxyribonucleic acid in addition to the predominant integrated form. Of the remaining 20 carcinoma samples showing episomal forms in the previous analysis, 14 were found to contain integrated forms using rliPCR, and four contained multimeric (modified) episomal forms. Thus, in total, 31 of 37 of the carcinomas (84%) showed integrated HPV16 genome, while absence of integration could not be detected. (Kalantari et al, 2001, Diagn Mol Pathol, Vol: 10(1), 46-54).

There have been virtually no observations that cervical carcinoma cells exist without integrated HPV or modified episomal HPV DNA (Kalantari et al. 2001; Pietsaro et al., 2002, ibid). It has further been shown that E6 and E7 may only be transcribed from integrated or modified episomal HPV DNA (von Kleben Doeberitz et al., 1991, ibid). Therefore, the inventors surmise that detection of E6/E7 expression provides a direct indication of integrated HPV or modified episomal HPV and high oncogene activity, and conclude that in a clinical context detection of E6 (E6/E7) expression alone is sufficient to identify subjects at "high risk" of developing cervical carcinoma. In other words, if E6/E7 mRNA expression can be detected in a cervical sample, this is directly indicative of cellular abnormalities in the cervix and there is a very high risk of development of cervical carcinoma due to persistent HPV oncogene activity. Therefore, detection of E6/E7 mRNA in a human subject indicates that the subject has a very high risk of developing cervical carcinoma and should undergo immediate further screening, e.g. by colposcopy.

If HPV E6/E7 mRNA expression is not detected, the subject may still have an HPV infection. However due to absence of integration and oncogene activity, it may regress spontaneously (as observed by Pietsaro et al., 2002, ibid).

In a clinical context the performance of methods which rely on screening for expression of E6 mRNA alone is critically dependent on the ability to score a negative result for E6 mRNA expression with confidence. This again requires a detection technique which has maximal sensitivity, yet produces minimal false-negative results. In a preferred embodiment this is achieved by using a sensitive amplification and real-time detection technique to screen for the presence or absence of E6 mRNA. The most preferred technique is real-time NASBA amplification using molecular beacons probes, as described by Leone et al., Nucleic Acids Research., 1998, Vol 26, 2150-2155. Due to the sensitivity of this technique the occurrence of false-negative results is minimised and a result of "negative E6 expression" can be scored with greater confidence. This is extremely important if the assays are to be used in the context of a clinical screening program.

In the methods based on detection of E6 mRNA alone it is preferred to detect at least types HPV 16, 18, 31, 33 and 45, and in a preferred embodiment the assay may detect only these HPV types. DNA from HPV types 16, 18, 31 and 33 has been detected in more than 87% of cervical carcinoma samples (Karlsen et al., 1996, J Clin Microbiol, 34:2095-2100). Other studies have shown that E6 and E7 are almost invariably retained in cervical cancers, as their expression is likely to be necessary for conversion to and maintenance of the malignant state (Choo et al., 1987, J Med Virol 21:101-107; Durst et al., 1995, Cancer Genet Cytogenet, 85: 105-112). In contrast to HPV detection systems which are based on detection of the undamaged genome or the L1 gene sequence, detection of HPV mRNA expressed from the E6/E7 area may detect more than 90% of the patients directly related to a risk of developing cervical carcinoma.

In the clinic, methods based on detection of E6 mRNA are preferred for use in post-screening, i.e. further analysis of individuals having a previous diagnosis of ASCUS, CIN 1 or Condyloma. The method may be used to select those with a high risk of developing cervical carcinoma from amongst the group of individuals having a previous diagnosis of ASCUS, CIN 1 or Condyloma. ASCUS, Condyloma and CIN I may be defined as more or less the same diagnosis due to very low reproducibility between different cytologists and different cytological departments. Östör (Int J. Gyn Path. 12:186-192. 1993) found that only around 1% of the CIN 1 cases may progress to cervical carcinoma. Thus, there is a genuine need for an efficient method of identifying the subset of individuals with ASCUS, Condyloma or CIN I who are at substantial risk of developing cervical carcinoma. One of HPV types 16, 18, 31 or 33 was detected in 87% of the cervical carcinoma cases study by Karlsen et al., 1996. By inclusion of HPV 45, nearly 90% of the cervical carcinoma samples are found to be related to these five HPV types. Therefore, calculated from the data provided by Östör (Int J. Gyn Path. 12:186-192. 1993) more than 99.9% are detected cases with ASCUS, CIN I or condyloma are missed by our HPV-Proofer kit.

In the methods of the invention "positive expression" of an mRNA is taken to mean expression above background. There is no absolute requirement for accurate quantitative determination of the level of mRNA expression or for accurate determination of the relative levels of expression of L1 and E6 mRNA.

In certain embodiments, the methods of the invention may comprise a quantitative determination of levels of mRNA expression. In a preferred embodiment in order to provide a clear distinction between "positive expression" and "negative expression" a determination of "positive expression" may require the presence of more than 50 copies of the relevant mRNA (per ml of sample or per total volume of sample), whereas a determination of "negative expression" may require the presence of less than 1 copy of the relevant mRNA (per ml of sample or per total volume of sample).

The methods of the invention will preferably involve screening for E6 mRNA using a technique which is able to detect specifically E6 mRNA from cancer-associated HPV types, more preferably "high risk" cancer-associated HPV types. In the most preferred embodiment the methods involve screening for E6 mRNA using a technique which is able to detect E6 mRNA from HPV types 16, 18, 31 and 33, and preferably also 45. Most preferably, the method will specifically detect expression of E6 mRNA from at least one of HPV types 16, 18, 31, 33, and preferably also 45, and most preferably all five types. However, women positive for positive for expression of E6 from other types than 16, 18, 31, 33 and 45, e.g. 35, 39, 45, 52, 56, 58, 59, 66 and 68 may still be "at risk" of developing cervical carcinoma. Thus, the method may encompass screening for expression of E6 mRNA from one or more of these HPV types, most preferably in addition to screening for E6 mRNA from HPV types 16, 18, 31, 33 and 45. Certain HPV types exhibit a marked geographical/population distribution. Therefore, it may be appropriate to include primers specific for an HPV type known to be prevalent in the population/geographical area under test, for example in addition to screening for HPV types 16, 18, 31, 33 and 45.

For the avoidance of doubt, unless otherwise stated the term "E6 mRNA" as used herein encompasses all naturally occurring mRNA transcripts which contain all or part of the E6 open reading frame, including naturally occurring splice variants, and therefore includes transcripts which additionally contain all or part of the E7 open reading frame (and indeed further open reading frames). The terms "E6/E7 mRNA", "E6/E7 transcripts" etc are used interchangeably with the terms "E6 mRNA", "E6 transcripts" and also encompass naturally occurring mRNA transcripts which contain all or part of the E6 open reading frame, including naturally occurring splice variants, and transcripts which contain all or part of the E7 open reading frame. The term "oncogene expression", unless otherwise stated, also refers to naturally occurring mRNA transcripts which contain all or part of the E6 open reading frame, including naturally occurring splice variants, and transcripts which contain all or part of the E7 open reading frame.

Four E6/E7 mRNA species have so far been described in cells infected with HPV 16, namely an unspliced E6 transcript and three spliced transcripts denoted E6*I, E6*II and E6*III (Smotkin D, et al., J. Virol. 1989 March 63(3):1441-7; Smotkin D, Wettstein F O. Proc Natl Acad Sci USA. 1986 July 83(13):4680-4; Doorbar J. et al., Virology. 1990 September 178(1):254-62; Cornelissen M T, et al. J Gen Virol. 1990 May 71(Pt 5):1243-6; Johnson M A, et al. J Gen Virol. 1990 July 71(Pt 7):1473-9; Schneider-Maunoury S, et al. J. Virol. 1987 October 61(10):3295-8; Sherman L, et al. Int J. Cancer. 1992 February 50(3):356-64). All four transcripts are transcribed from a single promoter (p97) located just upstream of the second ATG of the E6 ORF.

In one embodiment the methods may comprise screening for E6 transcripts which contain all or part of the E7 open reading frame, This may be accomplished, for example, using primers or probes specific for the E7 coding region.

In a further embodiment, the methods may comprise screening for the presence of "full length" E6 transcripts. In the case of HPV 16 the term "full length E6 transcripts" refers to transcripts which contain all of the region from nucleotide (nt) 97 to nt 880 in the E6 ORF, inclusive of nt 97 and 880. Nucleotide positions are numbered according to standard HPV nomenclature (see Human Papillomavirus Compendium OnLine, available via the internet or in paper form from HV Database, Mail Stop K710, Los Alamos National Laboratory, Los Alamos, N. Mex. 87545, USA). Specific detection of full length transcripts may be accomplished, for example, using primers or probes which are specific for the region which is present only in full length E6 transcripts, not in splice variants. Different HPV types exhibit different patterns of E6/E7 mRNA expression. Transcript maps for various HPV types, including HPV types 16 and 31, which may be used to assist in the design of probes or primers for detection of E6/E7 transcripts are publicly available via the Human Papillomavirus Compendium (as above).

E6 oligonucleotide primers are described herein which are suitable for use in amplification of regions of the E6 mRNA from various HPV types by NASBA or PCR.

In a preferred embodiment methods which involve screening for L1 mRNA expression may comprise screening for L1 mRNA expression using a technique which is able to detect L1 mRNA from substantially all known HPV types or at least the major cancer-associated HPV types (e.g. preferably all of HPV types 16, 18, 31 and 33). L1 primers and probes are described herein which are capable of detecting L1 mRNA from HPV types 6, 11, 16, 18, 31, 33, 35 and 51 in cervical samples.

Detection of L1 transcripts can be said to detect HPV "virulence", meaning the presence of HPV lytic activity. Detection of E6/E7 transcripts can be said to detect HPV "pathogenesis" since expression of these mRNAs is indicative of molecular events associated with risk of developing carcinoma.

In a study of 4589 women it was possible to detect all except one case of CIN III lesions or cancer using a method based on screening for expression of E6 and L1 mRNA (see accompanying Examples).

In further embodiments, the above-described methods of the invention may comprise screening for expression of mRNA transcripts from the human p16$^{ink4a}$ gene, in addition to screening for expression of HPV L1 and/or E6 transcripts.

A positive result for expression of p16$^{ink4a}$ mRNA is taken as a further indication of risk of developing cervical carcinoma.

P16$^{ink4a}$, and the related family members, may function to regulate the phosphorylation and the growth suppressive activity of the restinoblastoma gene product (RB). In support of this, it has been found that there is an inverse relationship between the expression of p16$^{ink4a}$ protein and the presence of normal RB in selected cancer cell lines; p16$^{ink4a}$ protein is detectable when RB is mutant, deleted, or inactivated, and it is markedly reduced or absent in cell lines that contain a normal RB. Kheif et al. (Kheif S N et al., Proc. Natl. Acad. Sci. USA 93:4350-4354. 1996), found that p16$^{ink4a}$ protein is expressed in human cervical carcinoma cells that contain either a mutant RB or a wild-type RB that is functionally inactivated by E7. They also show that the inactivation of RB correlates with an upregulation of p16$^{ink4a}$ confirming a feedback loop involving p16$^{ink4a}$ and RB. Milde-Langosch et al. (Milde-Langosch K, et al., (2001) Virchows Arch 439: 55-61) found that there were significant correlations between strong p16 expression and HPV16/18 infection and between strong p16 expression and HPV 16/18 E6/E7 oncogene expression. Klaes et al., (Klaes R, et al., (2001) Int J Cancer 92: 276-284) observed a strong over expression of the p16$^{ink4a}$ gene product in 150 of 152 high-grade dysplastic cervical lesions (CIN II to invasive cancer), whereas normal cervical epithelium or inflammatory or metaplastic lesions were not stained with the p16$^{ink4a}$ specific monoclonal antibody E6H4. All CIN I scored lesions associated with LR-HPV types displayed no or only focal or sporadic reactivity, whereas all but two CIN I scored lesions associated with HR-HPV types showed strong and diffuse staining for p16$^{ink4a}$.

The disclosed screening methods may be carried out on a preparation of nucleic acid isolated from a clinical sample or biopsy containing cervical cells taken from the subject under test. Suitable samples which may be used as a source of nucleic acid include (but not exclusively) cervical swabs, cervical biopsies, cervical scrapings, skin biopsies/warts, also paraffin embedded tissues, and formalin or methanol fixed cells.

The preparation of nucleic acid to be screened using the disclosed method must include mRNA, however it need not be a preparation of purified poly A+ mRNA and preparations of total RNA or crude preparations of total nucleic acid containing both RNA and genomic DNA, or even crude cell lysates are also suitable as starting material for a NASBA reaction. Essentially any technique known in the art for the isolation of a preparation of nucleic acid including mRNA may be used to isolate nucleic acid from a test sample. A preferred technique is the "Boom" isolation method described in U.S. Pat. No. 5,234,809 and EP-B-0389,063. This method, which can be used to isolate a nucleic acid preparation containing both RNA and DNA, is based on the nucleic acid binding properties of silicon dioxide particles in the presence of the chaotropic agent guanidine thiocyanate (GuSCN).

The methods of the invention are based on assessment of active transcription of the HPV genome in cervical cells. The methods are not limited with respect to the precise technique used to detect mRNA expression. Many techniques for detection of specific mRNA sequences are known in the art and may be used in accordance with the invention. For example, specific mRNAs may be detected by hybridisation, amplification or sequencing techniques.

It is most preferred to detect mRNA expression by means of an amplification technique, most preferably an isothermal amplification such as NASBA, transcription-mediated amplification, signal-mediated amplification of RNA technology, isothermal solution phase amplification, etc. All of these methods are well known in the art More preferably mRNA expression is detected by an isothermal amplification in combination with real-time detection of the amplification product. The most preferred combination is amplification by NASBA, coupled with real-time detection of the amplification product using molecular beacons technology, as described by Leone et al., Nucleic Acids Research, 1998, Vol 26, 2150-2155.

Methods for the detection of HPV in a test sample using the NASBA technique will generally comprise the following steps:

(a) assembling a reaction medium comprising suitable primer-pairs, an RNA directed DNA polymerase, a ribonuclease that hydrolyses the RNA strand of an RNA-DNA hybrid without hydrolysing single or double stranded RNA or DNA, an RNA polymerase that recognises said promoter, and ribonucleoside and deoxyribonucleoside triphosphates;

(b) incubating the reaction medium with a preparation of nucleic acid isolated from a test sample suspected of containing HPV under reaction conditions which permit a NASBA amplification reaction; and (c) detecting and/or quantitatively measuring any HPV-specific product of the NASBA amplification reaction.

Detection of the specific product(s) of the NASBA reaction (i.e. sense and/or antisense copies of the target RNA) may be carried out in a number of different ways. In one approach the NASBA product(s) may be detected with the use of an HPV-specific hybridisation probe capable of specifically annealing to the NASBA product. The hybridisation probe may be attached to a revealing label, for example a fluorescent, luminescent, radioactive or chemiluminescent compound or an enzyme label or any other type of label known to those of ordinary skill in the art. The precise nature of the label is not critical, but it should be capable of producing a signal detectable by external means, either by itself or in conjunction with one or more additional substances (e.g. the substrate for an enzyme).

A preferred detection method is so-called "real-time NASBA" which allows continuous monitoring of the formation of the product of the NASBA reaction over the course of the reaction. In a preferred embodiment this may be achieved using a "molecular beacons" probe comprising an HPV-specific sequence capable of annealing to the NASBA product, a stem-duplex forming oligonucleotide sequence and a pair of fluorescer/quencher moieties, as known in the art and described herein. If the molecular beacons probe is added to the reaction mixture prior to amplification it may be possible to monitor the formation of the NASBA product in real-time (Leone et al., Nucleic Acids Research, 1998, Vol 26, 2150-2155). Reagent kits and instrumentation for performing real-time NASBA detection are available commercially (e.g. NucliSens™ EasyQ system, from Organon Teknika).

In a further approach, the molecular beacons technology may be incorporated into the primer 2 oligonucleotide allowing real-time monitoring of the NASBA reaction without the need for a separate hybridisation probe.

In a still further approach the products of the NASBA reaction may be monitored using a generic labelled detection probe which hybridises to a nucleotide sequence in the 5' terminus of the primer 2 oligonucleotide. This is equivalent to the "NucliSens™" detection system supplied by Organon Teknika. In this system specificity for NASBA products derived from the target HPV mRNA may be conferred by using HPV-specific capture probes comprising probe oligonucleotides as described herein attached to a solid support such as a magnetic microbead. Most preferably the generic labelled detection probe is the ECL™ detection probe supplied by Organon Teknika. NASBA amplicons are hybridized to the HPV-specific capture probes and the generic ECL probe (via a complementary sequence on primer 2). Following hybridization the bead/amplicon/ECL probe complexes may be captured at the magnet electrode of an automatic ECL reader (e.g. the NucliSens™ reader supplied by Organon Teknika). Subsequently, a voltage pulse triggers the ECL™ reaction.

The detection of HPV mRNA is also of clinical relevance in cancers other than cervical carcinoma including, for example, head and neck carcinoma, oral and tongue carcinoma, skin carcinoma, anal and vaginal carcinoma. Detection of HPV mRNA may also be very useful in the diagnosis of micrometastases in lymph nodes in the lower part of the body. Hence, the invention also contemplates screens for susceptibility to the above-listed cancers based on screening for expression of HPV L1 and E6 transcripts.

In accordance with a further aspect of the invention there is provided a kit for use in the detection of transcripts of the L1 and E6 genes of HPV, the kit comprising at least one primer-pair suitable for use in amplification of a region of L1 transcripts from at least HPV types 16, 18, 31 and 33, and preferably also HPV 45, and one or more primer-pairs which enable amplification of a region of E6 transcripts from HPV types 16, 18, 31 and 33, and preferably also HPV 45.

"Primer-pair" taken to mean are pair of primers which may be used in combination to amplify a specific region of the L1 or E6 mRNA using any known nucleic acid technique. In preferred embodiments the primer-pairs included in the kit will be suitable for use in NASBA amplification or similar isothermal amplification techniques.

The individual primers making up each primer-pair included in the kit may be supplied separately (e.g. a separate container of each primer) or, more preferably, may be supplied mixed in a single container. Combinations of two or more primer-pairs may be supplied ready-mixed in a single container within the kit. It may be convenient to supply two or more primer-pairs in a single container where the two or more amplification reactions are to be "multiplexed", meaning performed simultaneously in a single reaction vessel.

The primer-pair(s) suitable for use in amplification of a region of E6 transcripts should enable amplification a region of E6 mRNA from at least the major cancer-associated HPV types 16, 18, 31 and 33, and preferably also HPV 45. There are several different ways in which this can be achieved.

In one embodiment, the kit may contain separate primer-pairs specific for each of HPV types 16, 18, 31 and 33, and preferably also HPV 45. These primer-pairs may be supplied within the kit in separate containers, or they may be supplied as mixtures of two or more primer-pairs in a single container, for example to enable multiplexing of the amplification reactions.

In a further embodiment, the kit may contain a single primer-pair capable of amplifying a region of the E6 gene from HPV types 16, 18, 31 and 33, and preferably also HPV 45, which thus enables amplification of all four (preferably five) types in a single amplification reaction. This could, for example, be achieved with the use of a pair of degenerate primers or by selection of a region of the E6 mRNA which is highly conserved across HPV types.

The E6 primer-pair may correspond to any region of the E6 mRNA, an may enable amplification of all or part of the E6 open reading frame and/or the E7 open reading frame.

The kit may further include primer-pairs suitable for use in amplification of E6 mRNA from HPV types other than types 16, 18, 31 and 33, and preferably also HPV 45. For example, the kit may be supplemented with E6 primers for detection of an HPV type which is endemic in a particular geographical area or population.

The primer-pair(s) suitable for use in amplification of a region of L1 transcripts should be capable of amplifying a region of L1 mRNA from at least the major cancer-associated HPV types 16, 18, 31 and 33, and preferably also HPV 45, and will preferably be suitable for use in amplification of a region of L1 mRNAs from substantially all known HPV types. With the use of such primers it is possible to test for active transcription of L1 mRNA from multiple HPV types in a single amplification reaction.

It is possible to design primers capable of detecting L1 transcripts from multiple HPV types by selecting regions of the L1 transcript which are highly conserved.

In a further approach, specificity for multiple HPV types may be achieved with the use of degenerate oligonucleotide primers or complex mixtures of polynucleotides which exhibit minor sequence variations, preferably corresponding to sites of sequence variation between HPV genotypes. The rationale behind the use of such degenerate primers or mixtures is that the mixture may contain at least one primer-pair capable of detecting each HPV type.

In a still further approach specificity for multiple HPV types may be achieved by incorporating into the primers one or more inosine nucleotides, preferably at sites of sequence variation between HPV genotypes.

The E6 and L1 primer-pairs may be supplied in separate containers within the kit, or the L1 primer-pair(s) may be supplied as a mixture with one or more E6 primer-pairs in a single container.

The kits may further comprise one or more probes suitable for use in detection of the products of amplification reactions carried out using the primer-pairs included within the kit. The probe(s) may be supplied as a separate reagent within the kit. Alternatively, the probe(s) may be supplied as a mixture with one or more primer-pairs.

The primers and probes included in the kit are preferably single stranded DNA molecules. Non-natural synthetic polynucleotides which retain the ability to base-pair with a complementary nucleic acid molecule may also be used, including synthetic oligonucleotides which incorporate modified bases and synthetic oligonucleotides wherein the links between individual nucleosides include bonds other than phosphodiester bonds. The primers and probes may be produced according to techniques well known in the art, such as by chemical synthesis using standard apparatus and protocols for oligonucleotide synthesis.

The primers and probes will typically be isolated single-stranded polynucleotides of no more than 100 bases in length, more typically less than 55 bases in length. For the avoidance of doubt it is hereby stated that the terms "primer" and "probe" exclude naturally occurring full-length HPV genomes.

Several general types of oligonucleotide primers and probes incorporating HPV-specific sequences may be included in the kit. Typically, such primers and probes may comprise additional, non-HPV sequences, for example sequences which are required for an amplification reaction or which facilitate detection of the products of the amplification reaction.

The first type of primers are primer 1 oligonucleotides (also referred to herein as NASBA P1 primers), which are oligonucleotides of generally approximately 50 bases in length, containing an average of about 20 bases at the 3' end that are complementary to a region of the target mRNA. Oligonucleotides suitable for use as NASBA P1 primers are denoted "P1/PCR" in Table 1. P1 primer oligonucleotides have the general structure $X_1$-SEQ, wherein SEQ represents an HPV-specific sequence and $X_1$ is a sequence comprising a promoter that is recognized by a specific RNA polymerase. Bacteriophage promoters, for example the T7, T3 and SP6 promoters, are preferred for use in the oligonucleotides of the invention, since they provide advantages of high level transcription which is dependent only on binding of the appropriate RNA polymerase. In a preferred embodiment, sequence "$X_1$" may comprise the sequence AAT-TCTAATACGACTCACTATAGGG (SEQ ID No 171) or the sequence AATTCTAATACGACTCACTATAGG-GAGAAGG (SEQ ID No 172). These sequences contains a T7 promoter, including the transcription initiation site for T7 RNA polymerase.

The HPV-specific sequences in the primers denoted in Table 1 as "P1/PCR" may also be adapted for use in standard PCR primers. When these sequences are used as the basis of NASBA P1 primers they have the general structure $X_1$-SEQ, as defined above. The promoter sequence $X_1$ is essential in a NASBA P1 primer. However, when the same sequences are used as the basis of standard PCR primers it is not necessary to include $X_1$.

A second type of primers are NASBA primer 2 oligonucleotides (also referred to herein as NASBA P2 primers) which generally comprise a sequence of approximately 20 bases substantially identical to a region of the target mRNA. The oligonucleotide sequences denoted in Table 1 as "P2/PCR" are suitable for use in both NASBA P2 primers and standard PCR primers.

Oligonucleotides intended for use as NASBA P2 primers may, in a particular but non-limiting embodiment, further comprise a sequence of nucleotides at the 5' end which is unrelated to the target mRNA but which is capable of hybridising to a generic detection probe. The detection probe will preferably be labelled, for example with a fluorescent, luminescent or enzymatic label. In one embodiment the detection probe is labelled with a label that permits detection using ECL™ technology, although it will be appreciated that the invention is in no way limited to this particular method of detection. In a preferred embodiment the 5' end of the primer 2 oligonucleotides may comprise the sequence GATG-CAAGGTCGCATATGAG (SEQ ID No 170). This sequence is capable of hybridising to a generic ECL™ probe commercially available from Organon Teknika having the following structure:

$Ru(bpy)_3^{2+}$-GAT GCA AGG TCG CAT ATG AG-3'

In a different embodiment the primer 2 oligonucleotide may incorporate "molecular beacons" technology, which is known in the art and described, for example, in WO 95/13399 by Tyagi and Kramer, Nature Biotechnology. 14: 303-308, 1996, to allow for real-time monitoring of the NASBA reaction.

Target-specific probe oligonucleotides may also be included within the kit. Probe oligonucleotides generally comprise a sequence of approximately 20-25 bases substantially identical to a region of the target mRNA, or the complement thereof. Example HPV-specific oligonucleotide sequences which are suitable for use as probes are denoted "PO" in Table 1. The probe oligonucleotides may be used as target-specific hybridisation probes for detection of the products of a NASBA or PCR reaction. In this connection the probe oligonucleotides may be coupled to a solid support, such as paramagnetic beads, to form a capture probe (see below). In a preferred embodiment the 5' end of the probe oligonucleotide may be labelled with biotin. The addition of a biotin label facilitates attachment of the probe to a solid support via a biotin/streptavidin or biotin/avidin linkage.

Target-specific probes enabling real-time detection of amplification products may incorporate "molecular beacons" technology which is known in the art and described, for example, by Tyagi and Kramer, Nature Biotechnology. 14: 303-308, 1996 and in WO 95/13399. Example HPV-specific oligonucleotide sequences suitable for use as molecular beacons probes are denoted "MB" in Table 1.

The term "molecular beacons probes" as used herein is taken to mean molecules having the structure:

$X_2$-$arm_1$-target-$arm_2$-$X_3$ wherein "target" represents a target-specific sequence of nucleotides, "$X_2$" and "$X_3$" represent a fluorescent moiety and a quencher moiety capable of substantially or completely quenching the fluorescence from the fluorescent moiety when the two are held together in close proximity and "arm$_1$" and "arm$_2$" represent complementary sequences capable of forming a stem duplex.

Preferred combinations of "arm$_1$" and "arm$_2$" sequences are as follows, however these are intended to be illustrative rather than limiting to the invention:

```
cgcatg-SEQ-catgcg ccagct-SEQ-agctgg cacgc-SEQ-gcgtg cgatcg-SEQ-cgatcg ccgtcg-SEQ-cgacgg cggacc-SEQ-ggtccg ccgaagg-SEQ-ccttcgg cacgtcg-SEQ-cgacgtg cgcagc-SEQ-gctgcg ccaagc-SEQ-gcttgg ccaagcg-SEQ-cgcttgg cccagc-SEQ-gctggg ccaaagc-SEQ-gctttgg cctgc-SEQ-gcagg ccaccc-SEQ-gggtgg ccaagcc-SEQ-ggcttgg ccagcg-SEQ-cgctgg cgcatg-SEQ-catgcg
```

The use of molecular beacons technology allows for real-time monitoring of amplification reactions, for example NASBA amplification (see Leone et al., Nucleic Acids Research., 1998, vol: 26, pp 2150-2155). The molecular beacons probes generally include complementary sequences flanking the HPV-specific sequence, represented herein by the notation arm$_1$ and arm$_2$, which are capable of hybridising to each other form a stem duplex structure. The precise sequences of arm$_1$ and arm$_2$ are not material to the invention, except for the requirement that these sequences must be capable of forming a stem duplex when the probe is not bound to a target HPV sequence.

Molecular beacons probes also include a fluorescent moiety and a quencher moiety, the fluorescent and the quencher moieties being represented herein by the notation X$_2$ and X$_3$. As will be appreciated be the skilled reader, the fluorescer and quencher moieties are selected such that the quencher moiety is capable of substantially or completely quenching the fluorescence from the fluorescent moiety when the two moieties are in close proximity, e.g. when the probe is in the hairpin "closed" conformation in the absence of the target sequence. Upon binding to the target sequence, the fluorescent and quencher moieties are held apart such that the fluorescence of the fluorescent moiety is no longer quenched.

Many examples of suitable pairs of quencher/fluorescer moieties which may be used in accordance with the invention are known in the art (see WO 95/13399, Tyagi and Kramer, ibid). A broad range of fluorophores in many different colours made be used, including for example 5-(2'-aminoethyl)ami-nonaphthalene-1-sulphonic acid (EDANS), fluorescein, FAM and Texas Red (see Tyagi, Bratu and Kramer, 1998, Nature Biotechnology, 16, 49-53. The use of probes labelled with different coloured fluorophores enables "multiplex" detection of two or more different probes in a single reaction vessel. A preferred quencher is 4-(4'-dimethylaminopheny-lazo)benzoic acid (DABCYL), a non-fluorescent chromophore, which serves as a "universal" quencher for a wide range of fluorophores. The fluorescer and quencher moieties may be covalently attached to the probe in either orientation, either with the fluorescer at or near the 5' end and the quencher at or near the 3' end or vice versa. Protocols for the synthesis of molecular beacon probes are known in the art. A detailed protocol for synthesis is provided in a paper entitled "Molecular Beacons: Hybridization Probes for Detection of Nucleic Acids in Homogenous Solutions" by Sanjay Tyagi et al., Department of Molecular Genetics, Public Health Research Institute, 455 First Avenue, New York, NY 10016, USA, which is available online via the PHRI website (at phri.ny-u.edu or molecular-beacons.org)

Suitable combinations of the NASBA P1 and NASBA P2 primers may be used to drive a NASBA amplification reaction. In order to drive a NASBA amplification reaction the primer 1 and primer 2 oligonucleotides must be capable of priming synthesis of a double-stranded DNA from a target region of mRNA. For this to occur the primer 1 and primer 2 oligonucleotides must comprise target-specific sequences which are complementary to regions of the sense and the antisense strand of the target mRNA, respectively.

In the first phase of the NASBA amplification cycle, the so-called "non-cyclic" phase, the primer 1 oligonucleotide anneals to a complementary sequence in the target mRNA and its 3' end is extended by the action of an RNA-dependent DNA polymerase (e.g. reverse transcriptase) to form a first-strand cDNA synthesis. The RNA strand of the resulting RNA:DNA hybrid is then digested, e.g. by the action of RNaseH, to leave a single stranded DNA. The primer 2 oligonucleotide anneals to a complementary sequence towards the 3' end of this single stranded DNA and its 3' end is extended (by the action of reverse transcriptase), forming a double stranded DNA. RNA polymerase is then able to transcribe multiple RNA copies from the now transcriptionally active promoter sequence within the double-stranded DNA. This RNA transcript, which is antisense to the original target mRNA, can act as a template for a further round of NASBA reactions, with primer 2 annealing to the RNA and priming synthesis of the first cDNA strand and primer 1 priming synthesis of the second cDNA strand. The general principles of the NASBA reaction are well known in the art (see Compton, J. Nature. 350: 91-92).

The target-specific probe oligonucleotides described herein may also be attached to a solid support, such as magnetic microbeads, and used as "capture probes" to immobilise the product of the NASBA amplification reaction (a single stranded RNA). The target-specific "molecular beacons" probes described herein may be used for real-time monitoring of the NASBA reaction.

Kits according to the invention may also including a positive control containing E6 and/or L1 mRNA from a known HPV type. Suitable controls include, for example, nucleic acid extracts prepared from cell lines infected with known HPV types (e.g. HeLa, CaSki).

Kits further may contain internal control amplification primers, e.g. primers specific for human U1A RNA.

Kits containing primers (and optionally probes) suitable for use in NASBA amplification may further comprise a mixture of enzymes required for the NASBA reaction, e.g. enzyme mixture containing an RNA directed DNA polymerase (e.g. a reverse transcriptase), a ribonuclease that hydrolyses the RNA strand of an RNA-DNA hybrid without hydrolysing single or double stranded RNA or DNA (e.g. RNaseH) and an RNA polymerase. The RNA polymerase should be one which recognises the promoter sequence present in the 5' terminal region of the NASBA P1 primers supplied in the reagent kit. The kit may also comprise a supply of NASBA buffer containing the ribonucleosides and deoxyribonucleosides required for RNA and DNA synthesis. The composition of a standard NASBA reaction buffer will be well known to those skilled in the art (see also Leone et al., ibid).

TABLE 1

E6-specific sequences for inclusion in NASBA/PCR primers and probes

| SEQ ID | Primer/probe type | Sequence | HPV Type | nt |
|---|---|---|---|---|
| 1 | P2/PCR | CCACAGGAGCGACCCAGAAAGTTA | 16 | 116 |
| 2 | P1/PCR | $X_1$-ACGGTTTGTTGTATTGCTGTTC | 16 | 368 |
| 3 | P2/PCR | CCACAGGAGCGACCCAGAAA | 16 | 116 |
| 4 | P1/PCR | $X_1$-GGTTTGTTGTATTGCTGTTC | 16 | 368 |
| 5 | P1/PCR | $X_1$-ATTCCCATCTCTATATACTA | 16 | 258 |
| 6 | P1/PCR | $X_1$-TCACGTCGCAGTAACTGT | 16 | 208 |
| 7 | P1/PCR | $X_1$-TTGCTTGCAGTACACACA | 16 | 191 |
| 8 | P1/PCR | $X_1$-TGCAGTACACACATTCTA | 16 | 186 |
| 9 | P1/PCR | $X_1$-GCAGTACACACATTCTAA | 16 | 185 |
| 10 | P2/PCR | ACAGTTATGCACAGAGCT | 16 | 142 |
| 11 | P2/PCR | ATATTAGAATGTGTGTAC | 16 | 182 |
| 12 | P2/PCR | TTAGAATGTGTGTACTGC | 16 | 185 |
| 13 | P2/PCR | GAATGTGTGTACTGCAAG | 16 | 188 |
| 14 | PO | ACAGTTATGCACAGAGCT | 16 | 142 |
| 15 | PO | ATATTAGAATGTGTGTAC | 16 | 182 |
| 16 | PO | TTAGAATGTGTGTACTGC | 16 | 185 |
| 17 | PO | GAATGTGTGTACTGCAAG | 16 | 188 |
| 18 | PO | CTTTGCTTTTCGGGATTTATGC | 16 | 235 |
| 19 | PO | TATGACTTTGCTTTTCGGGA | 16 | 230 |
| 20 | MB | $X_2$-$arm_1$-TATGACTTTGCTTTTCGGGA-$arm_2$-$X_3$ | 16 | 230 |
| 21 | P2/PCR | CAGAGGAGGAGGATGAAATAGTA | 16 | 656 |
| 22 | P1/PCR | $X_1$-GCACAACCGAAGCGTAGAGTCACAC | 16 | 741 |
| 23 | PO | TGGACAAGCAGAACCGGACAGAGC | 16 | 687 |
| 24 | P2/PCR | CAGAGGAGGAGGATGAAATAGA | 16 | 656 |
| 25 | P1/PCR | $X_1$-GCACAACCGAAGCGTAGAGTCA | 16 | 741 |
| 26 | PO | AGCAGAACCGGACAGAGCCCATTA | 16 | 693 |
| 27 | P2/PCR | ACGATGAAATAGATGGAGTT | 18 | 702 |
| 28 | P1/PCR | $X_1$-CACGGACACACAAAGGACAG | 18 | 869 |
| 28 | PO | AGCCGAACCACAACGTCACA | 18 | 748 |
| 30 | P2/PCR | GAAAACGATGAAATAGATGGAG | 18 | 698 |
| 31 | P1/PCR | $X_1$-ACACCACGGACACACAAAGGACAG | 18 | 869 |
| 32 | PO | GAACCACAACGTCACACAATG | 18 | 752 |

TABLE 1-continued

E6-specific sequences for inclusion in NASBA/PCR primers and probes

| SEQ ID | Primer/ probe type | Sequence | HPV Type | nt |
|---|---|---|---|---|
| 33 | MB | $X_2$-$arm_1$-GAACCACAACGTCACACAATG-$arm_2$-$X_3$ | 18 | 752 |
| 34 | P2/PCR | TTCCGGTTGACCTTCTATGT | 18 | 651 |
| 35 | P1/PCR | $X_1$-GGTCGTCTGCTGAGCTTTCT | 18 | 817 |
| 36 | P2/PCR | GCAAGACATAGAAATAACCTG | 18 | 179 |
| 37 | P1/PCR | $X_1$-ACCCAGTGTTAGTTAGTT | 18 | 379 |
| 38 | PO | TGCAAGACAGTATTGGAACT | 18 | 207 |
| 39 | P2/PCR | GGAAATACCCTACGATGAAC | 31 | 164 |
| 40 | P1/PCR | $X_1$-GGACACAACGGTCTTTGACA | 31 | 423 |
| 41 | PO | ATAGGGACGACACACCACACGGAG | 31 | 268 |
| 42 | P2/PCR | GGAAATACCCTACGATGAACTA | 31 | 164 |
| 43 | P1/PCR | $X_1$-CTGGACACAACGGTCTTTGACA | 31 | 423 |
| 44 | PO | TAGGGACGACACACCACACGGA | 31 | 269 |
| 45 | P2/PCR | ACTGACCTCCACTGTTATGA | 31 | 617 |
| 46 | P1/PCR | $X_1$-TATCTACTTGTGTGCTCTGT | 31 | 766 |
| 47 | PO | GACAAGCAGAACCGGACACATC | 31 | 687 |
| 48 | P2/PCR | TGACCTCCACTGTTATGAGCAATT | 31 | 619 |
| 49 | P1/PCR | $X_1$-TGCGAATATCTACTTGTGTGCTCT GT | 31 | 766 |
| 50 | PO | GGACAAGCAGAACCGGACACATCCAA | 31 | 686 |
| 51 | MB | $X_2$-$arm_1$-GGACAAGCAGAACCGGACACATCCAA-$arm_2$-$X_3$ | 31 | 686 |
| 52 | P2/PCR | ACTGACCTCCACTGTTAT | 31 | 617 |
| 53 | P1/PCR | $X_1$-CACGATTCCAAATGAGCCCAT | 31 | 809 |
| 54 | P2/PCR | TATCCTGAACCAACTGACCTAT | 33 | 618 |
| 55 | P1/PCR | $X_1$-TTGACACATAAACGAACTG | 33 | 763 |
| 56 | PO | CAGATGGACAAGCACAACC | 33 | 694 |
| 57 | P2/PCR | TCCTGAACCAACTGACCTAT | 33 | 620 |
| 58 | P1/PCR | $X_1$-CCCATAAGTAGTTGCTGTAT | 33 | 807 |
| 59 | PO | GGACAAGCACAACCAGCCACAGC | 33 | 699 |
| 60 | MB | $X_2$-$arm_1$-GGACAAGCACAACCAGCCACAGC-$arm_2$-$X_3$ | 33 | 699 |
| 61 | P2/PCR | GACCTTTGTGTCCTCAAGAA | 33 | 431 |
| 62 | P1/PCR | $X_1$-AGGTCAGTTGGTTCAGGATA | 33 | 618 |
| 63 | PO | AGAAACTGCACTGTGACGTGT | 33 | 543 |
| 64 | P2/PCR | ATTACAGCGGAGTGAGGTAT | 35 | 217 |
| 65 | P1/PCR | $X_1$-GTCTTTGCTTTTCAACTGGA | 35 | 442 |
| 66 | PO | ATAGAGAAGGCCAGCCATAT | 35 | 270 |
| 67 | P2/PCR | TCAGAGGAGGAGGAAGATACTA | 35 | 655 |

TABLE 1-continued

E6-specific sequences for inclusion in NASBA/PCR primers and probes

| SEQ ID | Primer/ probe type | Sequence | HPV Type | nt |
|---|---|---|---|---|
| 68 | P1/PCR | X$_1$-GATTATGCTCTCTGTGAACA | 35 | 844 |
| 69 | P2/PCR | CCCGAGGCAACTGACCTATA | 35 | 610 |
| 70 | P1/PCR | X$_1$-GTCAATGTGTGTGCTCTGTA | 35 | 770 |
| 71 | PO | GACAAGCAAAACCAGACACCTCCAA | 35 | 692 |
| 72 | PO | GACAAGCAAAACCAGACACC | 35 | 692 |
| 73 | P2/PCR | TTGTGTGAGGTGCTGGAAGAAT | 52 | 144 |
| 74 | P1/PCR | X$_1$-CCCTCTCTTCTAATGTTT | 52 | 358 |
| 75 | PO | GTGCCTACGCTTTTTATCTA | 52 | 296 |
| 76 | P2/PCR | GTGCCTACGCTTTTTATCTA | 52 | 296 |
| 77 | P1/PCR | X$_1$-GGGGTCTCCAACACTCTGAACA | 52 | 507 |
| 78 | PO | TGCAAACAAGCGATTTCA | 52 | 461 |
| 79 | P2/PCR | TCAGGCGTTGGAGACATC | 58 | 157 |
| 80 | P1/PCR | X$_1$-AGCAATCGTAAGCACACT | 58 | 301 |
| 81 | P2/PCR | TCTGTGCATGAAATCGAA | 58 | 173 |
| 82 | P1/PCR | X$_1$-AGCACACTTTACATACTG | 58 | 291 |
| 83 | PO | TGAAATGCGTTGAATGCA | 58 | 192 |
| 84 | PO | TTGCAGCGATCTGAGGTATATG | 58 | 218 |
| 85 | P2/PCR | TACACTGCTGGACAACAT | B (11) | 514 |
| 86 | P1/PCR | X$_1$-TCATCTTCTGAGCTGTCT | B (11) | 619 |
| 87 | P2/PCR | TACACTGCTGGACAACATGCA | B (11) | 514 |
| 88 | P1/PCR | X$_1$-GTCACATCCACAGCAACAGGTCA | B (11) | 693 |
| 89 | PO | GTAGGGTTACATTGCTATGA | B (11) | 590 |
| 90 | PO | GTAGGGTTACATTGCTATGAGC | B (11) | 590 |
| 91 | P2/PCR | TGACCTGTTGCTGTGGATGTGA | B (11) | 693 |
| 92 | P1/PCR | X$_1$-TACCTGAATCGTCCGCCAT | B (11) | 832 |
| 93 | PO | ATWGTGTGTCCCATCTGC | B (11) | 794 |
| 94 | P2/PCR | CATGCCATAAATGTATAGA | C (18 39 45) | 295 |
| 95 | P1/PCR | X$_1$-CACCGCAGGCACCTTATTAA | C (18 39 45 | 408 |
| 96 | PO | AGAATTAGAGAATTAAGA | C (18 39 45 | 324 |
| 97 | P2/PCR | GCAGACGACCACTACAGCAAA | 39 | 210 |
| 98 | P1/PCR | X$_1$-ACACCGAGTCCGAGTAATA | 39 | 344 |
| 99 | PO | ATAGGGACGGGGAACCACT | 39 | 273 |
| 100 | P2/PCR | TATTACTCGGACTCGGTGT | 39 | 344 |
| 101 | P1/PCR | X$_1$-CTTGGGTTTCTCTTCGTGTTA | 39 | 558 |

TABLE 1-continued

E6-specific sequences for inclusion in NASBA/PCR primers and probes

| SEQ ID | Primer/probe type | Sequence | HPV Type | nt |
|---|---|---|---|---|
| 102 | PO | GGACCACAAAACGGGAGGAC | 39 | 531 |
| 103 | P2/PCR | GAAATAGATGAACCCGACCA | 39 | 703 |
| 104 | P1/PCR | X$_1$-GCACACCACGGACACACAAA | 39 | 886 |
| 105 | PO | TAGCCAGACGGGATGAACCACAGC | 39 | 749 |
| 106 | P2/PCR | AACCATTGAACCCAGCAGAAA | 45 | 430 |
| 107 | P1/PCR | X$_1$-TCTTTCTTGCCGTGCCTGGTCA | 45 | 527 |
| 108 | PO | GTACCGAGGGCAGTGTAATA | 45 | 500 |
| 109 | P2/PCR | AACCATTGAACCCAGCAGAAA | 45 | 430 |
| 110 | P1/PCR | X$_1$-TCTTTCTTGCCGTGCCTGGTCA | 45 | 527 |
| 111 | P2/PCR | GAAACCATTGAACCCAGCAGAAAA | 45 | 428 |
| 112 | P1/PCR | X$_1$-TTGCTATACTTGTGTTTCCCTACG | 45 | 558 |
| 113 | PO | GTACCGAGGGCAGTGTAATA | 45 | 500 |
| 114 | PO | GGACAAACGAAGATTTCACA | 45 | 467 |
| 115 | P2/PCR | GTTGACCTGTTGTGTTACCAGCAAT | 45 | 656 |
| 116 | P1/PCR | X$_1$-CACCACGGACACACAAAGGACAAG | 45 | 868 |
| 117 | P2/PCR | CTGTTGACCTGTTGTGTTACGA | 45 | 654 |
| 118 | P1/PCR | X$_1$-CCACGGACACACAAAGGACAAG | 45 | 868 |
| 119 | P2/PCR | GTTGACCTGTTGTGTTACGA | 45 | 656 |
| 120 | P1/PCR | X$_1$-ACGGACACACAAAGGACAAG | 45 | 868 |
| 121 | PO | GAGTCAGAGGAGGAAAACGATG | 45 | 686 |
| 122 | PO | AGGAAAACGATGAAGCAGATGGAGT | 45 | 696 |
| 123 | PO | ACAACTACCAGCCCGACGAGCCGAA | 45 | 730 |
| 124 | P2/PCR | GGAGGAGGATGAAGTAGATA | 51 | 658 |
| 125 | P1/PCR | X$_1$-GCCCATTAACATCTGCTGTA | 51 | 807 |
| 126 | P2/PCR | AGAGGAGGAGGATGAAGTAGATA | 51 | 655 |
| 127 | P1/PCR | X$_1$-ACGGGCAAACCAGGCTTAGT | 51 | 829 |
| 128 | PO | GCAGGTGTTCAAGTGTAGTA | 51 | 747 |
| 129 | PO | TGGCAGTGGAAAGCAGTGGAGACA | 51 | 771 |
| 130 | P2/PCR | TTGGGGTGCTGGAGACAAACATCT | 56 | 519 |
| 131 | P1/PCR | X$_1$-TTCATCCTCATCCTCATCCTCTGA | 56 | 665 |
| 132 | P2/PCR | TGGGGTGCTGGAGACAAACATC | 56 | 520 |
| 133 | P1/PCR | X$_1$-CATCCTCATCCTCATCCTCTGA | 56 | 665 |
| 134 | P2/PCR | TTGGGGTGCTGGAGACAAACAT | 56 | 519 |
| 135 | P1/PCR | X$_1$-CCACAAACTTACACTCACAACA | 56 | 764 |
| 136 | PO | AAAGTACCAACGCTGCAAGACGT | 56 | 581 |

TABLE 1-continued

E6-specific sequences for inclusion in NASBA/PCR primers and probes

| SEQ ID | Primer/probe type | Sequence | HPV Type | nt |
|---|---|---|---|---|
| 137 | PO | AGAACTAACACCTCAAACAGAAAT | 56 | 610 |
| 138 | PO | AGTACCAACGCTGCAAGACGTT | 56 | 583 |
| 139 | P1/PCR | X$_1$-TTGGACAGCTCAGAGGATGAGG | 56 | 656 |
| 140 | P2/PCR | GATTTTCCTTATGCAGTGTG | 56 | 279 |
| 141 | P1/PCR | X$_1$-GACATCTGTAGCACCTTATT | 56 | 410 |
| 142 | PO | GACTATTCAGTGTATGGAGC | 56 | 348 |
| 143 | PO | CAACTGAYCTMYACTGTTATGA | A (16 31 35) | |
| 144 | MB | X$_2$-arm$_1$-CAACTGAYCTMYACTGTTATGA-arm$_2$-X$_3$ | A (16 31 35) | |
| 145 | PO | GAAMCAACTGACCTAYWCTGCTAT | A (33 52 58) | |
| 146 | MB | X$_2$-arm$_1$-GAAMCAACTGACCTAYWCTGCTAT-arm$_2$-X$_3$ | A (33 52 58) | |
| 147 | PO | AAGACATTATTCAGACTC | C (18 45 39) | |
| 148 | MB | X$_2$-arm$_1$-AAGACATTATTCAGACTC-arm$_2$-X$_3$ | C (18 45 39) | |

TABLE 2

L1-specific sequences for inclusion in NASBA/PCR primers and probes

| SEQ ID | Primer/probe type | Sequence |
|---|---|---|
| 149 | P2/PCR | AATGGCATTTGTTGGGGTAA |
| 150 | P1/PCR | X$_1$-TCATATTCCTCCCCATGTC |
| 151 | PO | TTGTTACTGTTGTTGATACTAC |
| 152 | P2/PCR | AATGGCATTTGTTGGSRHAA |
| 153 | P1/PCR | X$_1$-TCATATTCCTCMMCATGDC |
| 154 | PO | TTGTTACTGTTGTTGATACYAC |
| 155 | PO | TTGTTACTGTTGTTGATACCAC |
| 156 | P2/PCR | AATGGCATTTGTTGGSIIAA |
| 157 | P2/PCR | AATGGCATTTGTTGGIIHAA |
| 158 | P2/PCR | AATGGCATTTGTTGGIRIAA |
| 159 | P2/PCR | AATGGCATTTGTTGGGGTAA |
| 160 | P2/PCR | AATGGCATTTGTTGGGGAAA |
| 161 | P2/PCR | AATGGCATTTGTTGGCATAA |
| 162 | P2/PCR | AATGGCATTTGTTGGGGCAA |
| 163 | P2/PCR | AATGGCATTTGTTGGCACAA |
| 164 | P1/PCR | X$_1$-TCATATTCCTCMICATGIC |
| 165 | P1/PCR | X$_1$-TCATATTCCTCAACATGIC |
| 166 | P1/PCR | X$_1$-TCATATTCCTCIICATGTC |
| 167 | P1/PCR | X$_1$-TCATATTCCTCIICATGGC |
| 168 | P1/PCR | X$_1$-TCATATTCCTCIICATGAC 3' |
| 169 | P1/PCR | X$_1$-TCATATTCCTCIICATGCC 3' |

Preferred primers suitable for use in detection of HPV L1 and E6 mRNA by NASBA are listed in the following tables. However, these are merely illustrative and it is not intended that the scope of the invention should be limited to these specific molecules.

In the following Tables the NASBA P2 primers (p2) include the sequence GATGCAAGGTCGCATATGAG (SEQ ID No. 170) at the 5' end; the NASBA P1 primers (p1) include the sequence AATTCTAATACGACTCACTATAGG-GAGAAGG (SEQ ID No. 172) at the 5' end. Oligonucleotides suitable for use as probes are identified by "po". The P2 primers generally contain HPV sequences from the positive strand, whereas the P1 primers generally contain HPV sequences from the negative strand. nt-refers to nucleotide position in the relevant HPV genomic sequence.

TABLE 3

Preferred E6 NASBA primers and probes

| Primer name | Sequence | HPV Type | nt |
|---|---|---|---|
| HAe6701p2 (SEQ ID 173) | GATGCAAGGTCGCATATGAGCCACAGGAGCGACCC AGAAAGTTA | 16 | 116 |
| HAe6701p1 (SEQ ID 174) | AATTCTAATACGACTCACTATAGGGAGAAGGACGG TTTGTTGTATTGCTGTTC | 16 | 368 |
| HAe6702p2 (SEQ ID 175) | GATGCAAGGTCGCATATGAGCCACAGGAGCGACCC AGAAA | 16 | 116 |
| HAe6702p1 (SEQ ID 176) | AATTCTAATACGACTCACTATAGGGAGAAGGGGTT TGTTGTATTGCTGTTC | 16 | 368 |
| HPV16p1 (SEQ ID 177) | AATTCTAATACGACTCACTATAGGGAGAAGGATTC CCATCTCTATATACTA | 16 | 258 |
| HAe6702Ap1 (SEQ ID 178) | AATTCTAATACGACTCACTATAGGGAGAAGGTCA CGTCGCAGTAACTGT | 16 | 208 |
| HAe6702Bp1 (SEQ ID 179) | AATTCTAATACGACTCACTATAGGGAGAAGGTTG CTTGCAGTACACACA | 16 | 191 |
| HAe6702Cp1 (SEQ ID 180) | AATTCTAATACGACTCACTATAGGGAGAAGGTGC AGIACACACATTCTA | 16 | 186 |
| HAe6702Dp1 (SEQ ID 181) | AATTCTAATACGACTCACTATAGGGAGAAGGGCA GTACACACATTCTAA | 16 | 185 |
| H16e6702Ap2 (SEQ ID 182) | GATGCAAGGTCGCATATGAGACAGTTATGCACAGA GCT | 16 | 142 |
| H16e6702Bp2 (SEQ ID 183) | GATGCAAGGTCGCATATGAGATATTAGAATGTGTG TAC | 16 | 182 |
| H16e6702Cp2 (SEQ ID 184) | GATGCAAGGTCGCATATGAGTTAGAATGTGTGTAC TGC | 16 | 185 |
| H16e6702Dp2 (SEQ ID 185) | GATGCAAGGTCGCATATGAGGAATGTGTGTACTGC AAG | 16 | 188 |
| H16e6702Apo (SEQ ID 10) | ACAGTTATGCACAGAGCT | 16 | 142 |
| H16e6702Bpo (SEQ ID 11) | ATATTAGAATGTGTGTAC | 16 | 182 |
| H16e6702Cpo (SEQ ID 12) | TTAGAATGTGTGTACTGC | 16 | 185 |
| H16e6702Dpo (SEQ ID 13) | GAATGTGTGTACTGCAAG | 16 | 188 |
| HAe6701po (SEQ ID 18) | CTTTGCTTTTCGGGATTTATGC | 16 | 235 |
| HAe6702po (SEQ ID 19) | TATGACTTTGCTTTTCGGGA | 16 | 230 |
| HAe6702mb1 (SEQ ID 186) | $X_2$-cgcatgTATGACTTTGCTTTTCGGGAcatgcg-$X_3$ | 16 | 230 |
| HAe6702mb2 (SEQ ID 187) | $X_2$-ccagctTATGACTTTGCTTTTCGGGAagctgg-$X_3$ | 16 | 230 |
| HAe6702mb3 (SEQ ID 188) | $X_2$-cacgcTATGACTTTGCTTTTCGGGAgcgtg-$X_3$ | 16 | 230 |
| H16e6702mb4 (SEQ ID 189) | $X_2$-cgatcgTATGACTTTGCTTTTCGGGAcgatcg-$X_3$ | 16 | 230 |
| HAe6703p2 (SEQ ID 190) | GATGCAAGGTCGCATATGAGCAGAGGAGGAGGATG AAATAGTA | 16 | 656 |
| HAe6703p1 (SEQ ID 191) | AATTCTAATACGACTCACTATAGGGAGAAGGGCAC AACCGAAGCGTAGAGTCACAC | 16 | 741 |

TABLE 3-continued

Preferred E6 NASBA primers and probes

| Primer name | Sequence | HPV Type | nt |
|---|---|---|---|
| HAe6703po (SEQ ID 23) | TGGACAAGCAGAACCGGACAGAGC | 16 | 687 |
| HAe6704p2 (SEQ ID 192) | GATGCAAGGTCGCATATGAGCAGAGGAGGAGGATG AAATAGA | 16 | 656 |
| HAe6704p1 (SEQ ID 193) | AATTCTAATACGACTCACTATAGGGAGAAGGGCAC AACCGAAGCGTAGAGTCA | 16 | 741 |
| HAe6704po (SEQ ID 26) | AGCAGAACCGGACAGAGCCCATTA | 16 | 693 |
| H18e6701p2 (SEQ ID 194) | GATGCAAGGTCGCATATGAGACGATGAAATAGATG GAGTT | 18 | 702 |
| H18e6701p1 (SEQ ID 195) | AATTCTAATACGACTCACTATAGGGAGAAGGCACG GACACACAAAGGACAG | 18 | 869 |
| H18e6701po (SEQ ID 29) | AGCCGAACCACAACGTCACA | 18 | 748 |
| H18e6702p2 (SEQ ID 196) | GATGCAAGGTCGCATATGAGGAAAACGATGAAATA GATGGAG | 18 | 698 |
| H18e6702p1 (SEQ ID 197) | AATTCTAATACGACTCACTATAGGGAGAAGGACAC CACGGACACACAAAGGACAG | 18 | 869 |
| H18e6702po (SEQ ID 32) | GAACCACAACGTCACACAATG | 18 | 752 |
| H18e6702mb1 (SEQ ID 198) | X$_2$-cgcatgGAACCACAACGTCACACAATGcatgcg-X$_3$ | 18 | 752 |
| H18e6702mb2 (SEQ ID 199) | X$_2$-ccgtcgGAACCACAACGTCACACAATGcgacgg-X$_3$ | 18 | 752 |
| H18e6702mb3 (SEQ ID 200) | X$_2$-cggaccGAACCACAACGTCACACAATGggtccg-X$_3$ | 18 | 752 |
| H18e6702mb4 (SEQ ID 201) | X$_2$-cgatcgGAACCACAACGTCACACAATGcgatcg-X$_3$ | 18 | 752 |
| H18e6703p2 (SEQ ID 202) | GATGCAAGGTCGCATATGAGTTCCGGTTGACCTTC TATGT | 18 | 651 |
| H18e6703p1 (SEQ ID 203) | AATTCTAATACGACTCACTATAGGGAGAAGGGGTC GTCTGCTGAGCTTTCT | 18 | 817 |
| H18e6704p2 (SEQ ID 204) | GATGCAAGGTCGCATATGAGGCAAGACATAGAAAT AACCTG | 18 | 179 |
| H18e6704p1 (SEQ ID 205) | AATTCTAATACGACTCACTATAGGGAGAAGGACCC AGTGTTAGTTAGTT | 18 | 379 |
| H18e6704po (SEQ ID 38) | TGCAAGACAGTATTGGAACT | 18 | 207 |
| H31e6701p2 (SEQ ID 206) | GATGCAAGGTCGCATATGAGGGAAATACCCTACGA TGAAC | 31 | 164 |
| H31e6701p1 (SEQ ID 207) | AATTCTAATACGACTCACTATAGGGAGAAGGGGAC ACAACGGTCTTTGACA | 31 | 423 |
| H31e6701po (SEQ ID 41) | ATAGGGACGACACACCACACGGAG | 31 | 268 |
| H31e6702p2 (SEQ ID 208) | GATGCAAGGTCGCATATGAGGGAAATACCCTACGA TGAACTA | 31 | 164 |
| H31e6702p1 (SEQ ID 209) | AATTCTAATACGACTCACTATAGGGAGAAGGCTGG ACACAACGGTCTTTGACA | 31 | 423 |
| H31e6702po (SEQ ID 44) | TAGGGACGACACACCACACGGA | 31 | 269 |

TABLE 3-continued

Preferred E6 NASBA primers and probes

| Primer name | Sequence | HPV Type | nt |
|---|---|---|---|
| H31e6703p2 (SEQ ID 210) | GATGCAAGGTCGCATATGAGACTGACCTCCACTGT TATGA | 31 | 617 |
| H31e6703p1 (SEQ ID 211) | AATTCTAATACGACTCACTATAGGGAGAAGGTATC TACTTGTGTGCTCTGT | 31 | 766 |
| H31e6703po (SEQ ID 47) | GACAAGCAGAACCGGACACATC | 31 | 687 |
| H31e6704p2 (SEQ ID 212) | GATGCAAGGTCGCATATGAGTGACCTCCACTGTTA TGAGCAATT | 31 | 619 |
| H31e6704p1 (SEQ ID 213) | AATTCTAATACGACTCACTATAGGGAGAAGGTGCG AATATCTACTTGTGTGCTCT GT | 31 | 766 |
| H31e6704po (SEQ ID 50) | GGACAAGCAGAACCGGACACATCCAA | 31 | 686 |
| H31e6704mb1 (SEQ ID 214) | $X_2$-ccgaaggGGACAAGCAGAACCGGACACATCC AAccttcgg-$X_3$ | 31 | 686 |
| H31e6704mb2 (SEQ ID 215) | $X_2$-ccgtcgGGACAAGCAGAACCGGACACATCCA Acgacgg-$X_3$ | 31 | 686 |
| H31e6704mb3 (SEQ ID 216) | $X_2$-cacgtcgGGACAAGCAGAACCGGACACATCCAA cgacgtg-$X_3$ | 31 | 686 |
| H31e6704mb4 (SEQ ID 217) | $X_2$-cgcagcGGACAAGCAGAACCGGACACATCCAA gctgcg-$X_3$ | 31 | 686 |
| H31e6704mb5 (SEQ ID 218) | $X_2$-cgatcgGGACAAGCAGAACCGGACACATCCAA cgatcg-$X_3$ | 31 | 686 |
| H31e6705p2 (SEQ ID 219) | GATGCAAGGTCGCATATGAGACTGACCTCCACTGT TAT | 31 | 617 |
| H31e6705p1 (SEQ ID 220) | AATTCTAATACGACTCACTATAGGGAGAAGGCACG ATTCCAAATGAGCCCAT | 31 | 809 |
| H33e6701p2 (SEQ ID 221) | GATGCAAGGTCGCATATGAGTATCCTGAACCAACT GACCTAT | 33 | 618 |
| H33e6701p1 (SEQ ID 222) | AATTCTAATACGACTCACTATAGGGAGAAGGTTGA CACATAAACGAACTG | 33 | 763 |
| H33e6701po (SEQ ID 56) | CAGATGGACAAGCACAACC | 33 | 694 |
| H33e6703p2 (SEQ ID 223) | GATGCAAGGTCGCATATGAGTCCTGAACCAACTGA CCTAT | 33 | 620 |
| H33e6703p1 (SEQ ID 224) | AATTCTAATACGACTCACTATAGGGAGAAGGCCCA TAAGTAGTTGCTGTAT | 33 | 807 |
| H33e6703po (SEQ ID 59) | GGACAAGCACAACCAGCCACAGC | 33 | 699 |
| H33e6703mb1 (SEQ ID 225) | $X_2$-ccaagcGGACAAGCACAACCAGCCACAGCgct tgg-$X_3$ | 33 | 699 |
| H33e6703mb2 (SEQ ID 226) | $X_2$-ccaagcgGGACAAGCACAACCAGCCACAGC cgcttgg-$X_3$ | 33 | 699 |
| H33e6703mb3 (SEQ ID 227) | $X_2$-cccagcGGACAAGCACAACCAGCCACAGCgct ggg-$X_3$ | 33 | 699 |
| H33e6703mb4 (SEQ ID 228) | $X_2$-ccaaagcGGACAAGCACAACCAGCCACAGCg ctttgg-$X_3$ | 33 | 699 |
| H33e6703mb5 (SEQ ID 229) | $X_2$-cctgcGGACAAGCACAACCAGCCACAGCgcagg-$X_3$ | 33 | 699 |
| H33e6703mb6 (SEQ ID 230) | $X_2$-ccgatcgGGACAAGCACAACCAGCCACAGCga tcg-$X_3$ | 33 | 699 |

TABLE 3-continued

Preferred E6 NASBA primers and probes

| Primer name | Sequence | HPV Type | nt |
|---|---|---|---|
| H33e6702p2 (SEQ ID 231) | GATGCAAGGTCGCATATGAGGACCTTTGTGTCCTCAAGAA | 33 | 431 |
| H33e6702p1 (SEQ ID 232) | AATTCTAATACGACTCACTATAGGGAGAAGGAGGTCAGTTGGTTCAGGATA | 33 | 618 |
| H33e6702po (SEQ ID 63) | AGAAACTGCACTGTGACGTGT | 33 | 543 |
| H35e6701p2 (SEQ ID 233) | GATGCAAGGTCGCATATGAGATTACAGCGGAGTGAGGTAT | 35 | 217 |
| H35e6701p1 (SEQ ID 234) | AATTCTAATACGACTCACTATAGGGAGAAGGGTCTTTGCTTTTCAACTGGA | 35 | 442 |
| H35e5601po (SEQ ID 66) | ATAGAGAAGGCCAGCCATAT | 35 | 270 |
| H35e6702p2 (SEQ ID 235) | GATGCAAGGTCGCATATGAGTCAGAGGAGGAGGAAGATACTA | 35 | 655 |
| H35e6702p1 (SEQ ID 236) | AATTCTAATACGACTCACTATAGGGAGAAGGGATTATGCTCTCTGTGAACA | 35 | 844 |
| H35e6703p2 (SEQ ID 237) | GATGCAAGGTCGCATATGAGCCCGAGGCAACTGACCTATA | 35 | 610 |
| H35e6703p1 (SEQ ID 238) | AATTCTAATACGACTCACTATAGGGAGAAGGGTCAATGTGTGTGCTCTGTA | 35 | 770 |
| H35e6702po (SEQ ID 71) | GACAAGCAAAACCAGACACCTCCAA | 35 | 692 |
| H35e6703po (SEQ ID 72) | GACAAGCAAAACCAGACACC | 35 | 692 |
| H52e6701p2 (SEQ ID 239) | GATGCAAGGTCGCATATGAGTTGTGTGAGGTGCTGGAAGAAT | 52 | 144 |
| H52e6701p1 (SEQ ID 240) | AATTCTAATACGACTCACTATAGGGAGAAGGCCCTCTCTTCTAATGTTT | 52 | 358 |
| H52e6701po (SEQ ID 75) | GTGCCTACGCTTTTTATCTA | 52 | 296 |
| H52e6702p2 (SEQ ID 241) | GATGCAAGGTCGCATATGAGGTGCCTACGCTTTTTATCTA | 52 | 296 |
| H52e6702p1 (SEQ ID 242) | AATTCTAATACGACTCACTATAGGGAGAAGGGGGGTCTCCAACACTCTGAACA | 52 | 507 |
| H52e6702po (SEQ ID 78) | TGCAAACAAGCGATTTCA | 52 | 461 |
| H58e6701p2 (SEQ ID 243) | GATGCAAGGTCGCATATGAGTCAGGCGTTGGAGACATC | 58 | 157 |
| H58e6701p1 (SEQ ID 244) | AATTCTAATACGACTCACTATAGGGAGAAGGAGCAATCGTAAGCACACT | 58 | 301 |
| H58e6702p2 (SEQ ID 245) | GATGCAAGGTCGCATATGAGTCTGTGCATGAAATCGAA | 58 | 173 |
| H58e6702p1 (SEQ ID 246) | AATTCTAATACGACTCACTATAGGGAGAAGGAGCACACTTTACATACTG | 58 | 291 |
| H58e6701po (SEQ ID 83) | TGAAATGCGTTGAATGCA | 58 | 192 |
| H58e6702po (SEQ ID 84) | TTGCAGCGATCTGAGGTATATG | 58 | 218 |
| HBe6701p2 (SEQ ID 247) | GATGCAAGGTCGCATATGAGTACACTGCTGGACAACAT | B (11) | 514 |

TABLE 3-continued

Preferred E6 NASBA primers and probes

| Primer name | Sequence | HPV Type | nt |
|---|---|---|---|
| HBe6701p1 (SEQ ID 248) | AATTCTAATACGACTCACTATAGGGAGAAGGTCATCTTCTGAGCTGTCT | B (11) | 619 |
| HBe6702p2 (SEQ ID 249) | GATGCAAGGTCGCATATGAGTACACTGCTGGACAACATGCA | B (11) | 514 |
| HBe6702p1 (SEQ ID 250) | AATTCTAATACGACTCACTATAGGGAGAAGGGTCACATCCACAGCAACAGGTCA | B (11) | 693 |
| HBe6701po (SEQ ID 89) | GTAGGGTTACATTGCTATGA | B (11) | 590 |
| HBe6702po (SEQ ID 90) | GTAGGGTTACATTGCTATGAGC | B (11) | 590 |
| HBe6703p2 (SEQ ID 251) | GATGCAAGGTCGCATATGAGTGACCTGTTGCTGTGGATGTGA | B (11) | 693 |
| HBe6703p1 (SEQ ID 252) | AATTCTAATACGACTCACTATAGGGAGAAGGTACCTGAATCGTCCGCCAT | B (11) | 832 |
| HBe6703po (SEQ ID 93) | ATWGTGTGTCCCATCTGC | B (11) | 794 |
| HCe6701p2 (SEQ ID 253) | GATGCAAGGTCGCATATGAGCATGCCATAAATGTATAGA | C (18 39 45) | 295 |
| HCe6701p1 (SEQ ID 254) | AATTCTAATACGACTCACTATAGGGAGAAGGCACCGCAGGCACCTTATTAA | C (18 39 45) | 408 |
| HCe6701po (SEQ ID 96) | AGAATTAGAGAATTAAGA | C (18 39 45) | 324 |
| H39e6701p2 (SEQ ID 255) | GATGCAAGGTCGCATATGAGGCAGACGACCACTACAGCAAA | 39 | 210 |
| H39e6701p1 (SEQ ID 256) | AATTCTAATACGACTCACTATAGGGAGAAGGACACCGAGTCCGAGTAATA | 39 | 344 |
| H39e6701po (SEQ ID 99) | ATAGGGACGGGGAACCACT | 39 | 273 |
| H39e6702p2 (SEQ ID 257) | GATGCAAGGTCGCATATGAGTATTACTCGGACTCGGTGT | 39 | 344 |
| H39e6702p1 (SEQ ID 258) | AATTCTAATACGACTCACTATAGGGAGAAGGCTTGGGTTTCTCTTCGTGTTA | 39 | 558 |
| H39e6702po (SEQ ID 102) | GGACCACAAAACGGGAGGAC | 39 | 531 |
| H39e6703p2 (SEQ ID 259) | GATGCAAGGTCGCATATGAGGAAATAGATGAACCCGACCA | 39 | 703 |
| H39e6703p1 (SEQ ID 260) | AATTCTAATACGACTCACTATAGGGAGAAGGGCACACCACGGACACACAAA | 39 | 886 |
| H39e6703po (SEQ ID 105) | TAGCCAGACGGGATGAACCACAGC | 39 | 749 |
| HPV45p2 (SEQ ID 261) | GATGCAAGGTCGCATATGAGAACCATTGAACCCAGCAGAAA | 45 | 430 |
| HPV45p1 (SEQ ID 262) | AATTCTAATACGACTCACTATAGGGAGAAGGTCTTTCTTGCCGTGCCTGGTCA | 45 | 527 |
| HPV45po (SEQ ID 108) | GTACCGAGGGCAGTGTAATA | 45 | 500 |
| H45e6701p2 (SEQ ID 263) | GATGCAAGGTCGCATATGAGAACCATTGAACCCAGCAGAAA | 45 | 430 |
| H45e6701p1 (SEQ ID 264) | AATTCTAATACGACTCACTATAGGGAGAAGGTCTTTCTTGCCGTGCCTGGTCA | 45 | 527 |

TABLE 3-continued

Preferred E6 NASBA primers and probes

| Primer name | Sequence | HPV Type | nt |
|---|---|---|---|
| H45e6702p2 (SEQ ID 265) | GATGCAAGGTCGCATATGAGGAAACCATTGAACCCAGCAGAAAA | 45 | 428 |
| H45e6702p1 (SEQ ID 266) | AATTCTAATACGACTCACTATAGGGAGAAGGTTGCTATACTTGTGTTTCCCTACG | 45 | 558 |
| H45e6701po (SEQ ID 113) | GTACCGAGGGCAGTGTAATA | 45 | 500 |
| H45e6702po (SEQ ID 114) | GGACAAACGAAGATTTCACA | 45 | 467 |
| H45e6703p2 (SEQ ID 267) | GATGCAAGGTCGCATATGAGGTTGACCTGTTGTGTTACCAGCAAT | 45 | 656 |
| H45e6703p1 (SEQ ID 268) | AATTCTAATACGACTCACTATAGGGAGAAGGCACCACGGACACACAAAGGACAAG | 45 | 868 |
| H45e6704p2 (SEQ ID 269) | GATGCAAGGTCGCATATGAGCTGTTGACCTGTTGTGTTACGA | 45 | 654 |
| H45e6704p1 (SEQ ID 270) | AATTCTAATACGACTCACTATAGGGAGAAGGCCACGGACACACAAAGGACAAG | 45 | 868 |
| H45e6705p2 (SEQ ID 271) | GATGCAAGGTCGCATATGAGGTTGACCTGTTGTGTTACGA | 45 | 656 |
| H45e6705p1 (SEQ ID 272) | AATTCTAATACGACTCACTATAGGGAGAAGGACGGACACACAAAGGACAAG | 45 | 868 |
| H45e6703po (SEQ ID 121) | GAGTCAGAGGAGGAAAACGATG | 45 | 686 |
| H45e6704po (SEQ ID 122) | AGGAAAACGATGAAGCAGATGGAGT | 45 | 696 |
| H45e6705po (SEQ ID 123) | ACAACTACCAGCCCGACGAGCCGAA | 45 | 730 |
| H51e6701p2 (SEQ ID 273) | GATGCAAGGTCGCATATGAGGGAGGAGGATGAAGTAGATA | 51 | 658 |
| H51e6701p1 (SEQ ID 274) | AATTCTAATACGACTCACTATAGGGAGAAGGGCCCATTAACATCTGCTGTA | 51 | 807 |
| H51e6702p2 (SEQ ID 275) | GATGCAAGGTCGCATATGAGAGAGGAGGAGGATGAAGTAGATA | 51 | 655 |
| H51e6702p1 (SEQ ID 276) | AATTCTAATACGACTCACTATAGGGAGAAGGACGGGCAAACCAGGCTTAGT | 51 | 829 |
| H51e6701po (SEQ ID 128) | GCAGGTGTTCAAGTGTAGTA | 51 | 747 |
| H51e6702po (SEQ ID 129) | TGGCAGTGGAAAGCAGTGGAGACA | 51 | 771 |
| H56e6701p2 (SEQ ID 277) | GATGCAAGGTCGCATATGAGTTGGGGTGCTGGAGACAAACATCT | 56 | 519 |
| H56e6701p1 (SEQ ID 278) | AATTCTAATACGACTCACTATAGGGAGAAGGTTCATCCTCATCCTCATCCTCTGA | 56 | 665 |
| H56e6702p2 (SEQ ID 279) | GATGCAAGGTCGCATATGAGTGGGGTGCTGGAGACAAACATC | 56 | 520 |
| H56e6702p1 (SEQ ID 280) | AATTCTAATACGACTCACTATAGGGAGAAGGCATCCTCATCCTCATCCTCTGA | 56 | 665 |
| H56e6703p2 (SEQ ID 281) | GATGCAAGGTCGCATATGAGTTGGGGTGCTGGAGACAAACAT | 56 | 519 |
| H56e6703p1 (SEQ ID 282) | AATTCTAATACGACTCACTATAGGGAGAAGGCCACAAACTTACACTCACAACA | 56 | 764 |

TABLE 3-continued

Preferred E6 NASBA primers and probes

| Primer name | Sequence | HPV Type | nt |
|---|---|---|---|
| H56e6701po (SEQ ID 136) | AAAGTACCAACGCTGCAAGACGT | 56 | 581 |
| H56e6702po (SEQ ID 137) | AGAACTAACACCTCAAACAGAAAT | 56 | 610 |
| H56e6703po (SEQ ID 138) | AGTACCAACGCTGCAAGACGTT | 56 | 583 |
| H56e6703po1 (SEQ ID 139) | TTGGACAGCTCAGAGGATGAGG | 56 | 656 |
| H56e6704p2 (SEQ ID 283) | GATGCAAGGTCGCATATGAGGATTTTCCTTATGCAGTGTG | 56 | 279 |
| H56e6704p1 (SEQ ID 284) | AATTCTAATACGACTCACTATAGGGAGAAGGGACATCTGTAGCACCTTATT | 56 | 410 |
| H56e6704po (SEQ ID 142) | GACTATTCAGTGTATGGAGC | 56 | 348 |
| HPVAPO1A (SEQ ID 143) | CAACTGAYCTMYACTGTTATGA | A (16 31 35) | |
| HPVApo1Amb1 (SEQ ID 285) | $X_2$-cgcatgCAACTGAYCTMYACTGTTATGAcatgc g-$X_3$ | A (16 31 35) | |
| HPVApo1Amb2 (SEQ ID 286) | $X_2$-ccgtcgCAACTGAYCTMYACTGTTATGAcga cgg-$X_3$ | A (16 31 35) | |
| HPVApo1Amb3 (SEQ ID 287) | $X_2$-ccaccCAACTGAYCTMYACTGTTATGAgg gtgg-$X_3$ | A (16 31 35) | |
| HPVApo1Amb4 (SEQ ID 288) | $X_2$-cgatcgCAACTGAYCTMYACTGTTATGAcga tcg-$X_3$ | A (16 31 35) | |
| HPVAPO4A (SEQ ID 145) | GAAMCAACTGACCTAYWCTGCTAT | A (33 52 58) | |
| HPVAPO4Amb1 (SEQ ID 289) | $X_2$-ccaagcGAAMCAACTGACCTAYWCTGCTATgc ttgg-$X_3$ | A (33 52 58) | |
| HPVAPO4Amb2 (SEQ ID 290) | $X_2$-ccaagccGAAMCAACTGACCTAYWCTGCTAT ggcttgg-$X_3$ | A (33 52 58) | |
| HPVAPO4Amb3 (SEQ ID 291) | $X_2$-ccaagcgGAAMCAACTGACCTAYWCTGCTA Tcgcttgg-$X_3$ | A (33 52 58) | |
| HPVAPO4Amb4 (SEQ ID 292) | $X_2$-ccagcgGAAMCAACTGACCTAYWCTGCTATcg ctgg-$X_3$ | A (33 52 58) | |
| HPVAPO4Amb5 (SEQ ID 293) | $X_2$-cgatcgGAAMCAACTGACCTAYWCTGCTATcg atcg-$X_3$ | A (33 52 58) | |
| HPVCPO4 (SEQ ID 147) | AAGACATTATTCAGACTC | C (18 45 39) | |
| HPVCPO4Amb1 (SEQ ID 294) | $X_2$-ccaagcAAGACATTATTCAGACTCgcttgg-$X_3$ | C (18 45 39) | |
| HPVCPO4Amb2 (SEQ ID 295) | $X_2$-cgcatgAAGACATTATTCAGACTCcatgcg-$X_3$ | C (18 45 39) | |
| HPVCPO4Amb3 (SEQ ID 296) | $X_2$-cccagcAAGACATTATTCAGACTCgctggg-$X_3$ | C (18 45 39) | |
| HPVCPO4Amb4 (SEQ ID 297) | $X_2$-cgatcgAAGACATTATTCAGACTCcgatcg-$X_3$ | C (18 45 39) | |

Pairs of P1 and P2 primers having the same prefix (e.g. HAe6701p1 and HAe6701p2) are intended to be used in combination. However, other combinations may also be used, as summarised below for HPV types 16, 18, 31, 33 and 45.

Suitable primer-pairs for amplification of HPV 16 E6 mRNA are as follows:

HAe6701p2 or HAe6702p2 (both nt 116) with HAe6701p1 or HAe6702p1 (both nt 368).

HAe6701p2 or HAe6702p2 (both nt 116) with HPV16p1(nt 258).

H16e6702Ap2 (nt 142), H16e6702 Bp2 (nt 182), H16e6702 Cp2 (nt 185) or H16e6702Dp2 (nt 188) with HAe6701p1 or HAe6702p1 (both nt 368).

HAe6701p2 or HAe6702p2 (both nt 116) with HAe6702Ap1 (nt 208), HAe6702 Bp1 (nt 191), HAe6702 Cp1 (nt 186) or HAe6702Dp1 (185). These combinations are suitable for amplification of all E6 splice variants.

HAe6703p2 or HAe6704p2 (both nt 656) with HAe6703p1 or HAe6704p1 (both nt 741). These combinations are suitable for amplification of all transcripts containing the E7 coding region (at least up to nt 741).

The following primer-pairs are preferred for amplification of HPV 18 E6 mRNA:

H18e6701p2 (nt 702) or H18e6702p2 (nt 698) with H18e6701p1 or H18e6702p1 (both nt 869).

H18e6703p2 (nt 651) with H18e6703p1 (nt 817).

H18e6704p2 (nt 179) with H18e6704p1 (nt 379).

The following primer-pairs are preferred for amplification of HPV 31 E6 mRNA:

H31e6701p2 or H31e6702p2 (both nt 164) with H31e6701p1 or H31e6702p1 (both nt 423).

H31e6703p2 (nt 617), H31e6704p2 (nt 619) or H31e6705p2 (nt 617) with H31e6703p1 (nt 766), H31e6704p1 (766) or H31e6705p1 (nt 809).

The following primer-pairs are preferred for amplification of HPV 33 E6 mRNA:

H33e6701p2 (nt 618) or H33e6703p2 (nt 620) with H33e6701p1 (nt 763) or H33e6703p1 (nt 807).

H33e6702p2 (nt 431) with H33e6702p1 (nt 618).

The following primer pair is preferred for amplification of HPV 45:

HPV45p2 (nt 430) with HPV45p1(nt 527)

TABLE 4

E6 PCR primers

| Primer name | | Sequence | HPV type | nt |
|---|---|---|---|---|
| HAe6701PCR2 | (SEQ ID 1) | CCACAGGAGCGACCCAGAAAGTTA | 16 | 116 |
| HAe6701PCR1 | (SEQ ID 2) | ACGGTTTGTTGTATTGCTGTTC | 16 | 368 |
| HAe6702PCR2 | (SEQ ID 3) | CCACAGGAGCGACCCAGAAA | 16 | 116 |
| HAe6702PCR1 | (SEQ ID 4) | GGTTTGTTGTATTGCTGTTC | 16 | 368 |
| HAe6703PCR2 | (SEQ ID 21) | CAGAGGAGGAGGATGAAATAGTA | 16 | 656 |
| HAe6703PCR1 | (SEQ ID 22) | GCACAACCGAAGCGTAGAGTCACAC | 16 | 741 |
| HAe6704PCR2 | (SEQ ID 24) | CAGAGGAGGAGGATGAAATAGA | 16 | 656 |
| HAe6704PCR1 | (SEQ ID 25) | GCACAACCGAAGCGTAGAGTCA | 16 | 741 |
| H18e6701PCR2 | (SEQ ID 27) | ACGATGAAATAGATGGAGTT | 18 | 702 |
| H18e6701PCR1 | (SEQ ID 28) | CACGGACACACAAAGGACAG | 18 | 869 |
| H18e6702PCR2 | (SEQ ID 30) | GAAAACGATGAAATAGATGGAG | 18 | 698 |
| H18e6702PCR1 | (SEQ ID 31) | ACACCACGGACACACAAAGGACAG | 18 | 869 |
| H18e6703PCR2 | (SEQ ID 34) | TTCCGGTTGACCTTCTATGT | 18 | 651 |
| H18e6703PCR1 | (SEQ ID 35) | GGTCGTCTGCTGAGCTTTCT | 18 | 817 |
| H18e6704PCR2 | (SEQ ID 36) | GCAAGACATAGAAATAACCTG | 18 | 179 |
| H18e6704PCR1 | (SEQ ID 37) | ACCCAGTGTTAGTTAGTT | 18 | 379 |
| H31e6701PCR2 | (SEQ ID 39) | GGAAATACCCTACGATGAAC | 31 | 164 |
| H31e6701PCR1 | (SEQ ID 40) | GGACACAACGGTCTTTGACA | 31 | 423 |
| H31e6702PCR2 | (SEQ ID 42) | GGAAATACCCTACGATGAACTA | 31 | 164 |
| H31e6702PCR1 | (SEQ ID 43) | CTGGACACAACGGTCTTTGACA | 31 | 423 |
| H31e6703PCR2 | (SEQ ID 45) | ACTGACCTCCACTGTTATGA | 31 | 617 |
| H31e6703PCR1 | (SEQ ID 46) | TATCTACTTGTGTGCTCTGT | 31 | 766 |
| H31e6704PCR2 | (SEQ ID 48) | TGACCTCCACTGTTATGAGCAATT | 31 | 619 |
| H31e6704PCR1 | (SEQ ID 49) | TGCGAATATCTACTTGTGTGCTCTGT | 31 | 766 |
| H31e6705PCR2 | (SEQ ID 52) | ACTGACCTCCACTGTTAT | 31 | 617 |
| H31e6705PCR1 | (SEQ ID 53) | CACGATTCCAAATGAGCCCAT | 31 | 809 |
| H33e6701PCR2 | (SEQ ID 54) | TATCCTGAACCAACTGACCTAT | 33 | 618 |

TABLE 4-continued

E6 PCR primers

| Primer name | Sequence | HPV type | nt |
|---|---|---|---|
| H33e6701PCR1 (SEQ ID 55) | TTGACACATAAACGAACTG | 33 | 763 |
| H33e6703PCR2 (SEQ ID 57) | TCCTGAACCAACTGACCTAT | 33 | 620 |
| H33e6703PCR1 (SEQ ID 58) | CCCATAAGTAGTTGCTGTAT | 33 | 807 |
| H33e6702PCR2 (SEQ ID 61) | GACCTTTGTGTCCTCAAGAA | 33 | 431 |
| H33e6702PCR1 (SEQ ID 62) | AGGICAGTIGGITCAGGATA | 33 | 618 |
| H35e6701PCR2 (SEQ ID 64) | ATTACAGCGGAGTGAGGTAT | 35 | 217 |
| H35e6701PCR1 (SEQ ID 65) | GTCTTTGCTTTTCAACTGGA | 35 | 442 |
| H35e6702PCR2 (SEQ ID 67) | TCAGAGGAGGAGGAAGATACTA | 35 | 655 |
| H35e6702PCR1 (SEQ ID 68) | GATTATGCTCTCTGTGAACA | 35 | 844 |
| H35e6703PCR2 (SEQ ID 69) | CCCGAGGCAACTGACCTATA | 35 | 610 |
| H35e6703PCR1 (SEQ ID 70) | GTCAATGTGTGTGCTCTGTA | 35 | 770 |
| H52e6701PCR2 (SEQ ID 73) | TTGTGTGAGGTGCTGGAAGAAT | 52 | 144 |
| H52e6701PCR1 (SEQ ID 74) | CCCTCTCTTCTAATGTTT | 52 | 358 |
| H52e6702PCR2 (SEQ ID 75) | GTGCCTACGCTTTTTATCTA | 52 | 296 |
| H52e6702PCR1 (SEQ ID 77) | GGGGTCTCCAACACTCTGAACA | 52 | 507 |
| H58e6701PCR2 (SEQ ID 79) | TCAGGCGTTGGAGACATC | 58 | 157 |
| H58e6701PCR1 (SEQ ID 80) | AGCAATCGTAAGCACACT | 58 | 301 |
| H58e6702PCR2 (SEQ ID 81) | TCTGTGCATGAAATCGAA | 58 | 173 |
| H58e6702PCR1 (SEQ ID 82) | AGCACACTTTACATACTG | 58 | 291 |
| HBe6701PCR2 (SEQ ID 85) | TACACTGCTGGACAACAT | B (11) | 514 |
| HBe6701PCR1 (SEQ ID 86) | TCATCTTCTGAGCTGTCT | B (11) | 619 |
| HBe6702PCR2 (SEQ ID 87) | TACACTGCTGGACAACATGCA | B (11) | 514 |
| HBe6702PCR1 (SEQ ID 88) | GTCACATCCACAGCAACAGGTCA | B (11) | 693 |
| HBe6703PCR2 (SEQ ID 91) | TGACCTGTTGCTGTGGATGTGA | B (11) | 693 |
| HBe6703PCR1 (SEQ ID 92) | TACCTGAATCGTCCGCCAT | B (11) | 832 |
| HCe6701PCR2 (SEQ ID 94) | CATGCCATAAATGTATAGA | C (18 39 45) | 295 |
| HCe6701PCR1 (SEQ ID 95) | CACCGCAGGCACCTTATTAA | C (18 39 45) | 408 |
| H39e6701PCR2 (SEQ ID 97) | GCAGACGACCACTACAGCAAA | 39 | 210 |
| H39e6701PCR1 (SEQ ID 98) | ACACCGAGTCCGAGTAATA | 39 | 344 |
| H39e6702PCR2 (SEQ ID 100) | TATTACTCGGACTCGGTGT | 39 | 344 |
| H39e6702PCR1 (SEQ ID 101) | CTTGGGTTTCTCTTCGTGTTA | 39 | 558 |
| H39e6703PCR2 (SEQ ID 103) | GAAATAGATGAACCCGACCA | 39 | 703 |
| H39e6703PCR1 (SEQ ID 104) | GCACACCACGGACACACAAA | 39 | 886 |
| H45e6701PCR2 (SEQ ID 106) | AACCATTGAACCCAGCAGAAA | 45 | 430 |
| H45e6701PCR1 (SEQ ID 107) | TCTTTCTTGCCGTGCCTGGTCA | 45 | 527 |
| H45e6702PCR2 (SEQ ID 111) | GAAACCATTGAACCCAGCAGAAAA | 45 | 428 |

TABLE 4-continued

E6 PCR primers

| Primer name | Sequence | HPV type | nt |
|---|---|---|---|
| H45e6702PCR1 (SEQ ID 112) | TTGCTATACTTGTGTTTCCCTACG | 45 | 558 |
| H45e6703PCR2 (SEQ ID 115) | GTTGACCTGTTGTGTTACCAGCAAT | 45 | 656 |
| H45e6703PCR1 (SEQ ID 116) | CACCACGGACACACAAAGGACAAG | 45 | 868 |
| H45e6704PCR2 (SEQ ID 117) | CTGTTGACCTGTTGTGTTACGA | 45 | 654 |
| H4Se6704PCR1 (SEQ ID 118) | CCACGGACACACAAAGGACAAG | 45 | 868 |
| H45e6705PCR2 (SEQ ID 119) | GTTGACCTGTTGTGTTACGA | 45 | 656 |
| H45e6705PCR1 (SEQ ID 120) | ACGGACACACAAAGGACAAG | 45 | 868 |
| H51e6701PCR2 (SEQ ID 124) | GGAGGAGGATGAAGTAGATA | 51 | 658 |
| H51e6701PCR1 (SEQ ID 125) | GCCCATTAACATCTGCTGTA | 51 | 807 |
| H51e6702PCR2 (SEQ ID 126) | AGAGGAGGAGGATGAAGTAGATA | 51 | 655 |
| H51e6702PCR1 (SEQ ID 127) | ACGGGCAAACCAGGCTTAGT | 51 | 829 |
| H56e6701PCR2 (SEQ ID 130) | TTGGGGTGCTGGAGACAAACATCT | 56 | 519 |
| H56e6701PCR1 (SEQ ID 131) | TTCATCCTCATCCTCATCCTCTGA | 56 | 665 |
| H56e6702PCR2 (SEQ ID 132) | TGGGGTGCTGGAGACAAACATC | 56 | 520 |
| H56e6702PCR1 (SEQ ID 133) | CATCCTCATCCTCATCCTCTGA | 56 | 665 |
| H56e6703PCR2 (SEQ ID 134) | TTGGGGTGCTGGAGACAAACAT | 56 | 519 |
| H56e6703PCR1 (SEQ ID 135) | CCACAAACTTACACTCACAACA | 56 | 764 |
| H56e6704PCR2 (SEQ ID 140) | GATTTTCCTTATGCAGTGTG | 56 | 279 |
| H56e6704PCR1 (SEQ ID 141) | GACATCTGTAGCACCTTATT | 56 | 410 |

Preferred PCR primer-pairs for HPV types 16, 18, 31 and 33 are analogous to the NASBA primer-pairs.

TABLE 5

Preferred L1 NASBA primers and probes

| Primer name | Sequence |
|---|---|
| Onc2A2 (SEQ ID 298) | 5' GATGCAAGGTCGCATATGAGAATGGCATTTGTTG GGGTAA 3' |
| Onc2A1 (SEQ ID 299) | 5' AATTCTAATACGACTCACTATAGGGAGAAGGTCA TATTCCTCCCCATGTC 3' |
| Onc2PoA (SEQ ID 151) | 5' TTGTTACTGTTGTTGATACTAC 3' |
| Onc2B2 (SEQ ID 300) | 5' GATGCAAGGTCGCATATGAGAATGGCATTTGTTG GSRHAA 3' |
| Onc2B1 (SEQ ID 301) | 5' AATTCTAATACGACTCACTATAGGGAGAAGGTCA TATTCCTCMMCATGDC 3' |
| Onc2PoB (SEQ ID 154) | 5' TTGTTACTGTTGTTGATACYAC 3' |
| Onc2PoC (SEQ ID 155) | 5' TTGTTACTGTTGTTGATACCAC 3' |
| Onc2C2 (SEQ ID 302) | 5' GATGCAAGGTCGCATATGAGAATGGCATTTGTTG GSIIAA 3' |
| Onc2D2 (SEQ ID 303) | 5' GATGCAAGGTCGCATATGAGAATGGCATTTGTTG GIIHAA 3' |
| Onc2E2 (SEQ ID 304) | 5' GATGCAAGGTCGCATATGAGAATGGCATTTGTTG GIRIAA 3' |
| Onc2F2 (SEQ ID 305) | 5' GATGCAAGGTCGCATATGAGAATGGCATTTGTTG GGGTAA 3' |
| Onc2G2 (SEQ ID 306) | 5' GATGCAAGGTCGCATATGAGAATGGCATTTGTTG GGGAAA 3' |
| Onc2H2 (SEQ ID 307) | 5' GATGCAAGGTCGCATATGAGAATGGCATTTGTTG GCATAA 3' |
| Onc2I2 (SEQ ID 308) | 5' GATGCAAGGTCGCATATGAGAATGGCATTTGTTG GGGCAA 3' |
| Onc2J2 (SEQ ID 309) | 5' GATGCAAGGTCGCATATGAGAATGGCATTTGTTG GCACAA 3' |
| Onc2K1 (SEQ ID 310) | 5' AATTCTAATACGACTCACTATAGGGAGAAGGTCA TATTCCTCMICATGIC 3' |
| Onc2L1 (SEQ ID 311) | 5' AATTCTAATACGACTCACTATAGGGAGAAGGTCA TATTCCTCAACATGIC 3' |

TABLE 5-continued

Preferred L1 NASBA primers and probes

| Primer name | Sequence |
|---|---|
| Onc2M1 (SEQ ID 312) | 5' AATTCTAATACGACTCACTATAGGGAGAAGGTCA TATTCCTCIICATGTC 3' |
| Onc2N1 (SEQ ID 313) | 5' AATTCTAATACGACTCACTATAGGGAGAAGGTCA TATTCCTCIICATGGC 3' |
| Onc2O1 (SEQ ID 314) | 5' AATTCTAATACGACTCACTATAGGGAGAAGGTCA TATTCCTCIICATGAC 3' |
| Onc2P1 (SEQ ID 315) | 5' AATTCTAATACGACTCACTATAGGGAGAAGGTCA TATTCCTCIICATGCC 3' |

TABLE 6

Preferred L1 PCR primers

| Primer name | Sequence |
|---|---|
| Onc2A1-PCR (SEQ ID 149) | 5' AATGGCATTTGTTGGGGTAA 3' |
| Onc2A2-PCR (SEQ ID 150) | 5' TCATATTCCTCCCCATGTC 3' |
| Onc2B1-PCR (SEQ ID 152) | 5' AATGGCATTTGTTGGSRHAA 3' |
| Onc2B2-PCR (SEQ ID 153) | 5' TCATATTCCTCMMCATGDC 3' |
| Onc2C1-PCR (SEQ ID 156) | 5' AATGGCATTTGTTGGSIIAA 3' |
| Onc2D1-PCR (SEQ ID 157) | 5' AATGGCATTTGTTGGIIHAA 3' |
| Onc2E1-PCR (SEQ ID 158) | 5' AATGGCATTTGTTGGIRIAA 3' |
| Onc2F1-PCR (SEQ ID 159) | 5' AATGGCATTTGTTGGGGTAA 3' |
| Onc2G1-PCR (SEQ ID 160) | 5' AATGGCATTTGTTGGGGAAA 3' |
| Onc2H1-PCR (SEQ ID 161) | 5' AATGGCATTTGTTGGCATAA 3' |
| Onc2I1-PCR (SEQ ID 162) | 5' AATGGCATTTGTTGGGGCAA 3' |
| Onc2J1-PCR (SEQ ID 163) | 5' AATGGCATTTGTTGGCACAA 3' |
| Onc2K2-PCR (SEQ ID 164) | 5' TCATATTCCTCMICATGIC 3' |
| Onc2L2-PCR (SEQ ID 165) | 5' TCATATTCCTCAACATGIC 3' |
| Onc2M2-PCR (SEQ ID 166) | 5' TCATATTCCTCIICATGTC 3' |
| Onc2N2-PCR (SEQ ID 167) | 5' TCATATTCCTCIICATGGC 3' |
| Onc2O2-PCR (SEQ ID 168) | 5' TCATATTCCTCIICATGAC 3' |
| Onc2P2-PCR (SEQ ID 169) | 5' TCATATTCCTCIICATGCC 3' |

The HPV-specific sequences in SEQ ID NOs:149 and 150 (primers Onc2A2/Onc2A1-PCR and Onc2A1/Onc2A2-PCR) are identical to fragments of the HPV type 16 genomic sequence from position 6596-6615 (SEQ ID NO:149; Onc2A2/Onc2A1-PCR), and from position 6729 to 6747(SEQ ID NO:150; Onc2A1/Onc2A2-PCR).

The HPV-specific sequences SEQ ID NOs:152 and 153 (Onc2B2/Onc2B1-PCR and Onc2B1/Onc2B2-PCR) are variants of the above sequences, respectively, including several degenerate bases. Representations of the sequences of degenerate oligonucleotide molecules provided herein use the standard IUB code for mixed base sites: N=G, A, T, C; V=G, A, C; B=G, T, C; H=A, T, C; D=G, A, T; K=G, T; S=G, C; W=A, T; M=A, C; Y=C, T; R=A, G.

It is also possible to use variants of the HPV-specific sequences SEQ ID NO:152 (Onc2B2/Onc2B1-PCR) and SEQ ID NO:153 (Onc2B1/Onc2B2-PCR) wherein any two of nucleotides "SRH" towards the 3' end of the sequence are replaced with inosine (I), as follows:

| | |
|---|---|
| 5' AATGGCATTTGTTGGIIHAA 3' | (SEQ ID 157) |
| 5' AATGGCATTTGTTGGSIIAA 3' | (SEQ ID 156) |
| 5' AATGGCATTTGTTGGIRIAA 3' | (SEQ ID 158) |

The HPV-specific sequences SEQ ID NOs: 156-163 (present in primers Onc2C2, Onc2D2, Onc2E2, Onc2F2, Onc2G2, Onc2H2, Onc2I2, Onc2J2, Onc2C1-PCR, Onc2D1-PCR, Onc2E1-PCR, Onc2F1-PCR, Onc2G1-PCR, Onc2H1-PCR, Onc2I1-PCR and Onc2J1-PCR) are variants based on the HPV-specific sequence SEQ ID NO:152 (Onc2B2/Onc2B1-PCR), whereas the HPV-specific sequences SEQ ID NOs: 164-169 (present in primers Onc2K1, Onc2L1, Onc2M1, Onc2N1, Onc2O1, Onc2P1, Onc2K2-PCR, Onc2L2-PCR, Onc2M2-PCR, Onc2N2-PCR, Onc2O2-PCR and Onc2P2-PCR are variants based on the HPV-specific sequence SEQ ID NO:153 (Onc2B1/Onc2B2-PCR). These variants include degenerate bases and also inosine (I) residues. This sequence variation enables oligonucleotides incorporating the variant sequences to bind to multiple HPV types. Inosine bases do not interfere with hybridization and so may be included at sites of variation between HPV types in order to construct a "consensus" primer able to bind to multiple HPV types.

Any one or more of primers Onc2A2, Onc2B2, Onc2C2, Onc2D2, Onc2E2, Onc2F2, Onc2G2, Onc2H2, Onc2I2 and Onc2J2, may be used in combination with any one or more of primers Onc2A1, Onc2B1, Onc2K1, Onc2L1, Onc2M1, Onc2N1, Onc2O1 and Onc2P1, for NASBA amplification of HPV L1 mRNA.

Any one or more of primers Onc2A1-PCR, Onc2B1-PCR, Onc2C1-PCR, Onc2D1-PCR, Onc2E1-PCR, Onc2F1-PCR, Onc2G1-PCR, Onc2H1-PCR, Onc2I1-PCR and Onc2J1-PCR, may be used in combination with any one or more of primers Onc2A2-PCR, Onc2B2-PCR, Onc2K2-PCR, Onc2L2-PCR, Onc2M2-PCR, Onc2N2-PCR, Onc2O2-PCR and Onc2P2-PCR for PCR amplification of HPV L1 mRNA.

Figure 1B:
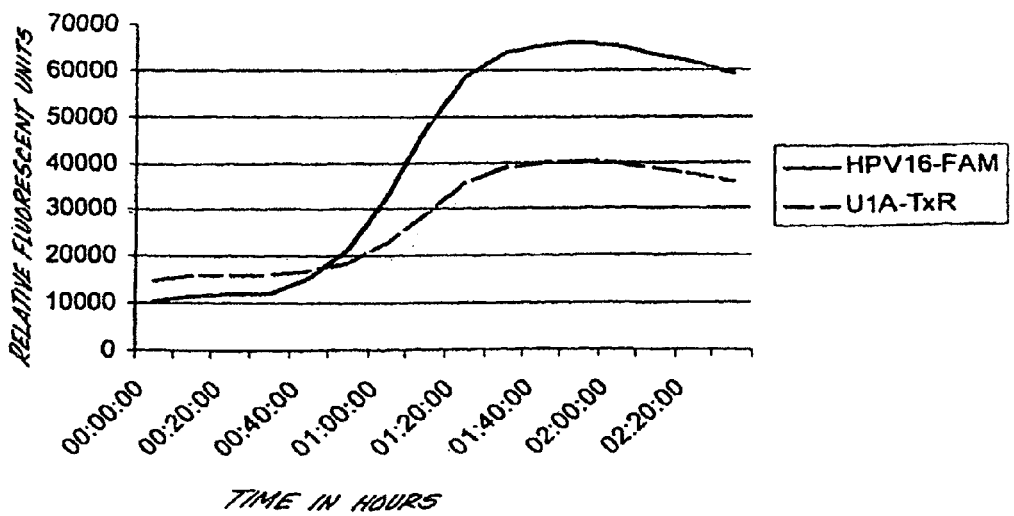
Figure 2A:
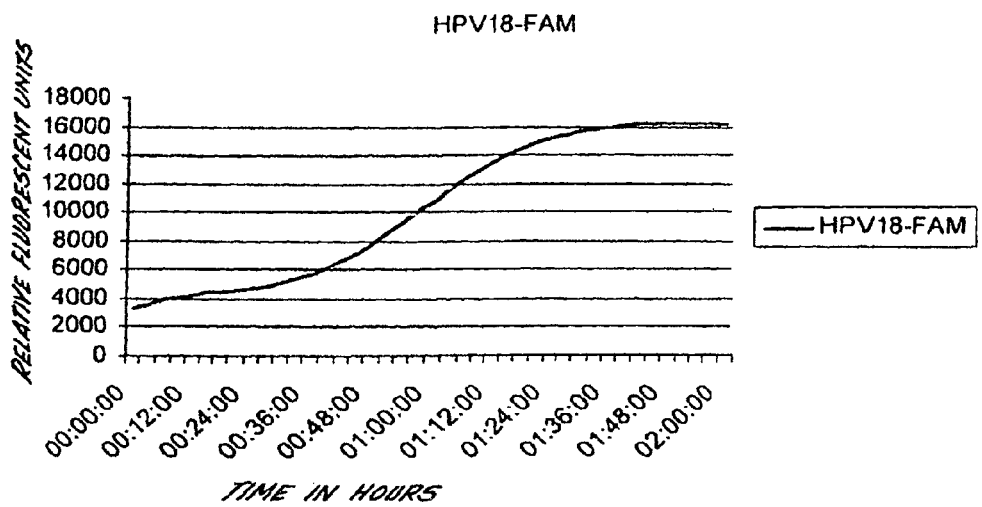
Figure 2B:
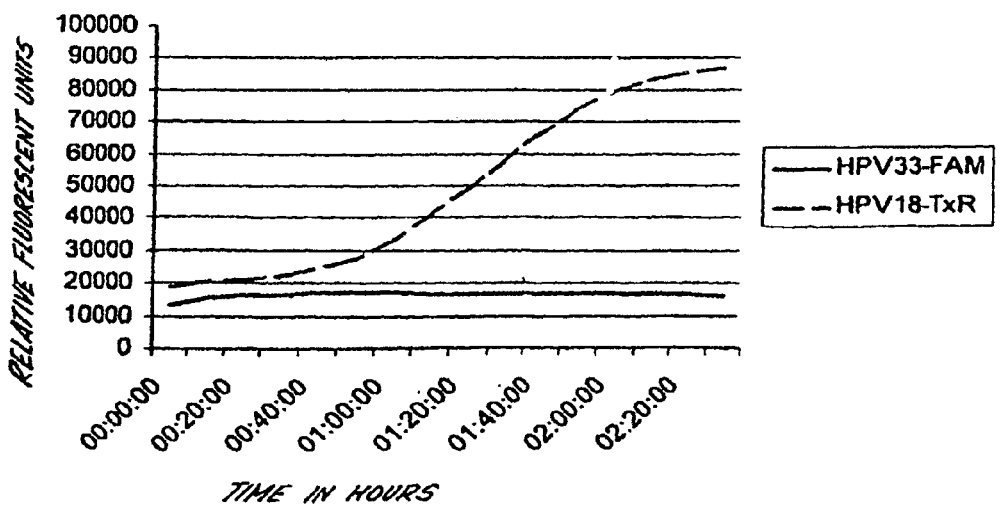
Figure 3A:
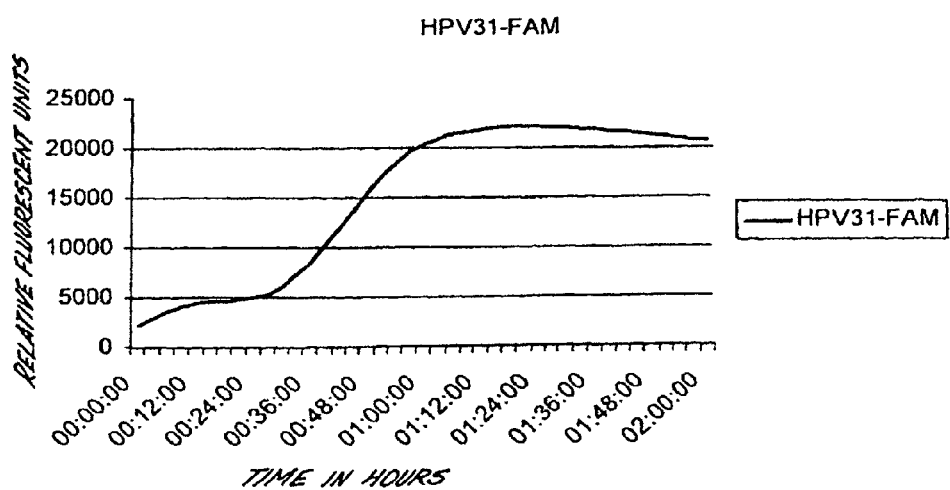
Figure 3B:
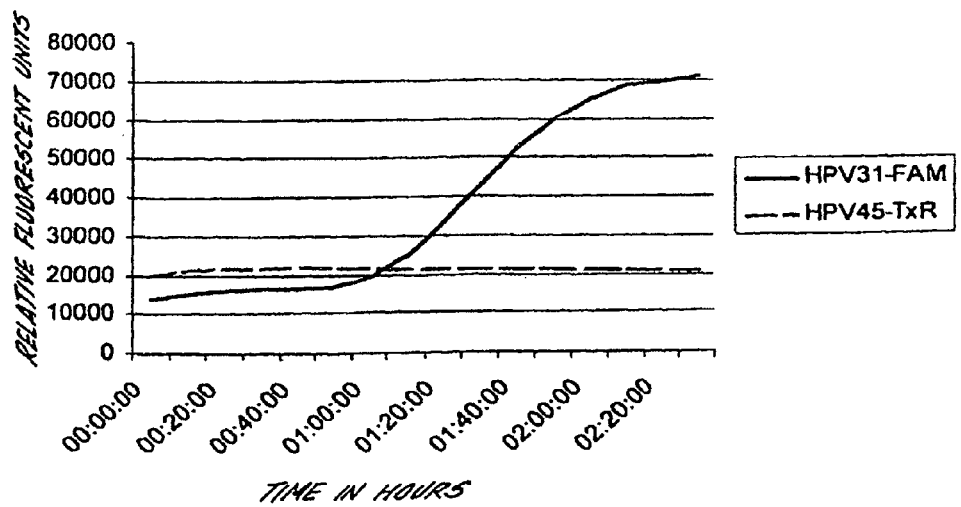
Figure 4A:
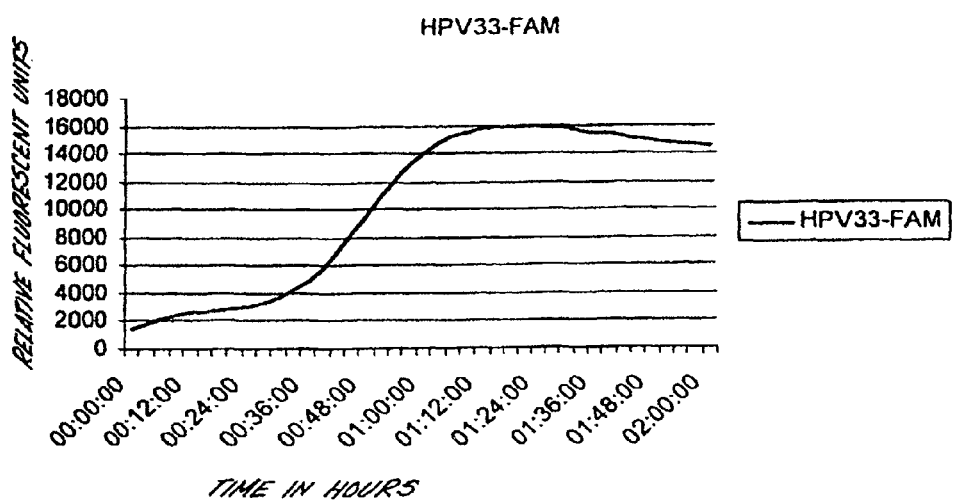
Figure 4B:
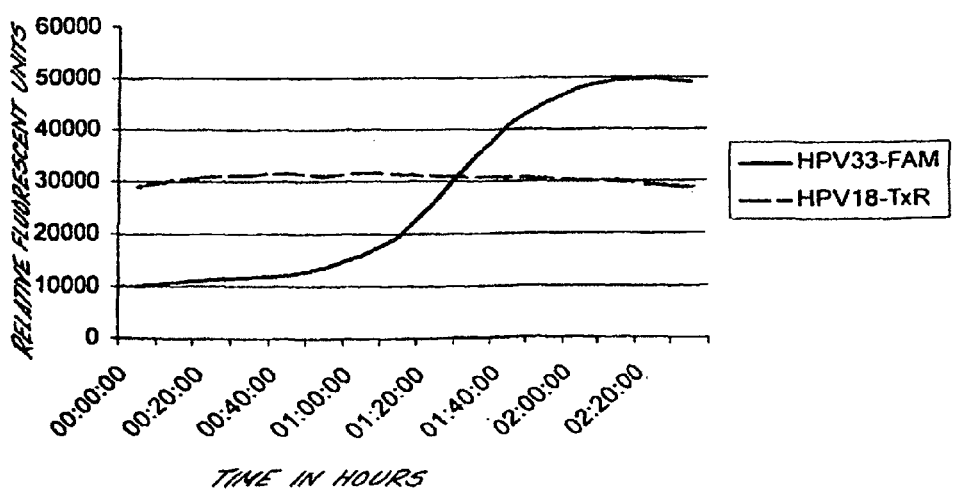
Figure 5A:
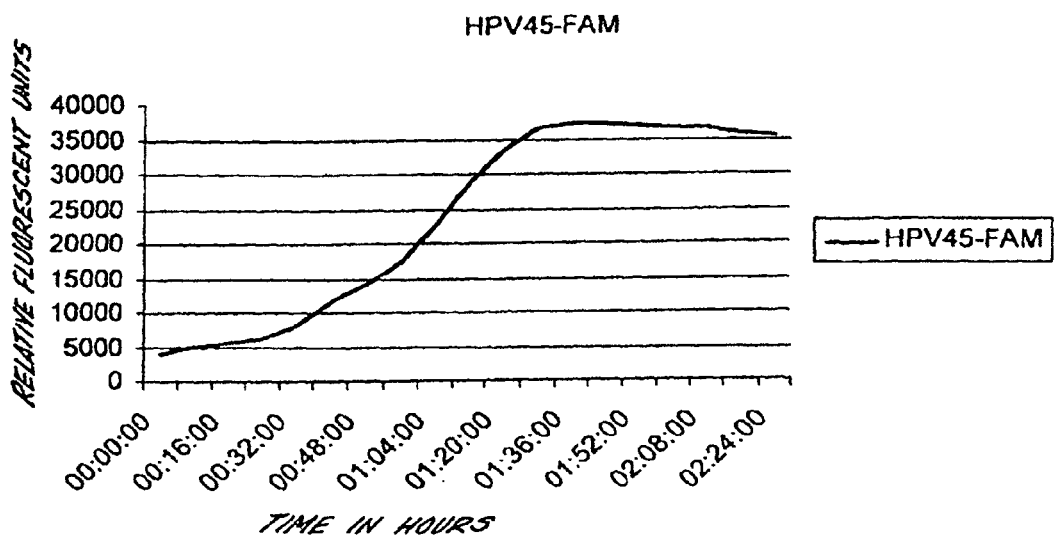
Figure 5B:
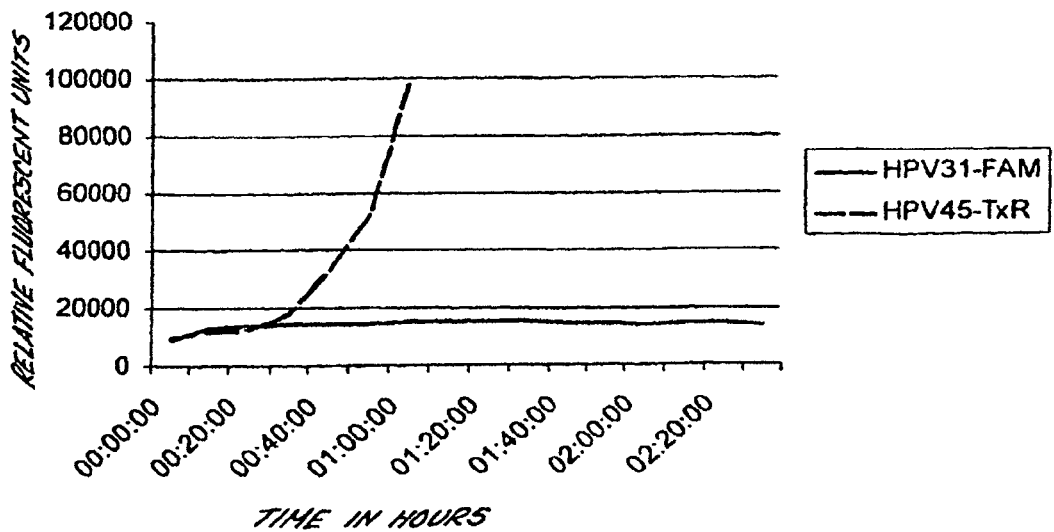
Figure 6:
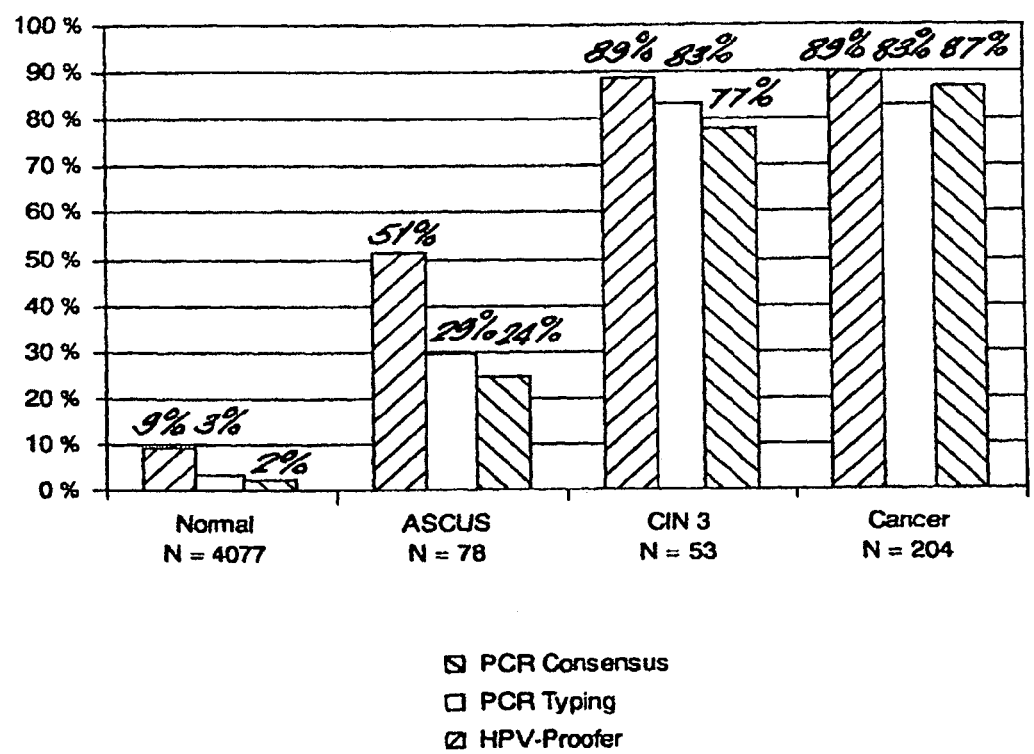

The invention will be further understood with reference to the following experimental examples and figures in which:

FIG. 1A shows the results of a single reaction real-time NASBA assay using a FAM molecular beacon for HPV 16 on a patient sample while FIG. 1B shows multiplexed real-time NASBA assay using the FAM molecular beacon of FIG. 1A and a molecular beacon labeled with Texas red for UIA, FIG. 2A shows single reaction real-time NASBA with FAM molecular beacon for HPV 18 on a patient sample while FIG. 2B shows a multiplexed version with a Texas red labeled molecular beacon for HPV 18 and a FAM labeled beacon for HPV 33, FIG. 3A shows single reaction real-time NASBA with HPV 31 FAM labeled molecular beacon while FIG. 3B shows multiplexed version including HPV 45 Texas red labeled molecular beacon, FIG. 4A shows single reaction real-time NASBA with HPV 33 FAM labeled molecular beacon while FIG. 4B is a multiplexed version including a Texas red labeled HPV 18 molecular beacon, FIG. 5A shows single reaction real-time NASBA with HPV45 FAM labeled molecular beacon while FIG. 5B shows the multiplexed version including HPV 45 Texas red labeled molecular beacon and a FAM labeled HPV 31 molecular beacon, and FIG. 6 shows HPV detected by PreTect HPV-Proofer and PCR compared to cytology or histology.

EXAMPLE 1

Detection of HPV mRNA by NASBA-Based Nucleic Acid Amplification and Real-Time Detection Collection and Preparation of Clinical Samples Pap smears and HPV samples were collected from 5970 women in the cervical screening program in Oslo, Norway. Samples intended for RNA/DNA extraction were treated as follows:

Cervical samples were collected from each women attending the cervical screening program using a cytobrush (Rovers Medical Devices, The Netherlands). The cytobrush was then immersed in 9 ml lysis buffer (5M Guanidine thiocyanate). Since RNA is best protected in the 5M guanidine thiocyanate at −70° C. only 1 ml of the total volume of sample was used for each extraction round. The samples in lysis buffer were stored at −20° C. for no more than one week, then at −70° C. until isolation of DNA/RNA.

RNA and DNA were automatically isolated from 5300 women in the first round of extraction, using 1 ml from the total sample of 9 ml in lysis buffer. RNA and DNA were extracted according to the "Booms" isolation method from Organon Teknika (Organon Teknika B. V., Boselind 15, P.O. Box 84, 5280 AB Baxtel, The Netherlands; now Biomérieux, 69280 Marcy l'Etoile, France) using the Nuclisens™ extractor following the protocol for automated extraction.

Cell Lines

DNA and RNA from HeLa (HPV 18), SiHa (HPV 16) and CaSki (HPV 16) cell lines were used as positive controls for the PCR and NASBA reactions. These cells were also used as sample material in the sensitivity study (Example 2). SiHa cells have integrated 1-2 copies of HPV 16 per cell, whilst CaSki cells have between 60-600 copies of HPV 16, both integrated and in the episomal state. HeLa cells have approximately 10-50 copies of HPV 18 per cell.

HPV Detection and Typing by PCR

Isolated DNA from cervical scrapes was subjected to PCR using the consensus GP5+/6+ primers (EP-B-0 517 704). The PCR was carried out in 50 μl reaction volume containing 75 mM Tris-HCl (pH 8.8 at 25° C.), 20 mM (NH$_4$)$_2$SO$_4$, 0.01% Tween 20™, 200 mM each of dNTP, 1.5 mM MgCl$_2$, 1 U recombinant Taq DNA Polymerase (MBI Fermentas), 3 μl DNA sample and 50 pmol of each GP5+ and GP6+ primers. A 2 minutes denaturation step at 94° C. was followed by 40 cycles of amplification with a PCR processor (Primus 96, HPL block, MWG, Germany). Each cycle included a denaturation step at 1 minutes, a primer annealing step at 40° C. for 2 minutes and a chain elongation step at 72° C. for 1.5 minutes. The final elongation step was prolonged by 4 minutes to ensure a complete extension of the amplified DNA.

The GP5+/6+ positive samples were subjected to HPV type 16, 31 and 33 PCR protocols as follows:

HPV 16, 31 and 33: The PCR was carried out in 50 μl containing 75 mM Tris-HCl (pH 8.8 at 25° C.), 200 mM each of dNTP, 1.5 mM MgCl$_2$, 2.5 U recombinant Taq DNA Polymerase (MBI Fermentas), 3 μl DNA sample and 25 pmol of each primers. A 2 minutes denaturation step at 94° C. was followed by 35 cycles of amplification with a PCR processor (Primus 96, HPL block, MWG, Germany). Each cycle included a denaturation step at 30 sec, a primer annealing step at 57° C. for 30 sec and a chain elongation step at 72° C. for 1 minutes. The final elongation step was prolonged by 10 minutes to ensure a complete extension of the amplified DNA. The protocol for HPV 33 had a primer annealing step at 52° C. HPV 18 protocol:

Primers were designed to identify HPV type 18. The PCR was carried out in 50 μl containing 75 mM Tris-HCl (pH 8.8 at 25° C.), 20 mM (NH$_4$)$_2$SO$_4$, 0.01% Tween 20, 200 mM each of dNTP, 2.0 mM MgCl$_2$, 2.5 U recombinant Taq DNA Polymerase (MBI Fermentas), 3 μl DNA sample and 25 pmol of each primer. A 2 minutes denaturation step at 94° C. was followed by 35 cycles of amplification in a PCR processor (Primus 96, HPL block, MWG, Germany). Each cycle included a denaturation step at 30 sec, a primer annealing step at 57° C. for 30 sec and a chain elongation step at 72° C. for 1 minutes. The final elongation step was prolonged by 10 minutes to ensure a complete extension of the amplified DNA.

A primer set directed against the human □-globin gene was used as a control of the DNA quality (Operating procedure, University Hospital Vrije Universiteit, Amsterdam, The Netherlands). The PCR was carried out in 50 μl containing 75 mM Tris-HCl (pH 8.8 at 25° C.), 200 mM each of dNTP, 1.5 mM MgCl$_2$, 1 U Recombinant Taq DNA Polymerase (MBI Fermentas), 3 μl DNA sample and 25 pmol of each primer. A 2 minutes denaturation step at 94° C. was followed by 35 cycles of amplification with a PCR processor (Primus 96, HPL block, MWG, Germany). Each cycle included a denaturation step at 94° C. for 1 minute, a primer annealing step at 55° C. for 1½ minutes and a chain elongation step at 72° C. for 2 minutes. The final elongation step was prolonged by 4 minutes to ensure a complete extension of the amplified DNA. HeLa was used as positive controls for HPV 18, while SiHa or CaSki were used as positive control for HPV 16. Water was used as negative control.

Primers used for HPV PCR:

| Type | Primer | Primer sequence (SEQ ID No.) | | Position | Length (bp) |
|---|---|---|---|---|---|
| HPV16 | Pr1 | 5' TCA AAA GCC ACT GTG TCC TGA 3' | (318) | 421-440 | 119 |
| | Pr2 | 5' CGT GTT CTT GAT GAT CTG CAA 3' | (319) | 521-540 | |
| HPV18 | Pr1 | (5' TTC CGG TTG ACC TTC TAT GT 3') | (320) | 651-670 | 186 |
| | Pr2 | (5' GGT CGT CTG CTG AGC TTT CT 3') | (321) | 817-836 | |
| HPV31 | Pr1 | 5' CTA CAG TAA GCA TTG TGC TAT GC 3' | (322) | 3835-3875 | 153 |
| | Pr2 | 5' ACG TAA TGG AGA GGT TGC AAT AAC CC 3' | (323) | 3963-3988 | |
| HPV33 | Pr1 | 5' AAC GCC ATG AGA GGA CAC AAG 3' | (324) | 567-587 | 211 |
| | Pr2 | 5' ACA CAT AAA CGA ACT GTG TGT 3' | (346) | 758-778 | |

Primers used for HPV PCR:

| Type | Primer | Primer sequence (SEQ ID No.) | Position | Length (bp) |
|---|---|---|---|---|
| Gp+ | Gp5+ | 5' TTT GTT ACT GTG GTA GAT ACT AC 3' (338) | 6624-6649 | 150 |
|  | Gp6+ | 5' GAA AAA TAA ACT GTA AAT CAT ATT C (339) | 6719-6746 |  |
| BGPCO3 | Pr1 | 5' ACA CAA CTG TGT TCA CTA GC (340) |  |  |
| BGPCO5 | Pr2 | 5' GAA ACC CAA GAG TCT TCT CT (341) |  |  |

Visualization of the PCR products was done on a DNA 500 chip (Agilent Technologies, USA) according to their manual. The DNA chip uses micro scale gel electrophoresis with an optimal detection limit of 0.5-50 ng/ml. The results were interpreted using the Bioanalyzer 2100 software (Agilent Technologies, USA).

The following table confirms primers used for HPV PCR in patient samples and indicates additional PCR primers useful for HPV 35, 39, 45, 51, 52, 58 and HPV 6/11.

PCR primers for detection of HPV.

| Type | Primer | Primer sequence (SEQ ID No.) | Position | Length (bp) |
|---|---|---|---|---|
| HPV6/11 | Pr1 | 5' TAC ACT GCT GGA CAA CAT 3' (316) | 514-531 | 123 |
|  | Pr2 | 5' TCA TCT TCT GAG CTG TCT 3' (317) | 619-636 |  |
| HPV16 | Pr1 | 5' TCA AAA GCC ACT GTG TCC TGA 3' (318) | 421-441 | 120 |
|  | Pr2 | 5' CGT GTT CTT GAT GAT CTG CAA 3' (319) | 520-540 |  |
| HPV18 | Pr1 | 5' TTC CGG TTG ACC TTC TAT GT 3' (320) | 651-670 | 186 |
|  | Pr2 | 5' GGT CGT CTG CTG AGC TTT CT 3' (321) | 817-836 |  |
| HPV31 | Pr1 | 5' CTA CAG TAA GCA TTG TGC TAT GC 3' (322) | 3835-3857 | 155 |
|  | Pr2 | 5' ACG TAA TGG AGA GGT TGC AAT AAC CC 3' (323) | 3964-3989 |  |
| HPV33 | Pr1 | 5' AAC GCC ATG AGA GGA CAC AAG 3' (324) | 567-587 | 212 |
|  | Pr2 | 5' ACA CAT AAA CGA ACT GTG GTG 3' (325) | 758-778 |  |
| HPV35 | Pr1 | 5' CCC GAG GCA ACT GAC CTA TA 3' (326) | 610-629 | 231 |
|  | Pr2 | 5' GGG GCA CAC TAT TCC AA ATG 3' (327) | 821-840 |  |
| HPV39 | Pr1 | 5' GCA GAC GAC CAC TAC AGC AAA 3' (328) | 210-230 | 153 |
|  | Pr2 | 5' ACA CCG AGT CCG AGT AAT A 3' (329) | 344-362 |  |
| HPV45 | Pr1 | 5' GAA ACC ATT GAA CCC AGC AGA AAA 3' (330) | 428-451 | 154 |
|  | Pr2 | 5' TTG CTA TAC TTG TGT TTC CCT ACG 3' (331) | 558-581 |  |
| HPV51 | Pr1 | 5' GGA GGA GGA TGA AGT AGA TA 3' (332) | 658-677 | 169 |
|  | Pr2 | 5' GCC CAT TAA CAT CTG CTG TA 3' (333) | 807-826 |  |
| HPV52 | Pr1 | 5' GTG CCT ACG CTT TTT ATC TA 3' (334) | 296-315 | 233 |
|  | Pr2 | 5' GGG GTC TCC AAC ACT CTG AAC A 3' (335) | 507-528 |  |
| HPV58 | Pr1 | 5' TCA GGC GTT GGA GAC ATC 3' (336) | 157-174 | 162 |
|  | Pr2 | 5' AGC AAT CGT AAG CAC ACT 3' (337) | 301-318 |  |
| Gp+ | Gp5+ | 5' TTT GTT ACT GTG GTA GAT ACT AC 3' (338) |  | 150 |
|  | Gp6+ | 5' GAA AAA TAA ACT GTA AAT CAT ATT C (339) |  |  |
| BGPCO3 | Pr1 | 5' ACA CAA CTG TGT TCA CTA GC (340) |  |  |
| BGPCO5 | Pr2 | 5' GAA ACC CAA GAG TCT TCT CT (341) |  |  |

NASBA RNA Amplification
Precautions for avoiding contamination:
1. Perform nucleic acid release, isolation and amplification/detection in separate laboratory areas.
2. Store and prepare reagents for nucleic acid release, isolation and amplification/detection at the laboratory areas where nucleic acid release, isolation and amplification/detection are to be performed, respectively.
3. Keep all tubes and vials closed when not in use.
4. Pipettes and other equipment that have been used in one laboratory area must not be used in the other areas.
5. Use a fresh pipette or pipette tip for each pipetting action.
6. Use pipettes with aerosol resistant tips for fluids possibly containing nucleic acid. Pipetting of solutions must always be performed out of or into an isolated tube that is opened and closed exclusively for this action. All other tubes and vials should be kept closed and separated from the one handled.
7. Use disposable gloves when working with clinical material possibly containing target-RNA or amplified material. If possible, change gloves after each pipetting step in the test procedure, especially after contact with possibly contaminated material.
8. Collect used disposable material in a container. Close and remove container after each test run.
9. Soak tube racks used during nucleic acid isolation or amplification/detection in a detergent (e.g. Merck Extran MAO1 alkaline) for at least one hour after each test run.

The following procedure was carried out using reagents from the Nuclisens™ Basic Kit, supplied by Organon Teknika.
Procedure for n=10 samples:—
1. Prepare enzyme solution.
   Add 55 µl of enzyme diluent (from Nuclisens™ Basic Kit; contains sorbitol in aqueous solution) to each of 3 lyophilized enzyme spheres (from Nuclisens™ Basic Kit; contains AMV-RT, RNase H, T7 RNA polymerase and BSA). Leave this enzyme solution at least for 20 minutes at room temperature. Gather the enzyme solutions in one tube, mix well by flicking the tube with your finger, spin down briefly and use within 1 hour. Final concentrations in the enzyme mix are 375 mM sorbitol, 2.5 µg BSA, 0.08 U RNase H, 32 U T7 RNA polymerase and 6.4 U AMV-reverse transcriptase.
2. Prepare reagent sphere/KCl solution.
   For 10 samples: add 80 µl reagent sphere diluent (from Nuclisens™ Basic Kit; contains Tris/HCl (pH 8.5), 45% DMSO) to the lyophilized reagent sphere (from Nuclisens™ Basic Kit; contains nucleotides, dithiothreitol and MgCl$_2$) and immediately vortex well. Do this with 3 reagent spheres and mix the solutions in one tube.
   Add 3 µl NASBA water (from Nuclisens™ Basic Kit) to the reconstituted reagent sphere solution and mix well.
   Add 56 µl of KCl stock solution (from Nuclisens™ Basic Kit) and mix well. Use of this KCl/water mixture will result in NASBA reactions with a final KCl concentration of 70 mM. Final concentrations in the reagent/KCl solution are 1 mM of each dNTP, 2 mM of ATP, UTP and CTP, 1.5 mM GTP, and 0.5 mM ITP, 0.5 mM dithiothreitol, 70 mM KCl, 12 mM MgCl$_2$, 40 mM Tris-HCl (pH 8.5).
3. Prepare primer/probe solution containing target-specific primers and molecular beacon probe.
   For each target reaction transfer 91 µl of the reagent sphere/KCl solution (prepared in step 2) into a fresh tube. Add 25 µl of primers/molecular beacon solution (to give final concentration of ~0.1-0.5 µM each of the sense and antisense primers and ~15-70 pmol molecular beacon probe per reaction). Mix well by vortexing. Do not centrifuge.
   In case less than 10 target RNA amplifications are being performed refer to the table below for the appropriate amounts of reagent sphere solution, KCl/water solution and primers to be used. Primer solutions should be used within 30 minutes after preparation.

| Reactions (n) | Reagent sphere solution (µl) | KCl/water (µl) | Primer mix (µl) |
|---|---|---|---|
| 10 | 80 | 30 | 10 |
| 9 | 72 | 27 | 9 |
| 8 | 64 | 24 | 8 |
| 7 | 56 | 21 | 7 |
| 6 | 48 | 18 | 6 |
| 5 | 40 | 15 | 5 |
| 4 | 32 | 12 | 4 |
| 3 | 24 | 9 | 3 |
| 2 | 16 | 6 | 2 |
| 1 | 8 | 3 | 1 |

4. Addition of samples
For each target RNA reaction:
   In a 96 well microtiter plate pipette 10 µl of the primer/probe solution (prepared in step 3) into each of 10 wells. Add 5 µl nucleic acid extract to each well. Incubate the microtiter plate for 4 minutes at 65±1° C. Cool to at 41±0.5° C. for 4 minutes. Then to each well add 5 µl enzyme solution. Immediately place the microtiter plate in a fluorescent detection instrument (e.g. NucliSens™ EasyQ Analyzer) and start the amplification.

Results from Clinical Study

Table 7 shows the distribution of real-time NASBA HPV positive (L1 and/or E6 expression) and PCR HPV positive cases related to cytology results. PCR amplification was carried out as described by Karlsen et al., J Clin Microbiol. 34: 2095-2100, 1996. The figures for expected histology are based on average results from similar study on CIN III lesions (Clavel et al., Br J Cancer, 84: 1616-1623, 2001). The results from several example cases are listed in Table 8.

TABLE 7

|  | Normal | Benign | Condyloma | CIN III |
|---|---|---|---|---|
| Cytology | 4474 | 66 | 16 | 15 |
| PCR | 9.0% | 44.6% | 87.5% | 73.3% |
| Real-time NASBA | 1% | 24.6% | 37.5% | 73.3% |
| Expected Histology | 0.2% | 5-15% | 15-20% | 71% |

TABLE 8

| Internal No. | Cytology | PCR | L1 NASBA | E6 NASBA |
|---|---|---|---|---|
| 84 | Neg | Neg | Neg | 31 |
| 289 | Neg | 31 | Pos | 31 |
| 926 | Neg | Neg | Pos | 16 |
| 743 | Benign | Neg | Neg | 33 |
| 1512 | Benign | 16 | Pos | 16 |
| 3437 | Benign | Neg | Neg | 18 |
| 3696 | Benign | 16 | Pos | Neg |
| 2043 | Condyloma | 16, 51 | Pos | 16 |
| 3873 | Condyloma | 16, 51 | Pos | 16 |
| 3634 | CIN II | 33 | Neg | 33 |
| 4276 | CIN III | Neg | Neg | 18 |
| 4767 | CIN III | 18 | Neg | 18 |
| 1482 | CIN III | Neg | Pos | 16 |
| 5217 | CIN III | 31 | Neg | 31 |
| 4696 | CIN III | Neg | Neg | Neg |

EXAMPLE 2

Sensitivity of Real-Time NASBA on Control Cell Lines

Cervical cancer cell lines, CaSki, SiHa and HeLa were diluted in lysis buffer either before automated extraction of nucleic acids using the Boom's extraction method from Organon Teknika/bioMerieux (parallels 1 and 3), or after nucleic acid extraction (parallel 2). Real-time NASBA was performed using molecular beacons probes labelled with Texas red (16, L1 and 18) or FAM (UIA, 33 and 31) following the protocol described above.

TABLE 9

| Number of Cells | CaSki 16 E6 | CaSki U1 | CaSki 16 E6 | CaSki U1 | CaSki 16 E6 | CaSki U1 | CaSki 33 L1 | CaSki 33 E6 | CaSki 33 L1 | CaSki 33 E6 | CaSki 33 L1 | CaSki 33 E6 | 18 E6 | 31 E6 | HeLa 18 E6 | HeLa 31 E6 | HeLa 18 E6 | HeLa 31 E6 |
|---|---|---|---|---|---|---|---|---|---|---|---|---|---|---|---|---|---|---|
| Parallels | 1 | 1 | 2 | 2 | 3 | 3 | 1 | 1 | 2 | 2 | 3 | 3 | 1 | 1 | 2 | 2 | 3 | 3 |
| 100 000 | + | + | + | + | + | + | + | – | + | – | + | – | + | – | + | – | + | – |
| 10 000 | + | + | + | + | + | + | + | – | + | – | + | – | + | – | + | – | + | – |
| 1 000 | + | + | + | + | + | + | + | – | + | – | + | – | + | – | + | – | + | – |
| 100 | + | + | + | + | + | + | + | – | + | – | + | – | + | – | + | – | + | – |
| 10 | + | + | + | + | + | + | – | – | – | – | + | – | + | – | + | – | + | – |
| 1 | – | – | + | – | + | – | – | – | – | – | – | – | + | – | + | – | + | – |
| $10^{-1}$ | – | – | – | – | – | – | – | – | – | – | – | – | – | – | – | – | – | – |

Thus, it is possible to detect HPV E6 mRNA in less than 1 cell using real-time NASBA.

Real-time NASBA was tested both as a multiplex assay and as single reactions. The results from the following sensitivity study are based on parallel runs of CaSki, SiHa and HeLa cell lines, and on three parallel runs on synthetic DNA oligos for HPV type 16, 18, 31 and 33. The definition of the detection limit is that both of the samples in the parallel are positive. The number in the brackets (x) indicates that the specified amount of cells also have been detected in some runs. Sensitivity is defined as the amount of cells necessary for detection of HPV in two parallel runs. The HPV types are determined from PCR and the specificity is based on NASBA compared to PCR.

Sensitivity

PCR: the HPV consensus PCR using Gp5+/6+ detected only down to $10^4$ SiHa and HeLa cells, and down to $10^3$ CaSki cells. However, the type specific PCR primer-sets were more sensitive, detecting $10^3$ ($10^2$) SiHa cells and 0.1 CaSki cells for HPV 16 type specific PCR primer-set, while the HPV 18 type specific PCR primer-set detected $10^2$ HeLa cells.

Real-time NASBA: Real-time NASBA with primers specific for U1A, detected 10(1) SiHa and CaSki cells and 1 HeLa cell in the reaction mixture. For the HPV 16 specific primers, the lower detection limit was (10) ($10^2$, 1) SiHa cells and 10 (1) CaSki cells and for the HPV 18 specific primers the detection limit was 1 (0.1) HeLa cell. The universal L1 primers detected 10 CaSki cells. HeLa cells and SiHa cells were not detected with the universal L1 primers.

Real-time multiplex NASBA with the U1A specific primers, had a lower detection limit of $10^2$(10) SiHa cells and 10(1) CaSki cells when combined with the HPV 16 specific primers, which had a lower detection limit for 10(1) SiHa and 10(1) CaSki cells. The L1 specific primers in combination with the HPV 33 specific primers detected $10^3$(102) CaSki cells. There was no competing HPV 33 sample in the reaction. For the HPV 18 specific primers, the lower detection limit was 1 (0.1) HeLa cell when combined with the HPV 31 specific primers. There was no competing HPV 31 sample in the reaction. Sensitivity of the HPV 31 and HPV 33 specific primers were not tested, due to lack of cell lines harbouring these HPV types. They were tested against samples containing HPV 31 and HPV 33, but the amount of cells and the copy number of HPV 31 and HPV 33 in these cells were unknown and most probably varied in different samples.

TABLE 10 sensitivity of real-time NASBA compared to PCR

| Primer | NASBA SiHa | NASBA CaSki | NASBA HeLa | PCR SiHa | PCR CaSki | PCR HeLa |
|---|---|---|---|---|---|---|
| GP5+/6+ | — | — | — | $10^4$ | $10^3$ | $10^3$ |
| L1 | — | $10^3$ ($10^2$) | — | — | — | — |
| U1A | $10^2$ (10) | 10 (1) | — | — | — | — |
| HPV 16 | 10 (1) | 10 | — | $10^3$ ($10^2$) | 0.1 | — |
| HPV 18 | — | — | 1 (0, 1) | — | — | $10^2$ |

Real-time NASBA was performed on samples from women admitted to Østfold Central Hospital for treatment of CIN in the period of 1999-2001 (see example 3). Molecular beacon probes labeled with FAM or Texas red were used together with the nucleic acid extraction and NASBA protocols described above. The results are shown in FIGS. 1A and 1B (HPV 16-patient sample 205), FIGS. 2A and 2B (HPV 18-patient sample 146), FIGS. 3A and 3B (HPV 31-patient sample 236), FIGS. 4A and 4B (HPV 33-patient sample 218) and FIGS. 5A and 5B (HPV 45-patient sample 343). In each case, the "A" figure is a single reaction while the "B" figure is the multiplex assay.

Specificity: Cross reactivity of Real-time NASBA. Real-time NASBA primer combinations were tested against 490 cervical samples from the Oslo study positive with PCR for HPV 6/11, 16, 18, 31, 33, 35, 39, 45, 51, 52, 58 or HPV X to check for cross reactivity between HPV types using NASBA. All samples have been typed by consensus PCR and type specific PCR for the respective HPV types, except for HPV type 39(2), 52(1) and 58(2). These samples are added to test against PreTect HPV-Proofer. HPV X are positive for consensus Gp5+/6+ PCR but negative for HPV6/11, 16, 18, 31, 33, 35, 45 and 51 by type specific PCR. Results are shown in table 14. No cross-reactivity was shown. Sequence confirmation of a selected number of cases from table 14 is shown in table 14a.

PCR: a total of 773 cervical samples were tested with PCR and the PreTect HPV-Proofer (Real time multiplex NASBA), and a total of 24.6% (190/773) samples were positive with the Gp5+/6+ consensus PCR primers. 74.1% (83/112) were typed to be HPV 16, 13% (15/112) HPV 18, 17% (19/112) HPV 31 and 12% (13/112) HPV 33 including multiple HPV infections. A total of 103 samples had single or multiple HPV infections, and 91.3% (94/103) had only a single HPV infection. Double HPV infections occurred in 8.7% (9/103) of the samples. All samples were first tested with the consensus Gp5+/6+ PCR primers. The HPV PCR negative samples from the consensus Gp5+/6+ were then tested with β-globin control primers for a verification of intact DNA. The HPV PCR positive samples were not subjected to this DNA control. The HPV negative samples in this study were all positive with β-globin control PCR primers. Only DNA samples positive with Gp5+/6+ PCR were subjected to HPV type specific PCR. HPV types of interest were HPV 16, 18, 31 and 33.

Real-time multiplex NASBA: For the real-time NASBA reactions, the primers and probes for the UIA gene product were used as a performance control for intact RNA. Samples negative for UIA were rejected.

A total of 14.2% (110/773) of the samples were positive with at least one of the HPV type-specific NASBA primers including samples showing multiple HPV infections. From these samples 54.5% (60/110) were positive with HPV 16 NASBA primers, 13.6% (15/110) with HPV 18 primers, 21.8% (24/110) with HPV 31 primers and 13.6% (15/110) with HPV 33 primers. A total of 45 samples were positive with the L1 consensus primers and usually together with HPV 16 E6/E7 oncogene expression 82.2% (37/45). The consensus L1 was detected in 2.2% (1/45) together with either HPV 18, 31 and 33 respectively. L1 was also detected alone in 8.9% (4/45) cases, and they all were PCR positive with Gp5+/6+ primers. A total of 108 samples had single or multiple HPV infections, and 98.1% (106/108) had only a single HPV infections. Double mRNA expression occurred in 1.9% (2/108) of the samples.

Real-time multiplex NASBA compared to PCR: a total of 87 samples showed presence of HPV 16 DNA or RNA with HPV 16 PCR or PreTect HPV-Proofer. 64.4% (56/87) were determined to be positive for HPV 16 with both PCR and real-time NASBA. 39.1% (34/87) were only positive with PCR and 3.4% (3/87) were positive only with real-time NASBA. For HPV 18, a total of 20 samples showed presence of HPV 18 DNA or RNA with either PCR or real-time NASBA. From these 20 samples, 50% (10/20) were positive with both tests, and 35% (7/20) were only positive with PCR and 15% (3/20) were only positive with real-time NASBA. A total of 27 samples showed presence of HPV 31 DNA or RNA with either PCR or real-time NASBA. Out of these 27 samples, 59.3% (16/27) were positive with both tests and 11.1% (3/27) were positive only with the PCR test and 18.5% (5/27) were only positive with the real-time NASBA test. For HPV 33, a total of 18 samples showed presence of HPV DNA or RNA with either PCR or PreTect-HPV Proofer and 55.6% (10/18) of the samples were tested positive with both tests. 16.7% (3/18) were only positive with PCR and 22.2% (4/18) were only positive with real-time NASBA.

TABLE 11 statistical distribution of HPV in samples with PCR and real-time NASBA

|  | PCR | % | NASBA | % |
|---|---|---|---|---|
| Total samples | 773 |  | 773 |  |
| Total positive samples | 190 | 24.6 | 110 | 14.2 |
| HPV16 | 83 | 74.1 | 60 | 54.5 |
| HPV 18 | 15 | 13 | 15 | 13.6 |
| HPV 31 | 19 | 17 | 24 | 21.8 |
| HPV33 | 13 | 12 | 15 | 13.6 |
| HPV X | 78 | 69.6 | — | — |

TABLE 12 correspondence between PCR and real-time NASBA

|  | Total | Both tests | % | Only PCR + | % (PCR) | % (Total) | Only NASBA | % NASBA | % (total) |
|---|---|---|---|---|---|---|---|---|---|
| HPV 16 | 87 | 56 | 64.4 | 34 | 41.0 | 39.1 | 3 | 5 | 3.4 |
| HPV 18 | 20 | 10 | 50.0 | 7 | 46.7 | 35.0 | 3 | 20 | 15.0 |
| HPV 31 | 27 | 16 | 59.3 | 3 | 15.8 | 11.1 | 5 | 20.8 | 18.5 |
| HPV 33 | 18 | 10 | 55.6 | 3 | 23.1 | 16.7 | 4 | 26.7 | 22.2 |

TABLE 13

Real-time NASBA results for L1

|  | Total | % |
|---|---|---|
| L1 (NASBA) | 45 | 100 |
| L1 + HPV 16 | 37 | 82.2 |
| L1 alone | 4 | 8.9 |
| L1 + HPV 18 | 1 | 2.2 |
| L1 + HPV 31 | 1 | 2.2 |
| L1 + HPV 33 | 1 | 2.2 |

TABLE 14

Genetic specificity of real-time multiplex NASBA compared to PCR

| NASBA | HPV (PCR) | | | | | | | | | | | |
|---|---|---|---|---|---|---|---|---|---|---|---|---|
| Primers | 6/11 | 16 | 18 | 31 | 33 | 35 | 39 | 45 | 51 | 52 | 58 | X | Total Number |
| 16 | 2 | 28 | 1 | 0 | 1 | 1 | 0 | 0 | 5 | 0 | 0 | 2 |  |
| 18 | 1 | 1 | 18 | 0 | 1 | 0 | 0 | 0 | 1 | 0 | 0 | 1 |  |
| 31 | 1 | 0 | 1 | 13 | 1 | 5 | 0 | 1 | 1 | 0 | 0 | 0 |  |
| 33 | 1 | 2 | 0 | 2 | 12 | 2 | 0 | 1 | 2 | 0 | 0 | 1 |  |
| 45 | 2 | 1 | 1 | 1 | 1 | 1 | 0 | 17 | 1 | 0 | 0 | 1 |  |
| Sum tested | 43 | 71 | 36 | 32 | 25 | 23 | 2 | 23 | 31 | 1 | 2 | 201 | 490 |

TABLE 14a

DNA sequencing from Gp5+ PCR primers
(not to be included in the article)

| Int No | HPV type by PCR | HPV type by PreTect HPV-Proofer | HPV type by Sequencing (BLAST) |
|---|---|---|---|
| 1272 | 16 | 16 | 16 |
| 152 | 35 |  | 35 |
| 2655 | 58 |  | 58 |
| 2924 | 33 | 33 | 33 |
| 2942 | 18 | 18 | 18 |
| 2987 | 16 | 16 | 16 |
| 3016 | 33 | 33 | 33 |
| 3041 | 35 |  | 35 |
| 3393 | 35 |  | 35 |
| 3873 | 16 | 16 | 16 |
| 4767 | 18 | 18 | 18 |
| 5707 | 18 | 18 | 18 |
| 845 | X |  | 39 |

Discussion

Sensitivity of real-time NASBA was generally better than the sensitivity of PCR. The general sensitivity of real-time NASBA for all the markers were between 1 and $10^2$ cells, which is considerable better than for the PCR reaction with a sensitivity range from $10^2$ to $10^4$. As expected, the sensitivity of the specific primers and probes were better than the sensitivity of the universal primers and probes. Real-time NASBA was just as sensitive or more sensitive than real-time multiplex NASBA.

Real-time NASBA primers and molecular beacon probe directed towards UIA (a human house keeping gene) were used as a performance control of the sample material in the real-time NASBA reaction to ensure that the RNA in the sample material was intact. A positive signal from this reaction was necessary for a validation of the real-time NASBA reaction.

The sensitivity of the universal real-time NASBA with L1 (the major capsid protein of HPV) was much better than for the universal Gp5+/6+ PCR, also directed against L1, with a sensitivity of 10 cells compared to $10^3$ ($10^2$) CaSki cells. These two primer sets (PCR and NASBA) have their targets in the same region of the conserved L1 gene of different HPV types. The differences in sensitivity may be due to the fact that there is usually one copy of each gene per cell, while the copy number of mRNA may be several hundreds. The real-time NASBA L1 primers did not detect SiHa or HeLa cells as the Gp5+/6+ PCR primers did, indicating lack of L1 expression in these cell lines. Gp5+/6+ PCR primers detected $10^4$ SiHa or HeLa cells. Considering the amount of HPV copies in each cell, it makes sense that the CaSki cells were detected in 1/10 the amount of cells from SiHa and HeLa since CaSki cells have 60-600 HPV copies per cell, both integrated and episomal, while SiHa cells have 1-2 HPV copies integrated per cell and HeLa cells have 10-50 HPV copies integrated per cell. The L1 primer set detected only CaSki cells, with both integrated and episomal forms of HPV, and not in SiHa or HeLa cells, with only integrated forms of HPV. This might indicate that the L1 gene is only expressed in episomal states of HPV infection, and therefore L1 may be a valuable marker for integration and persistence of HPV infection.

The HPV type-specific NASBA primers are directed against the full length E6/E7 transcript, which are expressed in large amount in cancer cells due to lack of E2 gene product. The real-time NASBA 16 type specific primers detected 10(1) SiHa cells and 10(1) CaSki cells compared to HPV 16 PCR primers that detected $10^3(10^2)$ SiHa cells. The explanation for this might be the different amount of HPV copies in each cell line. The CaSki cells have both integrated and episomal forms of HPV, while SiHa has only integrated forms of HPV. This may be due to high expression of mRNA from the E6/E7 genes. For detection of CaSki cells, the detection limit for the NASBA HPV 16 primers were 10(1) CaSki cells compared to 0.1 CaSki cells for the HPV 16 PCR primers. This is peculiar, but an explanation may be that the CaSki cells contain from 60-600 copies of HPV 16 DNA, so that it is possible to detect 0.1 CaSki cells with 6-60 HPV 16 DNA copies. The lower sensitivity of real-time NASBA compared to PCR may indicate that the expression of E6/E7 in the CaSki cells is moderate/low. Degradation of the unstable mRNA may also be an explanation. The amount of HPV copies in the CaSki cells may be in the order of 60-600 times more than in the SiHa cells, which is shown by the more sensitive detection of CaSki cells.

The type specific HPV 18 PCR primers detected $10^2$ HeLa cells. This is a magnitude of 100 better than the HPV consensus Gp5+/6+ primers and states that specific primers are generally more sensitive than consensus primers. The sensitivity of the type specific HPV 18 NASBA primers was 1 (0.1) HeLa cells, indicating high expression of E6/E7 in HeLa cells.

The sensitivity of UIA NASBA primers was 10 SiHa or CaSki. The target for the UIA primer set is a human housekeeping gene that is expressed in every human cell.

The sensitivity of PCR and NASBA varies for different primer sets and sample material, and generally type specific primers are more sensitive than consensus primers due to base pair mismatch in consensus primer sets. The annealing temperature for the primers in the PCR reaction can be optimised, giving optimal reaction condition for the primers. In contrast to the annealing temperature in PCR, the annealing temperature for the NASBA primers must be fixed at 41° C. This lack of temperature flexibility may make the NASBA primers less sensitive and specific than the PCR primers.

PCR amplifies double stranded DNA and the target is usually present as one copy per cell and this makes it vulnerable to the number of cells in the sample material. The target for the NASBA reaction is RNA, and mRNA may be present as multiple copies per cell, depending on the expression of the genes. By choosing a gene that is highly expressed, the mRNA copy number may be several hundred per cell and therefore easier to detect.

dsDNA is relatively stable in the cell and the material stays intact for a long time. In contrast to dsDNA, mRNA is generally not very stable and degradation of mRNA is rapid depending on the cell. There is no detected DNase or RNase activity in the lysis buffer so both dsDNA and ssRNA should be stable. Autocatalytic activity may degrade both DNA and RNA. The DNA/RNA from the cervix sample should stay intact, when stored in the lysis buffer, for 24 hours at 15-30° C., 7 days at 2-8° C. or at −70° C. for long term storage.

A limitation in the real-time NASBA reaction is the concentration of the molecular beacon probes. The amount of products will exceed the concentration of the molecular beacon probes and therefore it will not be detected because a high molecular beacon probe concentration will make the reaction mixture more complex and inhibit the amplification reaction.

Nucleotides may also be a limitation to the final amount of the amplification product, both in the PCR and in the NASBA reaction. The final concentration of the amplified product may in itself inhibit further amplification because of the amount of product and the complexity of the reaction mixture. During a NASBA reaction in the presence of molecular beacons, the probe might compete with the amplification by hybridising to the template, making it unavailable for following RNA synthesis. In this way, RNA is subtracted as substrate for the reverse transcription steps and further RNA synthesis by T7 RNA polymerase. This competition is not significant with low amounts of molecular beacon, and with a high amount of molecular beacon this inhibition can be overcome by a higher number of copies of input RNA.

The linear relationship between the amount of input RNA and the time-to-positive signal was tested in a ten-fold serial dilutions of different HPV cell lines. There was a clear indication that a positive signal was dependent on the amount of input RNA and time. The multiplex reaction needed more time than the single reaction to show a positive signal. This might be due to competition in the more complex mixture in the multiplex reaction vessel and also to the fact that the multiplex reaction has a different and lower concentration of primer and probe. The relationship between amount of target RNA and time to positive signal opens up for a real-time multiplex quantitative amplification reaction with internal RNA standards in each reaction vessel.

Real-time NASBA: single vs. multiplex. Real-time NASBA was generally more sensitive than real-time multiplex NASBA. This was as expected because of competition between primers and probes in the multiplex reaction. The final concentration of primers and molecular beacon probes were optimised in the multiplex reaction so that for at least one of the primer and probe sets the concentration were lower than in the single reaction. From this it follows that with a lower concentration of primers, the less sensitive the reaction, or at least the less rapid the reaction. It will take longer time to reach the exponential stage of the amplification reaction and therefore longer time to detect the products. The concentration of the primers will not be a limitation to the final concentration of the product in the NASBA reaction because the double stranded DNA created from the primers will continue to serve as a template for the RNA polymerase over and over again in a loop. The sensitivity of multiplex real-time NASBA was the same for HPV 16 and HPV 18 compared to single real-time NASBA, but the sensitivity for L1 decreased drastically from a detection limit of 10(1) in the single reaction to $10^3(10^2)$ CaSki cells in the multiplex reaction. For UIA NASBA primers, the sensitivity decreased from 10(1) to $10^2$ (10) SiHa cells, while the detection limit remained the same for the CaSki cells. This decrease in detection limit may be to more complex competition of primers and molecular beacon probes in the multiplex reaction. The final concentration of primers and molecular beacon probes may not be the best and the different primers and molecular beacon probes in the multiplex reaction may interfere with each other. The UIA NASBA primers detected 1 HeLa cell. One might expect the same detection level in all the cell lines, but the sensitivity of HeLa cells were ¹/₁₀ of the detection level of SiHa and CaSki cells. These cell lines are cancer cells and they might have different impact on the cells so that the expression of UIA is different. The differences may also be due to different amount of cells in each reaction, because of counting errors during harvesting of the cells.

Real-time NASBA showed no cross reactivity between HPV 16, 18, 31 and 33 or with HPV 6/11, 35, 39, 45, 51, 52, 58 or HPV X.

The specificity of the PCR reaction may be better than the specificity of the real-time NASBA reaction because the NASBA reaction is an isothermal reaction at 41° C. with no possibilities to change the annealing temperature of the primers. The primers are basically designed the same way as for the PCR primers. In a PCR reaction, you have the possibility to change the annealing temperature, in contrast to the NASBA reaction, and therefore choose an annealing temperature that is optimal for the two primers. This makes the annealing of the primers more specific. The PCR results where visualized with gel electrophoresis. But the molecular beacon probes in the real-time NASBA reaction is an additional parameter compared to PCR and therefore may give the overall NASBA reaction a better specificity. It is also easier to find two different regions on the DNA sequence for primer annealing because there is much greater flexibility in the length of the PCR product, than for the NASBA product, which should be less than 250 bp. It is important for the specificity of the NASBA reaction to choose a unique area that is not conserved among the different HPV types. A couple of base pair mismatches may still give an amplification or hybridisation of the target.

Detection of CaSki (integrated and episomal state) cells with the universal L1 NASBA primers and not SiHa or HeLa (both integrated) may give an indication that integrated HPV doesn't show any L1 expression, while HPV in the episomal state may have L1 expression.

In summary, an identification assay has been developed for HPV type 16, 18, 31 and 33 that can accurately identify the oncogenic E6/E7 expression of these HPV types. The assay can also identify the expression of the major capsid protein, L1.

EXAMPLE 3

Further Clinical Study in 190 Patients

Patients/Clinical Samples
Biopsies from 190 women admitted to Østfold central-hospital for treatment of CIN in the period 1999-2001. The mean age of the 190 women included in the study was 37.4 years (range 22-74 years). Biopsies were frozen in −80° C. immediately after collection.
Cytological Examination of Samples The routine cytological reports were used to record cytological findings. No attempt was made to re-evaluate the slides. Each one of them indicated a CIN II-III condition, i.e. a high grade dysplasia or HSIL, which was the basis for hospital admittance, colposcopy and biopsy.
Histological Examination of Samples A biopsy, here termed biopsy 1, was taken after a high-grade cytology report. If it confirmed a high-grade lesion (CIN II or III), the patient was again admitted to hospital, this time for colposcopically guided conization. Before the conization, but after local anesthesia was applied, a second biopsy (biopsy 2) was taken from an area of portio where a dysplasia was most likely to be localised, judged from the gross findings. This biopsy (2×2 mm) was frozen within 2 minutes in a −80° C. freezer.

Biopsy 2 was split in two when frozen and half was used for DNA/RNA extraction. The other half was fixed in 10% buffered formaldehyde and processed for histopathological examination. Some lesions were not correctly oriented in the paraffin block and had to be reoriented or serial sectioned in order to show the relevant surface epithelium. Consequently, it cannot be guaranteed that exactly the same tissue was used for the extraction and for the histopathological evaluation. The cone specimen, finally, was evaluated by the local pathologist, who in all cases could confirm the presence of dysplasia. It was not always the same grade as in the original biopsy, and, in many cases, not the same as in biopsy 2.
Extraction of Nucleic Acids Nucleic acids were isolated using the automated Nuclisens Extractor as previously described (Boom et al., 1990). Each biopsy was cut in two pieces, one intended for histological examination and the other half for RNA analysis. The material intended for RNA analysis was divided into smaller pieces while kept on dry ice (−80° C.) and put into 1 ml of lysisbuffer (as above) followed by 20 seconds of homogenisation using disposable pestles. 100 ml of the sample was further diluted 10 fold in lysisbuffer and 100 ml was then extracted for DNA/RNA. The extracted DNA/RNA was eluted with ~40 ml of elution buffer (Organon Teknika) and stored at −70° C.

All molecular beacon probes used in this study employ the fluorophore FAM (6-carboxyfluorescein) at the 5' end of the structure. This was bound to a variable stem-loop sequence coupled to the universal quencher 4-(4'dimethylaminophenylazo)benzoic acid (DABCYL) at the 3' end. The probes were delivered by Eurogentec, Belgium. Final concentration of MBs used in the reaction was 2.5 mM. For the real-time NASBA we made use of the NucliSens Basic Kit (Organon Teknika, Netherlands), intended for the development of user-defined RNA amplification assays. The NASBA amplification was carried out in a volume of 20 µl. The primer-sets and probes were directed against full-length E6/E7 mRNA for the high-risk HPV 16, 18, 31, and 33. As performance control, to avoid false negative results due to degradation of nucleic acid, we used a primer set and probe directed against the human U1 small nuclear ribonucleoprotein (snRNP) specific A protein (UIA mRNA) (Nelissen et al., 1991). All samples were run in duplicate on separate machines (microplate readers for measuring fluorescence and absorbance, Bio-tek FL-600 FA from MWG). mRNA isolated from CaSki/SiHa or HeLa cells served as positive controls for HPV 16 and HPV 18 transcripts, respectively. Negative controls, included for every 7 reaction, consisted of a reaction containing all reagents except mRNA.

HPV DNA Analysis; Polymerase Chain Reaction

The same extracts and amounts as used in the NASBA reaction were used for PCR. The L1 consensus primers Gp5+/Gp6+ were used to detect all samples containing HPV DNA. The PCR amplification was carried out as described above. The first DNA denaturation was done for 2 minutes at 94° C., then 40 cycles of PCR were run: denaturation 1 minute at 94° C., annealing for 2 minutes at 40° C., extension for 1.5 minutes at 72° C., followed by a final extension for 4 minutes at 72° C. Typing of HPV was performed by using PCR type-specific primers against HPV 16, 18, 31, and 33 (6/11, 35, 45, 51, 52, 58), as described above.

Results

Originally 190 patients were biopsied after being given the diagnosis CIN I, CINII, or CIN III by cytology. A high-grade lesion was confirmed by histologically examination, 150 samples diagnosed as CIN III (78.9%). Biopsy 2, taken before conization, was used for RNA analysis. However, histological examination of this biopsy diagnosed only 53 samples of the originally 150 as CIN III [54 were given no diagnosis, 24 diagnosed as CIN II, 18 as CIN I, and 4 as HPV/condylom]. The number of CIN II samples increased from 16 (8.4%) to 30 (15.8%) [by Histology 124 diagnosed as CIN III, 4 as CIN II, 1 as carcinom, and 1 as CIN I. 12 CIN II cases from Histology I were given a lower diagnosis in Histology II]. The degree of CIN I increased from 6 samples (3.2%) to 32 samples (16.8%). The 2 squamous cell carcinomas were in Histology II diagnosed as CIN III, the adenocarcinom as CIN II. In 71 samples (38.4%) high-grade lesions were not detected.

HPV oncogenic RNA was detected in 69 (36%) of the 190 patients. Of the 53 samples (28%) diagnosed as CIN III in Histology II, we found 40 (76%) cases showing HPV 16, 18, 31, or 33 oncogenic expression. In addition, we found oncogenic expression in 9 of 30 cases (30%) of CIN II, in 4 of 32 cases (13%) of CIN I, in 14 of 71 cases (20%) not showing cell abnormalities, and in 2 of 4 (50%) samples diagnosed as HPV/condyloma.

HPV 16 RNA was found in 42 of the 190 patients, HPV 18 was found in 7 (3.7%), HPV 31 in 15 (7.9%), and HPV 33 in 8 (4.2%). One patient had mixed infection with HPV 16 and HPV 18, and one with HPV 16 and HPV 31.

Using the consensus Gp5+/Gp6+ primers directed against the L1 gene, encoding the major capsid protein, PCR detected HPV in 81 of the 190 cervical biopsies (43%). Of the 119 cases given a diagnosis in the second histological examination (115 diagnosed as CIN, 4 as HPV/condyloma) 63 were found to contain HPV DNA. The additional 18 cases detected were not given any histological diagnosis. 20 of the 81 cases were not detected by NASBA; 7 out of these were given the diagnosis CIN III, 2 were diagnosed as CIN II, 4 diagnosed as CIN I, and 7 given no diagnosis.

Type-specific PCR detected 85 cases containing HPV; 66 having HPV 16, 10 HPV 18, 14 HPV 31, 7 HPV 33. 12 cases had multiple infection: 3 with HPV 16+18; 4 with HPV 16+33, 5 with HPV 16+31. 20 no diagnosis.

EXAMPLE 4

HPV Detected by PreTect HPV-Proofer and PCR Compared to Cytology and Histology:

Normal and ASCUS samples (including borderline smears) were determined by cytology. All samples were tested with consensus PCR and PreTect HPV-Proofer but only the consensus positive samples were typed by PCR. The CIN 3 and cancer samples were determined by histology and all the samples were tested with all three methods. The results are shown in FIG. 6. Concordance between real-time multiplex NASBA and PCR compared to cytology or histology is shown in Table 15 below.

TABLE 15

Concordance between real-time multiplex NASBA and PCR compared to cytology or histology

| Cytology/Histology | Concordance$^a$ (Number) | Concordance$^b$ (Number) |
|---|---|---|
| Normal | 98.2% (4043) | 42.8% (138) |
| ASCUS$^c$ | 94.5% (55) | 78.6% (14) |
| CIN 3 | 94.3% (53) | 93.2% (44) |
| Cancer | 99.0% (196) | 98.8% (170) |

Only samples positive by Gp5+/6+ PCR have been typed.
$^a$Including PCR and real-time multiplex NASBA positive and negative samples.
$^b$Including only PCR and/or real-time multiplex NASBA positive samples.
$^c$ASCUS excluding borderline smears.

EXAMPLE 5

The invention provides a kit for detection of mRNA transcripts from the E6 gene(s) of HPV the kit comprising one or more of, two or more of and preferably all of the following primer pairs and accompanying identification probes.

```
HPV16:HPV16.txt 7905 b.p
HPV16P2:
p2:116 (20)
                                          (SEQ ID No. 175)
GATGCAAGGTCGCATATGAGCCACAGGAGCGACCCAGAAA 16 p1 (no7)
                                          (SEQ ID No. 177)
```

-continued
AATTCTAATACGACTCACTATAGGGAGAAGG ATT CCC ATC TCT
ATA TAC TA (51 baser)

HPV16P02:
p0:230 (20)
(SEQ ID No. 19)
TATGACTTTGCTTTTCGGGA
H16e6702po

HPV 18:HPV18.txt 7857 b.p
HPV18P2:
p2:698 (22)
(SEQ ID No. 196)
GATGCAAGGTCGCATATGAGGAAAACGATGAAATAGATGGAG
H18e6702p2
HPV18P4:
p1:817 (20)
(SEQ ID No. 203)
AATTCTAATACGACTCACTATAGGGAGAAGGGGTCGTCTGCTGAGCTTTC
T
H18e6703p1 (Multiplex)

HPV18P02:
po:752 (21)
(SEQ ID No. 32)
GAACCACAACGTCACACAATG
H18e6702po

HPV 31:HPV31.txt 7912 b.p
HPV31P3:
p2:617 (20)
(SEQ ID No. 210)
GATGCAAGGTCGCATATGAGACTGACCTCCACTGTTATGA
H31e6703p2 p1:766 (20)
(SEQ ID No. 211)
AATTCTAATACGACTCACTATAGGGAGAAGGTATCTACTTGTGTGCTCTG
T
H31e6703p1

HPV31P04:
po:686 (26)
(SEQ ID No. 50)
GGACAAGCAGAACCGGACACATCCAA
H31e6704po

HPV33:HPV33.txt 7909 b.p
HPV33P1:
p2:618 (22)
(SEQ ID No. 221)
GATGCAAGGTCGCATATGAGTATCCTGAACCAACTGACCTAT
H33e6701p2 p1:763 (19)
(SEQ ID No. 222)
AATTCTAATACGACTCACTATAGGGAGAAGGTTGACACATAAACGAACTG
H33e6701p1

HPV33P03:
po:699 (23)
(SEQ ID No. 59)
GGACAAGCACAACCAGCCACAGC
H33e6703po

As alternative to the probes shown above the kit may optionally include one or more of the following molecular beacon probes:

Molecular Beacon Probes:
H16e6702mb2-FAM
(SEQ ID No. 175)
ccagctTATGACTTTGCTTTTCGGGAagctgg H18e6702mb1-TxR
(SEQ ID No. 198)

-continued
cgcatgGAACCACAACGTCACACAATGcatgcg

H31e6704mb2-FAM
(SEQ ID No. 215)
ccgtcgGGACAAGCAGAACCGGACACATCCAAcgacgg

H33e6703mb1-FAM
(SEQ ID No. 225)
ccaagcGGACAAGCACAACCAGCCACAGCgcttgg

Preferably the kit of the invention also includes the following primer pair and probe.:
HPV45: HPV45.txt 7858 bp (X74479)

HPV45P1:
p2:430 (21):
(SEQ ID No. 261)
GATGCAAGGTCGCATATGAGAACCATTGAACCCAGCAGAAA
H45e6701p2 p1:527(22):
(SEQ ID No. 262)
AATTCTAATACGACTCACTATAGGGAGAAGGTCTTTCTTGCCGTGCCTGG
TCA

H45e6701p1
HPV45P01:
po:500 (20):
(SEQ ID No. 108)
GTACCGAGGGCAGTGTAATA
H45e6701po

The HPV 45 probe above may be replaced by an HPV molecular beacon probe as follows:

H45e6701mb1
cgatcgGTACCGAGGGCAGTGTAATAcgatcg (SEQ ID No. 342)

In addition the kit may include one or more of the following primer pairs and accompanying identification probes depending on the geographical area of use of the kit.

HPV52: HPV52.txt 7942 bp (X74481)
HPV52P1:
p2:144 (22):
(SEQ ID No. 239)
GATGCAAGGTCGCATATGAGTTGTGTGAGGTGCTGGAAGAAT
H52e6701p2 p1:358(18):
(SEQ ID No. 240)
AATTCTAATACGACTCACTATAGGGAGAAGGCCCTCTCTTCTAATGTTT
H52e6701p1

HPV52P01:
Po:296 (20):
(SEQ ID No. 334)
GTGCCTACGCTTTTTATCTA
H52e6701po

HPV58 HPV58.txt 7824 bp (D90400)
HPV58P2:
p2:173 (18):
(SEQ ID No. 245)
GATGCAAGGTCGCATATGAGTCTGTGCATGAAATCGAA
H58e6702p2 p1:291 (18):
(SEQ ID No. 346)
AATTCTAATACGACTCACTATAGGGAGAAGGAGCACACTTTACATACTG
H58e6702p1

HPV58P02:

po:218 (22):

(SEQ ID No. 84)

TTGCAGCGATCTGAGGTATATG

H58e6702po

HPV51 HPV51.txt 7808 bp (M62877)

HPV51PA/P:

p2:655 (23):

(SEQ ID No. 275)

GATGCAAGGTCGCATATGAG AGA GGA GGA GGA TGA AGT AGA

TA

H51e6702p2 p1:807 (20):

(SEQ ID No. 274)

AATTCTAATACGACTCACTATAGGGAGAAGG GCC CAT TAA CAT

CTG CTG TA

H51e6701p1

HPV51POA:

po:771 (24):

(SEQ ID No. 129)

TGG CAG TGG AAA GCA GTG GAG ACA

H51e67o2po

The probes shown above may be replaced in the kit by the following molecular beacon probes:

H52e6701mb1

(SEQ ID No. 343)

cgatcgGTGCCTACGCTTTTTATCTAcgatcg

H58e6702mb1

(SEQ ID No. 344)

ccgtcgTTGCAGCGATCTGAGGTATATGcgacgg

H51e6702mb1

(SEQ ID No. 345)

cgatcgTGG CAG TGG AAA GCA GTG GAG ACAcgatcg

---

The invention claimed is:

1. An in vitro method of screening a human subject for the presence of integrated HPV or a modified episomal HPV genome, which method comprises specifically detecting, in a sample obtained from the human subject, expression of full length unspliced mRNA transcripts from the E6 gene of human papillomavirus wherein the splice variants E6*I, E6*II and E6*III are not detected, and wherein a subject positive for expression of full length unspliced E6 mRNA from at least one HPV type selected from the group consisting of HPV16, HPV18, HPV31, HPV33, HPV35, HPV45, HPV52 and HPV58 are scored as carrying integrated HPV or a modified episomal HPV genome.

2. The method of claim 1 wherein the human subject is previously identified as infected with human papillomavirus DNA in cells of the cervix.

3. The method of claim 1 wherein the human subject has a previous diagnosis of ASCUS, CIN 1 lesions, CIN 2 lesions or condyloma.

4. The method of claim 1 which comprises specifically detecting expression of full length unspliced E6 mRNA transcripts from at least HPV type 16, wherein a subject positive for expression of full length unspliced E6 mRNA from at least HPV type 16 is scored as carrying integrated HPV or a modified episomal HPV genome.

5. The method of claim 4 wherein said full length E6 mRNA transcripts of HPV type 16 contain all of the region from nucleotide 97 to nucleotide 880 in the E6 open reading frame, inclusive of nucleotides 97 and 880.

6. The method of claim 1 wherein specifically detecting E6 mRNA expression is carried out using an amplification reaction to amplify a region of the mRNA, together with real-time detection of the products of the amplification reaction.

7. The method of claim 6 wherein specifically detecting E6 mRNA expression is carried out using real-time NASBA.

8. An in vitro method of screening a human subject for the presence of integrated HPV or a modified episomal HPV genome, which method comprises specifically detecting, in a sample obtained from the human subject, expression of full length unspliced mRNA transcripts from the E6 gene of human papillomavirus using primers or probes specific for a region of the full length E6 mRNA transcript which is not present in the splice variants E6*I, E6*II and E6*III, and wherein a subject positive for expression of full length unspliced E6 mRNA from at least one HPV type selected from the group consisting of HPV16, HPV18, HPV31, HPV33, HPV35, HPV45, HPV52 and HPV58 are scored as carrying integrated HPV or a modified episomal HPV genome.

9. The method of claim 8, wherein the region of the full length E6 mRNA transcript which is not present in the splice variants E6*I, E6*II and E6*III is the region from nucleotide 97 to nucleotide 880 in the E6 open reading frame, inclusive of nucleotides 97 and 880.

10. The method of claim 8 wherein the human subject has a previous diagnosis of ASCUS, CIN 1 lesions, CIN 2 lesions or condyloma.

11. The method of claim 8 wherein the human subject is previously identified as infected with human papillomavirus DNA in cells of the cervix.

12. The method of claim 8 which comprises specifically detecting expression of full length unspliced E6 mRNA transcripts from at least HPV type 16, wherein a subject positive for expression of full length unspliced E6 mRNA from at least HPV type 16 is scored as carrying integrated HPV or a modified episomal HPV genome.

13. The method of claim 12 wherein said full length unspliced E6 mRNA transcripts of HPV type 16 contain all of the region from nucleotide 97 to nucleotide 880 in the E6 open reading frame, inclusive of nucleotides 97 and 880.

14. The method of claim 8 wherein specifically detecting E6 mRNA expression is carried out using an amplification reaction to amplify a region of the mRNA, together with real-time detection of the products of the amplification reaction.

15. The method of claim 14 wherein specifically detecting E6 mRNA expression is carried out using real-time NASBA.

* * * * *

SEQUENCE LISTING

<160> NUMBER OF SEQ ID NOS: 346

<210> SEQ ID NO 1
<211> LENGTH: 24
<212> TYPE: DNA
<213> ORGANISM: Artificial sequence
<220> FEATURE:
<223> OTHER INFORMATION: /note="HPV Primer"

<400> SEQUENCE: 1
ccacaggagc gacccagaaa gtta                              24

<210> SEQ ID NO 2
<211> LENGTH: 22
<212> TYPE: DNA
<213> ORGANISM: Artificial sequence
<220> FEATURE:
<223> OTHER INFORMATION: /note="HPV Primer"

<400> SEQUENCE: 2
acggtttgtt gtattgctgt tc                                22

<210> SEQ ID NO 3
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 3
ccacaggagc gacccagaaa                                   20

<210> SEQ ID NO 4
<211> LENGTH: 20

-continued

```
<212> TYPE: DNA
<213> ORGANISM: Artificial sequence
<220> FEATURE:
<223> OTHER INFORMATION: /note="HPV Primer"

<400> SEQUENCE: 4
ggtttgttgt attgctgttc                                               20

<210> SEQ ID NO 5
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 5
attcccatct ctatatacta                                               20

<210> SEQ ID NO 6
<211> LENGTH: 18
<212> TYPE: DNA
<213> ORGANISM: Artificial sequence
<220> FEATURE:
<223> OTHER INFORMATION: /note="HPV Primer"

<400> SEQUENCE: 6
tcacgtcgca gtaactgt                                                 18

<210> SEQ ID NO 7
<211> LENGTH: 18
<212> TYPE: DNA
<213> ORGANISM: Artificial sequence
<220> FEATURE:
<223> OTHER INFORMATION: /note="HPV Primer"

<400> SEQUENCE: 7
ttgcttgcag tacacaca                                                 18

<210> SEQ ID NO 8
<211> LENGTH: 18
<212> TYPE: DNA
<213> ORGANISM: Artificial sequence
<220> FEATURE:
<223> OTHER INFORMATION: /note="HPV Primer"

<400> SEQUENCE: 8
tgcagtacac acattcta                                                 18

<210> SEQ ID NO 9
<211> LENGTH: 18
<212> TYPE: DNA
<213> ORGANISM: Artificial sequence
<220> FEATURE:
<223> OTHER INFORMATION: /note="HPV Primer"

<400> SEQUENCE: 9
gcagtacaca cattctaa                                                 18

<210> SEQ ID NO 10
<211> LENGTH: 18
<212> TYPE: DNA
<213> ORGANISM: Artificial sequence
<220> FEATURE:
<223> OTHER INFORMATION: /note="HPV Primer"

<400> SEQUENCE: 10
acagttatgc acagagct                                                 18
```

<210> SEQ ID NO 11
<211> LENGTH: 18
<212> TYPE: DNA
<213> ORGANISM: Artificial sequence
<220> FEATURE:
<223> OTHER INFORMATION: /note="HPV Primer"

<400> SEQUENCE: 11
atattagaat gtgtgtac                                               18

<210> SEQ ID NO 12
<211> LENGTH: 18
<212> TYPE: DNA
<213> ORGANISM: Artificial sequence
<220> FEATURE:
<223> OTHER INFORMATION: /note="HPV Primer"

<400> SEQUENCE: 12
ttagaatgtg tgtactgc                                               18

<210> SEQ ID NO 13
<211> LENGTH: 18
<212> TYPE: DNA
<213> ORGANISM: Artificial sequence
<220> FEATURE:
<223> OTHER INFORMATION: /note="HPV Primer"

<400> SEQUENCE: 13
gaatgtgtgt actgcaag                                               18

<210> SEQ ID NO 14
<211> LENGTH: 18
<212> TYPE: DNA
<213> ORGANISM: Artificial sequence
<220> FEATURE:
<223> OTHER INFORMATION: /note="HPV probe"

<400> SEQUENCE: 14
acagttatgc acagagct                                               18

<210> SEQ ID NO 15
<211> LENGTH: 18
<212> TYPE: DNA
<213> ORGANISM: Artificial sequence
<220> FEATURE:
<223> OTHER INFORMATION: /note="HPV probe"

<400> SEQUENCE: 15
atattagaat gtgtgtac                                               18

<210> SEQ ID NO 16
<211> LENGTH: 18
<212> TYPE: DNA
<213> ORGANISM: Artificial sequence
<220> FEATURE:
<223> OTHER INFORMATION: /note="HPV probe"

<400> SEQUENCE: 16
ttagaatgtg tgtactgc                                               18

<210> SEQ ID NO 17
<211> LENGTH: 18
<212> TYPE: DNA
<213> ORGANISM: Artificial sequence
<220> FEATURE:
<223> OTHER INFORMATION: /note="HPV probe"

-continued

<400> SEQUENCE: 17
gaatgtgtgt actgcaag                                                    18

<210> SEQ ID NO 18
<211> LENGTH: 22
<212> TYPE: DNA
<213> ORGANISM: Artificial sequence
<220> FEATURE:
<223> OTHER INFORMATION: /note="HPV probe"

<400> SEQUENCE: 18
ctttgctttt cgggatttat gc                                               22

<210> SEQ ID NO 19
<211> LENGTH: 20
<212> TYPE: DNA
<213> ORGANISM: Artificial sequence
<220> FEATURE:
<223> OTHER INFORMATION: /note="HPV probe"

<400> SEQUENCE: 19
tatgactttg cttttcggga                                                  20

<210> SEQ ID NO 20
<211> LENGTH: 20
<212> TYPE: DNA
<213> ORGANISM: Artificial sequence
<220> FEATURE:
<223> OTHER INFORMATION: /note="HPV probe"

<400> SEQUENCE: 20
tatgactttg cttttcggga                                                  20

<210> SEQ ID NO 21
<211> LENGTH: 23
<212> TYPE: DNA
<213> ORGANISM: Artificial sequence
<220> FEATURE:
<223> OTHER INFORMATION: /note="HPV Primer"

<400> SEQUENCE: 21
cagaggagga ggatgaaata gta                                              23

<210> SEQ ID NO 22
<211> LENGTH: 25
<212> TYPE: DNA
<213> ORGANISM: Artificial sequence
<220> FEATURE:
<223> OTHER INFORMATION: /note="HPV Primer"

<400> SEQUENCE: 22
gcacaaccga agcgtagagt cacac                                            25

<210> SEQ ID NO 23
<211> LENGTH: 24
<212> TYPE: DNA
<213> ORGANISM: Artificial sequence
<220> FEATURE:
<223> OTHER INFORMATION: /note="HPV probe"

<400> SEQUENCE: 23
tggacaagca gaaccggaca gagc                                             24

<210> SEQ ID NO 24
<211> LENGTH: 22

-continued

```
<212> TYPE: DNA
<213> ORGANISM: Artificial sequence
<220> FEATURE:
<223> OTHER INFORMATION: /note="HPV Primer"

<400> SEQUENCE: 24
cagaggagga ggatgaaata ga                                          22

<210> SEQ ID NO 25
<211> LENGTH: 22
<212> TYPE: DNA
<213> ORGANISM: Artificial sequence
<220> FEATURE:
<223> OTHER INFORMATION: /note="HPV Primer"

<400> SEQUENCE: 25
gcacaaccga agcgtagagt ca                                          22

<210> SEQ ID NO 26
<211> LENGTH: 24
<212> TYPE: DNA
<213> ORGANISM: Artificial sequence
<220> FEATURE:
<223> OTHER INFORMATION: /note="HPV probe"

<400> SEQUENCE: 26
agcagaaccg gacagagccc atta                                        24

<210> SEQ ID NO 27
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 27
acgatgaaat agatggagtt                                             20

<210> SEQ ID NO 28
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 28
cacggacaca caaaggacag                                             20

<210> SEQ ID NO 29
<211> LENGTH: 20
<212> TYPE: DNA
<213> ORGANISM: Artificial sequence
<220> FEATURE:
<223> OTHER INFORMATION: /note="HPV probe"

<400> SEQUENCE: 29
agccgaacca caacgtcaca                                             20

<210> SEQ ID NO 30
<211> LENGTH: 22
<212> TYPE: DNA
<213> ORGANISM: Artificial sequence
<220> FEATURE:
<223> OTHER INFORMATION: /note="HPV Primer"

<400> SEQUENCE: 30
gaaaacgatg aaatagatgg ag                                          22
```

<210> SEQ ID NO 31
<211> LENGTH: 24
<212> TYPE: DNA
<213> ORGANISM: Artificial sequence
<220> FEATURE:
<223> OTHER INFORMATION: /note="HPV Primer"

<400> SEQUENCE: 31
acaccacgga cacacaaagg acag                                           24

<210> SEQ ID NO 32
<211> LENGTH: 21
<212> TYPE: DNA
<213> ORGANISM: Artificial sequence
<220> FEATURE:
<223> OTHER INFORMATION: /note="HPV probe"

<400> SEQUENCE: 32
gaaccacaac gtcacacaat g                                              21

<210> SEQ ID NO 33
<211> LENGTH: 21
<212> TYPE: DNA
<213> ORGANISM: Artificial sequence
<220> FEATURE:
<223> OTHER INFORMATION: /note="HPV probe"

<400> SEQUENCE: 33
gaaccacaac gtcacacaat g                                              21

<210> SEQ ID NO 34
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 34
ttccggttga ccttctatgt                                                20

<210> SEQ ID NO 35
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 35
ggtcgtctgc tgagctttct                                                20

<210> SEQ ID NO 36
<211> LENGTH: 21
<212> TYPE: DNA
<213> ORGANISM: Artificial sequence
<220> FEATURE:
<223> OTHER INFORMATION: /note="HPV Primer"

<400> SEQUENCE: 36
gcaagacata gaaataacct g                                              21

<210> SEQ ID NO 37
<211> LENGTH: 18
<212> TYPE: DNA
<213> ORGANISM: Artificial sequence
<220> FEATURE:
<223> OTHER INFORMATION: /note="HPV Primer"

```
<400> SEQUENCE: 37
acccagtgtt agttagtt                                                  18

<210> SEQ ID NO 38
<211> LENGTH: 20
<212> TYPE: DNA
<213> ORGANISM: Artificial sequence
<220> FEATURE:
<223> OTHER INFORMATION: /note="HPV probe"

<400> SEQUENCE: 38
tgcaagacag tattggaact                                                20

<210> SEQ ID NO 39
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 39
ggaaataccc tacgatgaac                                                20

<210> SEQ ID NO 40
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 40
ggacacaacg gtctttgaca                                                20

<210> SEQ ID NO 41
<211> LENGTH: 24
<212> TYPE: DNA
<213> ORGANISM: Artificial sequence
<220> FEATURE:
<223> OTHER INFORMATION: /note="HPV probe"

<400> SEQUENCE: 41
atagggacga cacaccacac ggag                                           24

<210> SEQ ID NO 42
<211> LENGTH: 22
<212> TYPE: DNA
<213> ORGANISM: Artificial sequence
<220> FEATURE:
<223> OTHER INFORMATION: /note="HPV Primer"

<400> SEQUENCE: 42
ggaaataccc tacgatgaac ta                                             22

<210> SEQ ID NO 43
<211> LENGTH: 22
<212> TYPE: DNA
<213> ORGANISM: Artificial sequence
<220> FEATURE:
<223> OTHER INFORMATION: /note="HPV Primer"

<400> SEQUENCE: 43
ctggacacaa cggtctttga ca                                             22

<210> SEQ ID NO 44
<211> LENGTH: 22
```

```
<212> TYPE: DNA
<213> ORGANISM: Artificial sequence
<220> FEATURE:
<223> OTHER INFORMATION: /note="HPV probe"

<400> SEQUENCE: 44
tagggacgac acaccacacg ga                                              22

<210> SEQ ID NO 45
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 45
actgacctcc actgttatga                                                 20

<210> SEQ ID NO 46
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 46
tatctacttg tgtgctctgt                                                 20

<210> SEQ ID NO 47
<211> LENGTH: 22
<212> TYPE: DNA
<213> ORGANISM: Artificial sequence
<220> FEATURE:
<223> OTHER INFORMATION: /note="HPV probe"

<400> SEQUENCE: 47
gacaagcaga accggacaca tc                                              22

<210> SEQ ID NO 48
<211> LENGTH: 24
<212> TYPE: DNA
<213> ORGANISM: Artificial sequence
<220> FEATURE:
<223> OTHER INFORMATION: /note="HPV Primer"

<400> SEQUENCE: 48
tgacctccac tgttatgagc aatt                                            24

<210> SEQ ID NO 49
<211> LENGTH: 26
<212> TYPE: DNA
<213> ORGANISM: Artificial sequence
<220> FEATURE:
<223> OTHER INFORMATION: /note="HPV Primer"

<400> SEQUENCE: 49
tgcgaatatc tacttgtgtg ctctgt                                          26

<210> SEQ ID NO 50
<211> LENGTH: 26
<212> TYPE: DNA
<213> ORGANISM: Artificial sequence
<220> FEATURE:
<223> OTHER INFORMATION: /note="HPV probe"

<400> SEQUENCE: 50
ggacaagcag aaccggacac atccaa                                          26
```

```
<210> SEQ ID NO 51
<211> LENGTH: 26
<212> TYPE: DNA
<213> ORGANISM: Artificial sequence
<220> FEATURE:
<223> OTHER INFORMATION: /note="HPV probe"

<400> SEQUENCE: 51
ggacaagcag aaccggacac atccaa                                            26

<210> SEQ ID NO 52
<211> LENGTH: 18
<212> TYPE: DNA
<213> ORGANISM: Artificial sequence
<220> FEATURE:
<223> OTHER INFORMATION: /note="HPV Primer"

<400> SEQUENCE: 52
actgacctcc actgttat                                                     18

<210> SEQ ID NO 53
<211> LENGTH: 21
<212> TYPE: DNA
<213> ORGANISM: Artificial sequence
<220> FEATURE:
<223> OTHER INFORMATION: /note="HPV Primer"

<400> SEQUENCE: 53
cacgattcca aatgagccca t                                                 21

<210> SEQ ID NO 54
<211> LENGTH: 22
<212> TYPE: DNA
<213> ORGANISM: Artificial sequence
<220> FEATURE:
<223> OTHER INFORMATION: /note="HPV Primer"

<400> SEQUENCE: 54
tatcctgaac caactgacct at                                                22

<210> SEQ ID NO 55
<211> LENGTH: 19
<212> TYPE: DNA
<213> ORGANISM: Artificial sequence
<220> FEATURE:
<223> OTHER INFORMATION: /note="HPV Primer"

<400> SEQUENCE: 55
ttgacacata aacgaactg                                                    19

<210> SEQ ID NO 56
<211> LENGTH: 19
<212> TYPE: DNA
<213> ORGANISM: Artificial sequence
<220> FEATURE:
<223> OTHER INFORMATION: /note="HPV probe"

<400> SEQUENCE: 56
cagatggaca agcacaacc                                                    19

<210> SEQ ID NO 57
<211> LENGTH: 20
<212> TYPE: DNA
<213> ORGANISM: Artificial sequence
<220> FEATURE:
<223> OTHER INFORMATION: /note="HPV Primer"
```

```
<400> SEQUENCE: 57
tcctgaacca actgacctat                                          20

<210> SEQ ID NO 58
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 58
cccataagta gttgctgtat                                          20

<210> SEQ ID NO 59
<211> LENGTH: 23
<212> TYPE: DNA
<213> ORGANISM: Artificial sequence
<220> FEATURE:
<223> OTHER INFORMATION: /note="HPV probe"

<400> SEQUENCE: 59
ggacaagcac aaccagccac agc                                      23

<210> SEQ ID NO 60
<211> LENGTH: 23
<212> TYPE: DNA
<213> ORGANISM: Artificial sequence
<220> FEATURE:
<223> OTHER INFORMATION: /note="HPV probe"

<400> SEQUENCE: 60
ggacaagcac aaccagccac agc                                      23

<210> SEQ ID NO 61
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 61
gacctttgtg tcctcaagaa                                          20

<210> SEQ ID NO 62
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 62
aggtcagttg gttcaggata                                          20

<210> SEQ ID NO 63
<211> LENGTH: 21
<212> TYPE: DNA
<213> ORGANISM: Artificial sequence
<220> FEATURE:
<223> OTHER INFORMATION: /note="HPV probe"

<400> SEQUENCE: 63
agaaactgca ctgtgacgtg t                                        21

<210> SEQ ID NO 64
<211> LENGTH: 20
```

```
<212> TYPE: DNA
<213> ORGANISM: Artificial sequence
<220> FEATURE:
<223> OTHER INFORMATION: /note="HPV Primer"

<400> SEQUENCE: 64
attacagcgg agtgaggtat                                                     20

<210> SEQ ID NO 65
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 65
gtctttgctt ttcaactgga                                                     20

<210> SEQ ID NO 66
<211> LENGTH: 20
<212> TYPE: DNA
<213> ORGANISM: Artificial sequence
<220> FEATURE:
<223> OTHER INFORMATION: /note="HPV probe"

<400> SEQUENCE: 66
atagagaagg ccagccatat                                                     20

<210> SEQ ID NO 67
<211> LENGTH: 22
<212> TYPE: DNA
<213> ORGANISM: Artificial sequence
<220> FEATURE:
<223> OTHER INFORMATION: /note="HPV Primer"

<400> SEQUENCE: 67
tcagaggagg aggaagatac ta                                                  22

<210> SEQ ID NO 68
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 68
gattatgctc tctgtgaaca                                                     20

<210> SEQ ID NO 69
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 69
cccgaggcaa ctgacctata                                                     20

<210> SEQ ID NO 70
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 70
gtcaatgtgt gtgctctgta                                                     20
```

<210> SEQ ID NO 71
<211> LENGTH: 25
<212> TYPE: DNA
<213> ORGANISM: Artificial sequence
<220> FEATURE:
<223> OTHER INFORMATION: /note="HPV probe"

<400> SEQUENCE: 71
gacaagcaaa accagacacc tccaa                                              25

<210> SEQ ID NO 72
<211> LENGTH: 20
<212> TYPE: DNA
<213> ORGANISM: Artificial sequence
<220> FEATURE:
<223> OTHER INFORMATION: /note="HPV probe"

<400> SEQUENCE: 72
gacaagcaaa accagacacc                                                    20

<210> SEQ ID NO 73
<211> LENGTH: 22
<212> TYPE: DNA
<213> ORGANISM: Artificial sequence
<220> FEATURE:
<223> OTHER INFORMATION: /note="HPV Primer"

<400> SEQUENCE: 73
ttgtgtgagg tgctggaaga at                                                 22

<210> SEQ ID NO 74
<211> LENGTH: 18
<212> TYPE: DNA
<213> ORGANISM: Artificial sequence
<220> FEATURE:
<223> OTHER INFORMATION: /note="HPV Primer"

<400> SEQUENCE: 74
ccctctcttc taatgttt                                                      18

<210> SEQ ID NO 75
<211> LENGTH: 20
<212> TYPE: DNA
<213> ORGANISM: Artificial sequence
<220> FEATURE:
<223> OTHER INFORMATION: /note="HPV probe"

<400> SEQUENCE: 75
gtgcctacgc tttttatcta                                                    20

<210> SEQ ID NO 76
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 76
gtgcctacgc tttttatcta                                                    20

<210> SEQ ID NO 77
<211> LENGTH: 22
<212> TYPE: DNA
<213> ORGANISM: Artificial sequence
<220> FEATURE:
<223> OTHER INFORMATION: /note="HPV Primer"

```
<400> SEQUENCE: 77
ggggtctcca acactctgaa ca                                          22

<210> SEQ ID NO 78
<211> LENGTH: 18
<212> TYPE: DNA
<213> ORGANISM: Artificial sequence
<220> FEATURE:
<223> OTHER INFORMATION: /note="HPV probe"

<400> SEQUENCE: 78
tgcaaacaag cgatttca                                               18

<210> SEQ ID NO 79
<211> LENGTH: 18
<212> TYPE: DNA
<213> ORGANISM: Artificial sequence
<220> FEATURE:
<223> OTHER INFORMATION: /note="HPV Primer"

<400> SEQUENCE: 79
tcaggcgttg gagacatc                                               18

<210> SEQ ID NO 80
<211> LENGTH: 18
<212> TYPE: DNA
<213> ORGANISM: Artificial sequence
<220> FEATURE:
<223> OTHER INFORMATION: /note="HPV Primer"

<400> SEQUENCE: 80
agcaatcgta agcacact                                               18

<210> SEQ ID NO 81
<211> LENGTH: 18
<212> TYPE: DNA
<213> ORGANISM: Artificial sequence
<220> FEATURE:
<223> OTHER INFORMATION: /note="HPV Primer"

<400> SEQUENCE: 81
tctgtgcatg aaatcgaa                                               18

<210> SEQ ID NO 82
<211> LENGTH: 18
<212> TYPE: DNA
<213> ORGANISM: Artificial sequence
<220> FEATURE:
<223> OTHER INFORMATION: /note="HPV Primer"

<400> SEQUENCE: 82
agcacacttt acatactg                                               18

<210> SEQ ID NO 83
<211> LENGTH: 18
<212> TYPE: DNA
<213> ORGANISM: Artificial sequence
<220> FEATURE:
<223> OTHER INFORMATION: /note="HPV probe"

<400> SEQUENCE: 83
tgaaatgcgt tgaatgca                                               18

<210> SEQ ID NO 84
<211> LENGTH: 22
```

```
<212> TYPE: DNA
<213> ORGANISM: Artificial sequence
<220> FEATURE:
<223> OTHER INFORMATION: /note="HPV probe"

<400> SEQUENCE: 84
ttgcagcgat ctgaggtata tg                                              22

<210> SEQ ID NO 85
<211> LENGTH: 18
<212> TYPE: DNA
<213> ORGANISM: Artificial sequence
<220> FEATURE:
<223> OTHER INFORMATION: /note="HPV Primer"

<400> SEQUENCE: 85
tacactgctg gacaacat                                                   18

<210> SEQ ID NO 86
<211> LENGTH: 18
<212> TYPE: DNA
<213> ORGANISM: Artificial sequence
<220> FEATURE:
<223> OTHER INFORMATION: /note="HPV Primer"

<400> SEQUENCE: 86
tcatcttctg agctgtct                                                   18

<210> SEQ ID NO 87
<211> LENGTH: 21
<212> TYPE: DNA
<213> ORGANISM: Artificial sequence
<220> FEATURE:
<223> OTHER INFORMATION: /note="HPV Primer"

<400> SEQUENCE: 87
tacactgctg gacaacatgc a                                               21

<210> SEQ ID NO 88
<211> LENGTH: 23
<212> TYPE: DNA
<213> ORGANISM: Artificial sequence
<220> FEATURE:
<223> OTHER INFORMATION: /note="HPV Primer"

<400> SEQUENCE: 88
gtcacatcca cagcaacagg tca                                             23

<210> SEQ ID NO 89
<211> LENGTH: 20
<212> TYPE: DNA
<213> ORGANISM: Artificial sequence
<220> FEATURE:
<223> OTHER INFORMATION: /note="HPV probe"

<400> SEQUENCE: 89
gtagggttac attgctatga                                                 20

<210> SEQ ID NO 90
<211> LENGTH: 22
<212> TYPE: DNA
<213> ORGANISM: Artificial sequence
<220> FEATURE:
<223> OTHER INFORMATION: /note="HPV probe"

<400> SEQUENCE: 90
gtagggttac attgctatga gc                                              22
```

```
<210> SEQ ID NO 91
<211> LENGTH: 22
<212> TYPE: DNA
<213> ORGANISM: Artificial sequence
<220> FEATURE:
<223> OTHER INFORMATION: /note="HPV Primer"

<400> SEQUENCE: 91
tgacctgttg ctgtggatgt ga                                           22

<210> SEQ ID NO 92
<211> LENGTH: 19
<212> TYPE: DNA
<213> ORGANISM: Artificial sequence
<220> FEATURE:
<223> OTHER INFORMATION: /note="HPV Primer"

<400> SEQUENCE: 92
tacctgaatc gtccgccat                                               19

<210> SEQ ID NO 93
<211> LENGTH: 18
<212> TYPE: DNA
<213> ORGANISM: Artificial sequence
<220> FEATURE:
<223> OTHER INFORMATION: /note="HPV probe"

<400> SEQUENCE: 93
atwgtgtgtc ccatctgc                                                18

<210> SEQ ID NO 94
<211> LENGTH: 19
<212> TYPE: DNA
<213> ORGANISM: Artificial sequence
<220> FEATURE:
<223> OTHER INFORMATION: /note="HPV Primer"

<400> SEQUENCE: 94
catgccataa atgtataga                                               19

<210> SEQ ID NO 95
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 95
caccgcaggc accttattaa                                              20

<210> SEQ ID NO 96
<211> LENGTH: 18
<212> TYPE: DNA
<213> ORGANISM: Artificial sequence
<220> FEATURE:
<223> OTHER INFORMATION: /note="HPV probe"

<400> SEQUENCE: 96
agaattagag aattaaga                                                18

<210> SEQ ID NO 97
<211> LENGTH: 21
<212> TYPE: DNA
<213> ORGANISM: Artificial sequence
<220> FEATURE:
<223> OTHER INFORMATION: /note="HPV Primer"
```

<400> SEQUENCE: 97
gcagacgacc actacagcaa a                                              21

<210> SEQ ID NO 98
<211> LENGTH: 19
<212> TYPE: DNA
<213> ORGANISM: Artificial sequence
<220> FEATURE:
<223> OTHER INFORMATION: /note="HPV Primer"

<400> SEQUENCE: 98
acaccgagtc cgagtaata                                                 19

<210> SEQ ID NO 99
<211> LENGTH: 19
<212> TYPE: DNA
<213> ORGANISM: Artificial sequence
<220> FEATURE:
<223> OTHER INFORMATION: /note="HPV probe"

<400> SEQUENCE: 99
atagggacgg ggaaccact                                                 19

<210> SEQ ID NO 100
<211> LENGTH: 19
<212> TYPE: DNA
<213> ORGANISM: Artificial sequence
<220> FEATURE:
<223> OTHER INFORMATION: /note="HPV Primer"

<400> SEQUENCE: 100
tattactcgg actcggtgt                                                 19

<210> SEQ ID NO 101
<211> LENGTH: 21
<212> TYPE: DNA
<213> ORGANISM: Artificial sequence
<220> FEATURE:
<223> OTHER INFORMATION: /note="HPV Primer"

<400> SEQUENCE: 101
cttgggtttc tcttcgtgtt a                                              21

<210> SEQ ID NO 102
<211> LENGTH: 20
<212> TYPE: DNA
<213> ORGANISM: Artificial sequence
<220> FEATURE:
<223> OTHER INFORMATION: /note="HPV probe"

<400> SEQUENCE: 102
ggaccacaaa acgggaggac                                                20

<210> SEQ ID NO 103
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 103
gaaatagatg aacccgacca                                                20

<210> SEQ ID NO 104
<211> LENGTH: 20

```
<212> TYPE: DNA
<213> ORGANISM: Artificial sequence
<220> FEATURE:
<223> OTHER INFORMATION: /note="HPV Primer"

<400> SEQUENCE: 104
gcacaccacg gacacacaaa                                            20

<210> SEQ ID NO 105
<211> LENGTH: 24
<212> TYPE: DNA
<213> ORGANISM: Artificial sequence
<220> FEATURE:
<223> OTHER INFORMATION: /note="HPV probe"

<400> SEQUENCE: 105
tagccagacg ggatgaacca cagc                                       24

<210> SEQ ID NO 106
<211> LENGTH: 21
<212> TYPE: DNA
<213> ORGANISM: Artificial sequence
<220> FEATURE:
<223> OTHER INFORMATION: /note="HPV Primer"

<400> SEQUENCE: 106
aaccattgaa cccagcagaa a                                          21

<210> SEQ ID NO 107
<211> LENGTH: 22
<212> TYPE: DNA
<213> ORGANISM: Artificial sequence
<220> FEATURE:
<223> OTHER INFORMATION: /note="HPV Primer"

<400> SEQUENCE: 107
tctttcttgc cgtgcctggt ca                                         22

<210> SEQ ID NO 108
<211> LENGTH: 20
<212> TYPE: DNA
<213> ORGANISM: Artificial sequence
<220> FEATURE:
<223> OTHER INFORMATION: /note="HPV probe"

<400> SEQUENCE: 108
gtaccgaggg cagtgtaata                                            20

<210> SEQ ID NO 109
<211> LENGTH: 21
<212> TYPE: DNA
<213> ORGANISM: Artificial sequence
<220> FEATURE:
<223> OTHER INFORMATION: /note="HPV Primer"

<400> SEQUENCE: 109
aaccattgaa cccagcagaa a                                          21

<210> SEQ ID NO 110
<211> LENGTH: 22
<212> TYPE: DNA
<213> ORGANISM: Artificial sequence
<220> FEATURE:
<223> OTHER INFORMATION: /note="HPV Primer"

<400> SEQUENCE: 110
tctttcttgc cgtgcctggt ca                                         22
```

```
<210> SEQ ID NO 111
<211> LENGTH: 24
<212> TYPE: DNA
<213> ORGANISM: Artificial sequence
<220> FEATURE:
<223> OTHER INFORMATION: /note="HPV Primer"

<400> SEQUENCE: 111
gaaaccattg aacccagcag aaaa                                          24

<210> SEQ ID NO 112
<211> LENGTH: 24
<212> TYPE: DNA
<213> ORGANISM: Artificial sequence
<220> FEATURE:
<223> OTHER INFORMATION: /note="HPV Primer"

<400> SEQUENCE: 112
ttgctatact tgtgtttccc tacg                                          24

<210> SEQ ID NO 113
<211> LENGTH: 20
<212> TYPE: DNA
<213> ORGANISM: Artificial sequence
<220> FEATURE:
<223> OTHER INFORMATION: /note="HPV probe"

<400> SEQUENCE: 113
gtaccgaggg cagtgtaata                                               20

<210> SEQ ID NO 114
<211> LENGTH: 20
<212> TYPE: DNA
<213> ORGANISM: Artificial sequence
<220> FEATURE:
<223> OTHER INFORMATION: /note="HPV probe"

<400> SEQUENCE: 114
ggacaaacga agatttcaca                                               20

<210> SEQ ID NO 115
<211> LENGTH: 25
<212> TYPE: DNA
<213> ORGANISM: Artificial sequence
<220> FEATURE:
<223> OTHER INFORMATION: /note="HPV Primer"

<400> SEQUENCE: 115
gttgacctgt tgtgttacca gcaat                                         25

<210> SEQ ID NO 116
<211> LENGTH: 24
<212> TYPE: DNA
<213> ORGANISM: Artificial sequence
<220> FEATURE:
<223> OTHER INFORMATION: /note="HPV Primer"

<400> SEQUENCE: 116
caccacggac acacaaagga caag                                          24

<210> SEQ ID NO 117
<211> LENGTH: 22
<212> TYPE: DNA
<213> ORGANISM: Artificial sequence
<220> FEATURE:
<223> OTHER INFORMATION: /note="HPV Primer"
```

<400> SEQUENCE: 117
ctgttgacct gttgtgttac ga                                    22

<210> SEQ ID NO 118
<211> LENGTH: 22
<212> TYPE: DNA
<213> ORGANISM: Artificial sequence
<220> FEATURE:
<223> OTHER INFORMATION: /note="HPV Primer"

<400> SEQUENCE: 118
ccacggacac acaaaggaca ag                                    22

<210> SEQ ID NO 119
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 119
gttgacctgt tgtgttacga                                       20

<210> SEQ ID NO 120
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 120
acggacacac aaaggacaag                                       20

<210> SEQ ID NO 121
<211> LENGTH: 22
<212> TYPE: DNA
<213> ORGANISM: Artificial sequence
<220> FEATURE:
<223> OTHER INFORMATION: /note="HPV probe"

<400> SEQUENCE: 121
gagtcagagg aggaaaacga tg                                    22

<210> SEQ ID NO 122
<211> LENGTH: 25
<212> TYPE: DNA
<213> ORGANISM: Artificial sequence
<220> FEATURE:
<223> OTHER INFORMATION: /note="HPV probe"

<400> SEQUENCE: 122
aggaaaacga tgaagcagat ggagt                                 25

<210> SEQ ID NO 123
<211> LENGTH: 25
<212> TYPE: DNA
<213> ORGANISM: Artificial sequence
<220> FEATURE:
<223> OTHER INFORMATION: /note="HPV probe"

<400> SEQUENCE: 123
acaactacca gcccgacgag ccgaa                                 25

<210> SEQ ID NO 124
<211> LENGTH: 20

```
<212> TYPE: DNA
<213> ORGANISM: Artificial sequence
<220> FEATURE:
<223> OTHER INFORMATION: /note="HPV Primer"

<400> SEQUENCE: 124
ggaggaggat gaagtagata                                               20

<210> SEQ ID NO 125
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 125
gcccattaac atctgctgta                                               20

<210> SEQ ID NO 126
<211> LENGTH: 23
<212> TYPE: DNA
<213> ORGANISM: Artificial sequence
<220> FEATURE:
<223> OTHER INFORMATION: /note="HPV Primer"

<400> SEQUENCE: 126
agaggaggag gatgaagtag ata                                           23

<210> SEQ ID NO 127
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 127
acgggcaaac caggcttagt                                               20

<210> SEQ ID NO 128
<211> LENGTH: 20
<212> TYPE: DNA
<213> ORGANISM: Artificial sequence
<220> FEATURE:
<223> OTHER INFORMATION: /note="HPV probe"

<400> SEQUENCE: 128
gcaggtgttc aagtgtagta                                               20

<210> SEQ ID NO 129
<211> LENGTH: 24
<212> TYPE: DNA
<213> ORGANISM: Artificial sequence
<220> FEATURE:
<223> OTHER INFORMATION: /note="HPV probe"

<400> SEQUENCE: 129
tggcagtgga aagcagtgga gaca                                          24

<210> SEQ ID NO 130
<211> LENGTH: 24
<212> TYPE: DNA
<213> ORGANISM: Artificial sequence
<220> FEATURE:
<223> OTHER INFORMATION: /note="HPV Primer"

<400> SEQUENCE: 130
ttggggtgct ggagacaaac atct                                          24
```

<210> SEQ ID NO 131
<211> LENGTH: 24
<212> TYPE: DNA
<213> ORGANISM: Artificial sequence
<220> FEATURE:
<223> OTHER INFORMATION: /note="HPV Primer"

<400> SEQUENCE: 131
ttcatcctca tcctcatcct ctga                                        24

<210> SEQ ID NO 132
<211> LENGTH: 22
<212> TYPE: DNA
<213> ORGANISM: Artificial sequence
<220> FEATURE:
<223> OTHER INFORMATION: /note="HPV Primer"

<400> SEQUENCE: 132
tggggtgctg gagacaaaca tc                                          22

<210> SEQ ID NO 133
<211> LENGTH: 22
<212> TYPE: DNA
<213> ORGANISM: Artificial sequence
<220> FEATURE:
<223> OTHER INFORMATION: /note="HPV Primer"

<400> SEQUENCE: 133
catcctcatc ctcatcctct ga                                          22

<210> SEQ ID NO 134
<211> LENGTH: 22
<212> TYPE: DNA
<213> ORGANISM: Artificial sequence
<220> FEATURE:
<223> OTHER INFORMATION: /note="HPV Primer"

<400> SEQUENCE: 134
ttggggtgct ggagacaaac at                                          22

<210> SEQ ID NO 135
<211> LENGTH: 22
<212> TYPE: DNA
<213> ORGANISM: Artificial sequence
<220> FEATURE:
<223> OTHER INFORMATION: /note="HPV Primer"

<400> SEQUENCE: 135
ccacaaactt acactcacaa ca                                          22

<210> SEQ ID NO 136
<211> LENGTH: 23
<212> TYPE: DNA
<213> ORGANISM: Artificial sequence
<220> FEATURE:
<223> OTHER INFORMATION: /note="HPV probe"

<400> SEQUENCE: 136
aaagtaccaa cgctgcaaga cgt                                         23

<210> SEQ ID NO 137
<211> LENGTH: 24
<212> TYPE: DNA
<213> ORGANISM: Artificial sequence
<220> FEATURE:
<223> OTHER INFORMATION: /note="HPV probe"

```
<400> SEQUENCE: 137
agaactaaca cctcaaacag aaat                                         24

<210> SEQ ID NO 138
<211> LENGTH: 22
<212> TYPE: DNA
<213> ORGANISM: Artificial sequence
<220> FEATURE:
<223> OTHER INFORMATION: /note="HPV probe"

<400> SEQUENCE: 138
agtaccaacg ctgcaagacg tt                                           22

<210> SEQ ID NO 139
<211> LENGTH: 22
<212> TYPE: DNA
<213> ORGANISM: Artificial sequence
<220> FEATURE:
<223> OTHER INFORMATION: /note="HPV Primer"

<400> SEQUENCE: 139
ttggacagct cagaggatga gg                                           22

<210> SEQ ID NO 140
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 140
gattttcctt atgcagtgtg                                              20

<210> SEQ ID NO 141
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 141
gacatctgta gcaccttatt                                              20

<210> SEQ ID NO 142
<211> LENGTH: 20
<212> TYPE: DNA
<213> ORGANISM: Artificial sequence
<220> FEATURE:
<223> OTHER INFORMATION: /note="HPV probe"

<400> SEQUENCE: 142
gactattcag tgtatggagc                                              20

<210> SEQ ID NO 143
<211> LENGTH: 22
<212> TYPE: DNA
<213> ORGANISM: Artificial sequence
<220> FEATURE:
<223> OTHER INFORMATION: /note="HPV probe"

<400> SEQUENCE: 143
caactgayct myactgttat ga                                           22

<210> SEQ ID NO 144
<211> LENGTH: 22
```

```
<212> TYPE: DNA
<213> ORGANISM: Artificial sequence
<220> FEATURE:
<223> OTHER INFORMATION: /note="HPV probe"

<400> SEQUENCE: 144
caactgayct myactgttat ga                                          22

<210> SEQ ID NO 145
<211> LENGTH: 24
<212> TYPE: DNA
<213> ORGANISM: Artificial sequence
<220> FEATURE:
<223> OTHER INFORMATION: /note="HPV probe"

<400> SEQUENCE: 145
gaamcaactg acctaywctg ctat                                        24

<210> SEQ ID NO 146
<211> LENGTH: 24
<212> TYPE: DNA
<213> ORGANISM: Artificial sequence
<220> FEATURE:
<223> OTHER INFORMATION: /note="HPV probe"

<400> SEQUENCE: 146
gaamcaactg acctaywctg ctat                                        24

<210> SEQ ID NO 147
<211> LENGTH: 18
<212> TYPE: DNA
<213> ORGANISM: Artificial sequence
<220> FEATURE:
<223> OTHER INFORMATION: /note="HPV probe"

<400> SEQUENCE: 147
aagacattat tcagactc                                               18

<210> SEQ ID NO 148
<211> LENGTH: 18
<212> TYPE: DNA
<213> ORGANISM: Artificial sequence
<220> FEATURE:
<223> OTHER INFORMATION: /note="HPV probe"

<400> SEQUENCE: 148
aagacattat tcagactc                                               18

<210> SEQ ID NO 149
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 149
aatggcattt gttggggtaa                                             20

<210> SEQ ID NO 150
<211> LENGTH: 19
<212> TYPE: DNA
<213> ORGANISM: Artificial sequence
<220> FEATURE:
<223> OTHER INFORMATION: /note="HPV Primer"

<400> SEQUENCE: 150
tcatattcct ccccatgtc                                              19
```

<210> SEQ ID NO 151
<211> LENGTH: 22
<212> TYPE: DNA
<213> ORGANISM: Artificial sequence
<220> FEATURE:
<223> OTHER INFORMATION: /note="HPV probe"

<400> SEQUENCE: 151
ttgttactgt tgttgatact ac                                          22

<210> SEQ ID NO 152
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 152
aatggcattt gttggsrhaa                                             20

<210> SEQ ID NO 153
<211> LENGTH: 19
<212> TYPE: DNA
<213> ORGANISM: Artificial sequence
<220> FEATURE:
<223> OTHER INFORMATION: /note="HPV Primer"

<400> SEQUENCE: 153
tcatattcct cmmcatgdc                                              19

<210> SEQ ID NO 154
<211> LENGTH: 22
<212> TYPE: DNA
<213> ORGANISM: Artificial sequence
<220> FEATURE:
<223> OTHER INFORMATION: /note="HPV probe"

<400> SEQUENCE: 154
ttgttactgt tgttgatacy ac                                          22

<210> SEQ ID NO 155
<211> LENGTH: 22
<212> TYPE: DNA
<213> ORGANISM: Artificial sequence
<220> FEATURE:
<223> OTHER INFORMATION: /note="HPV probe"

<400> SEQUENCE: 155
ttgttactgt tgttgatacc ac                                          22

<210> SEQ ID NO 156
<211> LENGTH: 20
<212> TYPE: DNA
<213> ORGANISM: Artificial sequence
<220> FEATURE:
<223> OTHER INFORMATION: /note="HPV Primer"
<220> FEATURE:
<221> NAME/KEY: misc_feature
<222> LOCATION: (17)..(17)
<223> OTHER INFORMATION: "n" represents inosine
<220> FEATURE:
<221> NAME/KEY: misc_feature
<222> LOCATION: (18)..(18)
<223> OTHER INFORMATION: "n" represents inosine

<400> SEQUENCE: 156
aatggcattt gttggsnnaa                                             20

<210> SEQ ID NO 157
<211> LENGTH: 20
<212> TYPE: DNA
<213> ORGANISM: Artificial sequence
<220> FEATURE:
<223> OTHER INFORMATION: /note="HPV Primer"
<220> FEATURE:
<221> NAME/KEY: misc_feature
<222> LOCATION: (16)..(16)
<223> OTHER INFORMATION: "n" represents inosine
<220> FEATURE:
<221> NAME/KEY: misc_feature
<222> LOCATION: (17)..(17)
<223> OTHER INFORMATION: "n" represents inosine

<400> SEQUENCE: 157
aatggcattt gttggnnhaa                                       20

<210> SEQ ID NO 158
<211> LENGTH: 20
<212> TYPE: DNA
<213> ORGANISM: Artificial sequence
<220> FEATURE:
<223> OTHER INFORMATION: /note="HPV Primer"
<220> FEATURE:
<221> NAME/KEY: misc_feature
<222> LOCATION: (16)..(16)
<223> OTHER INFORMATION: "n" represents inosine
<220> FEATURE:
<221> NAME/KEY: misc_feature
<222> LOCATION: (18)..(18)
<223> OTHER INFORMATION: "n" represents inosine

<400> SEQUENCE: 158
aatggcattt gttggnrnaa                                       20

<210> SEQ ID NO 159
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 159
aatggcattt gttggggtaa                                       20

<210> SEQ ID NO 160
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 160
aatggcattt gttggggaaa                                       20

<210> SEQ ID NO 161
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 161
aatggcattt gttggcataa                                       20

<210> SEQ ID NO 162
<211> LENGTH: 20

```
<212> TYPE: DNA
<213> ORGANISM: Artificial sequence
<220> FEATURE:
<223> OTHER INFORMATION: /note="HPV Primer"

<400> SEQUENCE: 162
aatggcattt gttggggcaa                                          20

<210> SEQ ID NO 163
<211> LENGTH: 20
<212> TYPE: DNA
<213> ORGANISM: Artificial sequence
<220> FEATURE:
<223> OTHER INFORMATION: /note="HPV Primer"

<400> SEQUENCE: 163
aatggcattt gttggcacaa                                          20

<210> SEQ ID NO 164
<211> LENGTH: 19
<212> TYPE: DNA
<213> ORGANISM: Artificial sequence
<220> FEATURE:
<223> OTHER INFORMATION: /note="HPV Primer"
<220> FEATURE:
<221> NAME/KEY: misc_feature
<222> LOCATION: (13)..(13)
<223> OTHER INFORMATION: "n" represents inosine
<220> FEATURE:
<221> NAME/KEY: misc_feature
<222> LOCATION: (18)..(18)
<223> OTHER INFORMATION: "n" represents inosine

<400> SEQUENCE: 164
tcatattcct cmncatgnc                                           19

<210> SEQ ID NO 165
<211> LENGTH: 19
<212> TYPE: DNA
<213> ORGANISM: Artificial sequence
<220> FEATURE:
<223> OTHER INFORMATION: /note="HPV Primer"
<220> FEATURE:
<221> NAME/KEY: misc_feature
<222> LOCATION: (18)..(18)
<223> OTHER INFORMATION: "n" represents inosine

<400> SEQUENCE: 165
tcatattcct caacatgnc                                           19

<210> SEQ ID NO 166
<211> LENGTH: 19
<212> TYPE: DNA
<213> ORGANISM: Artificial sequence
<220> FEATURE:
<223> OTHER INFORMATION: /note="HPV Primer"
<220> FEATURE:
<221> NAME/KEY: misc_feature
<222> LOCATION: (12)..(12)
<223> OTHER INFORMATION: "n" represents inosine
<220> FEATURE:
<221> NAME/KEY: misc_feature
<222> LOCATION: (13)..(13)
<223> OTHER INFORMATION: "n" represents inosine

<400> SEQUENCE: 166
tcatattcct cnncatgtc                                           19

<210> SEQ ID NO 167
<211> LENGTH: 19
```

```
<212> TYPE: DNA
<213> ORGANISM: Artificial sequence
<220> FEATURE:
<223> OTHER INFORMATION: /note="HPV Primer"
<220> FEATURE:
<221> NAME/KEY: misc_feature
<222> LOCATION: (12)..(12)
<223> OTHER INFORMATION: "n" represents inosine
<220> FEATURE:
<221> NAME/KEY: misc_feature
<222> LOCATION: (13)..(13)
<223> OTHER INFORMATION: "n" represents inosine

<400> SEQUENCE: 167
tcatattcct cnncatggc                                                    19

<210> SEQ ID NO 168
<211> LENGTH: 19
<212> TYPE: DNA
<213> ORGANISM: Artificial sequence
<220> FEATURE:
<223> OTHER INFORMATION: /note="HPV Primer"
<220> FEATURE:
<221> NAME/KEY: misc_feature
<222> LOCATION: (12)..(12)
<223> OTHER INFORMATION: "n" represents inosine
<220> FEATURE:
<221> NAME/KEY: misc_feature
<222> LOCATION: (13)..(13)
<223> OTHER INFORMATION: "n" represents inosine

<400> SEQUENCE: 168
tcatattcct cnncatgac                                                    19

<210> SEQ ID NO 169
<211> LENGTH: 19
<212> TYPE: DNA
<213> ORGANISM: Artificial sequence
<220> FEATURE:
<223> OTHER INFORMATION: /note="HPV Primer"
<220> FEATURE:
<221> NAME/KEY: misc_feature
<222> LOCATION: (12)..(12)
<223> OTHER INFORMATION: "n" represents inosine
<220> FEATURE:
<221> NAME/KEY: misc_feature
<222> LOCATION: (13)..(13)
<223> OTHER INFORMATION: "n" represents inosine

<400> SEQUENCE: 169
tcatattcct cnncatgcc                                                    19

<210> SEQ ID NO 170
<211> LENGTH: 20
<212> TYPE: DNA
<213> ORGANISM: Artificial sequence
<220> FEATURE:
<223> OTHER INFORMATION: Sequence for incorporation into NASBA primers
      to enable hybridisation with universal ECL detection probe

<400> SEQUENCE: 170
gatgcaaggt cgcatatgag                                                   20

<210> SEQ ID NO 171
<211> LENGTH: 25
<212> TYPE: DNA
<213> ORGANISM: Artificial sequence
<220> FEATURE:
<223> OTHER INFORMATION: Promoter sequence for incorporation into NASBA
      P1 primer oligonucleotides

<400> SEQUENCE: 171
```

-continued

```
aattctaata cgactcacta taggg                                            25

<210> SEQ ID NO 172
<211> LENGTH: 31
<212> TYPE: DNA
<213> ORGANISM: Artificial sequence
<220> FEATURE:
<223> OTHER INFORMATION: Promoter sequence for incorporation into NASBA
      P1 primer oligonucleotides

<400> SEQUENCE: 172
aattctaata cgactcacta tagggagaag g                                     31

<210> SEQ ID NO 173
<211> LENGTH: 44
<212> TYPE: DNA
<213> ORGANISM: Artificial sequence
<220> FEATURE:
<223> OTHER INFORMATION: /note="HPV NASBA Primer"

<400> SEQUENCE: 173
gatgcaaggt cgcatatgag ccacaggagc gacccagaaa gtta                       44

<210> SEQ ID NO 174
<211> LENGTH: 53
<212> TYPE: DNA
<213> ORGANISM: Artificial sequence
<220> FEATURE:
<223> OTHER INFORMATION: /note="HPV NASBA Primer"

<400> SEQUENCE: 174
aattctaata cgactcacta tagggagaag gacggtttgt tgtattgctg ttc             53

<210> SEQ ID NO 175
<211> LENGTH: 40
<212> TYPE: DNA
<213> ORGANISM: Artificial sequence
<220> FEATURE:
<223> OTHER INFORMATION: /note="HPV NASBA Primer"

<400> SEQUENCE: 175
gatgcaaggt cgcatatgag ccacaggagc gacccagaaa                            40

<210> SEQ ID NO 176
<211> LENGTH: 51
<212> TYPE: DNA
<213> ORGANISM: Artificial sequence
<220> FEATURE:
<223> OTHER INFORMATION: /note="HPV NASBA Primer"

<400> SEQUENCE: 176
aattctaata cgactcacta tagggagaag gggtttgttg tattgctgtt c               51

<210> SEQ ID NO 177
<211> LENGTH: 51
<212> TYPE: DNA
<213> ORGANISM: Artificial sequence
<220> FEATURE:
<223> OTHER INFORMATION: /note="HPV NASBA Primer"

<400> SEQUENCE: 177
aattctaata cgactcacta tagggagaag gattcccatc tctatatact a               51

<210> SEQ ID NO 178
<211> LENGTH: 49
<212> TYPE: DNA
```

```
<213> ORGANISM: Artificial sequence
<220> FEATURE:
<223> OTHER INFORMATION: /note="HPV NASBA Primer"

<400> SEQUENCE: 178
aattctaata cgactcacta tagggagaag gtcacgtcgc agtaactgt                49

<210> SEQ ID NO 179
<211> LENGTH: 49
<212> TYPE: DNA
<213> ORGANISM: Artificial sequence
<220> FEATURE:
<223> OTHER INFORMATION: /note="HPV NASBA Primer"

<400> SEQUENCE: 179
aattctaata cgactcacta tagggagaag gttgcttgca gtacacaca                49

<210> SEQ ID NO 180
<211> LENGTH: 49
<212> TYPE: DNA
<213> ORGANISM: Artificial sequence
<220> FEATURE:
<223> OTHER INFORMATION: /note="HPV NASBA Primer"

<400> SEQUENCE: 180
aattctaata cgactcacta tagggagaag gtgcagtaca cacattcta                49

<210> SEQ ID NO 181
<211> LENGTH: 49
<212> TYPE: DNA
<213> ORGANISM: Artificial sequence
<220> FEATURE:
<223> OTHER INFORMATION: /note="HPV NASBA Primer"

<400> SEQUENCE: 181
aattctaata cgactcacta tagggagaag ggcagtacac acattctaa                49

<210> SEQ ID NO 182
<211> LENGTH: 38
<212> TYPE: DNA
<213> ORGANISM: Artificial sequence
<220> FEATURE:
<223> OTHER INFORMATION: /note="HPV NASBA Primer"

<400> SEQUENCE: 182
gatgcaaggt cgcatatgag acagttatgc acagagct                            38

<210> SEQ ID NO 183
<211> LENGTH: 38
<212> TYPE: DNA
<213> ORGANISM: Artificial sequence
<220> FEATURE:
<223> OTHER INFORMATION: /note="HPV NASBA Primer"

<400> SEQUENCE: 183
gatgcaaggt cgcatatgag atattagaat gtgtgtac                            38

<210> SEQ ID NO 184
<211> LENGTH: 38
<212> TYPE: DNA
<213> ORGANISM: Artificial sequence
<220> FEATURE:
<223> OTHER INFORMATION: /note="HPV NASBA Primer"

<400> SEQUENCE: 184
gatgcaaggt cgcatatgag ttagaatgtg tgtactgc                            38
```

```
<210> SEQ ID NO 185
<211> LENGTH: 38
<212> TYPE: DNA
<213> ORGANISM: Artificial sequence
<220> FEATURE:
<223> OTHER INFORMATION: /note="HPV NASBA Primer"

<400> SEQUENCE: 185
gatgcaaggt cgcatatgag gaatgtgtgt actgcaag                               38

<210> SEQ ID NO 186
<211> LENGTH: 32
<212> TYPE: DNA
<213> ORGANISM: Artificial sequence
<220> FEATURE:
<223> OTHER INFORMATION: /note="HPV molecular beacon probe"

<400> SEQUENCE: 186
cgcatgtatg actttgcttt tcgggacatg cg                                     32

<210> SEQ ID NO 187
<211> LENGTH: 32
<212> TYPE: DNA
<213> ORGANISM: Artificial sequence
<220> FEATURE:
<223> OTHER INFORMATION: /note="HPV molecular beacon probe"

<400> SEQUENCE: 187
ccagcttatg actttgcttt tcgggaagct gg                                     32

<210> SEQ ID NO 188
<211> LENGTH: 30
<212> TYPE: DNA
<213> ORGANISM: Artificial sequence
<220> FEATURE:
<223> OTHER INFORMATION: /note="HPV molecular beacon probe"

<400> SEQUENCE: 188
cacgctatga ctttgctttt cgggagcgtg                                        30

<210> SEQ ID NO 189
<211> LENGTH: 32
<212> TYPE: DNA
<213> ORGANISM: Artificial sequence
<220> FEATURE:
<223> OTHER INFORMATION: /note="HPV molecular beacon probe"

<400> SEQUENCE: 189
cgatcgtatg actttgcttt tcgggacgat cg                                     32

<210> SEQ ID NO 190
<211> LENGTH: 43
<212> TYPE: DNA
<213> ORGANISM: Artificial sequence
<220> FEATURE:
<223> OTHER INFORMATION: /note="HPV NASBA Primer"

<400> SEQUENCE: 190
gatgcaaggt cgcatatgag cagaggagga ggatgaaata gta                         43

<210> SEQ ID NO 191
<211> LENGTH: 56
<212> TYPE: DNA
<213> ORGANISM: Artificial sequence
<220> FEATURE:
<223> OTHER INFORMATION: /note="HPV NASBA Primer"
```

```
<400> SEQUENCE: 191
aattctaata cgactcacta tagggagaag ggcacaaccg aagcgtagag tcacac      56

<210> SEQ ID NO 192
<211> LENGTH: 42
<212> TYPE: DNA
<213> ORGANISM: Artificial sequence
<220> FEATURE:
<223> OTHER INFORMATION: /note="HPV NASBA Primer"

<400> SEQUENCE: 192
gatgcaaggt cgcatatgag cagaggagga ggatgaaata ga                    42

<210> SEQ ID NO 193
<211> LENGTH: 53
<212> TYPE: DNA
<213> ORGANISM: Artificial sequence
<220> FEATURE:
<223> OTHER INFORMATION: /note="HPV NASBA Primer"

<400> SEQUENCE: 193
aattctaata cgactcacta tagggagaag ggcacaaccg aagcgtagag tca         53

<210> SEQ ID NO 194
<211> LENGTH: 40
<212> TYPE: DNA
<213> ORGANISM: Artificial sequence
<220> FEATURE:
<223> OTHER INFORMATION: /note="HPV NASBA Primer"

<400> SEQUENCE: 194
gatgcaaggt cgcatatgag acgatgaaat agatggagtt                       40

<210> SEQ ID NO 195
<211> LENGTH: 51
<212> TYPE: DNA
<213> ORGANISM: Artificial sequence
<220> FEATURE:
<223> OTHER INFORMATION: /note="HPV NASBA Primer"

<400> SEQUENCE: 195
aattctaata cgactcacta tagggagaag gcacggacac acaaaggaca g           51

<210> SEQ ID NO 196
<211> LENGTH: 42
<212> TYPE: DNA
<213> ORGANISM: Artificial sequence
<220> FEATURE:
<223> OTHER INFORMATION: /note="HPV NASBA Primer"

<400> SEQUENCE: 196
gatgcaaggt cgcatatgag gaaaacgatg aaatagatgg ag                    42

<210> SEQ ID NO 197
<211> LENGTH: 55
<212> TYPE: DNA
<213> ORGANISM: Artificial sequence
<220> FEATURE:
<223> OTHER INFORMATION: /note="HPV NASBA Primer"

<400> SEQUENCE: 197
aattctaata cgactcacta tagggagaag gacaccacgg acacacaaag gacag       55

<210> SEQ ID NO 198
<211> LENGTH: 33
<212> TYPE: DNA
```

```
<213> ORGANISM: Artificial sequence
<220> FEATURE:
<223> OTHER INFORMATION: /note="HPV molecular beacon probe"

<400> SEQUENCE: 198
cgcatggaac cacaacgtca cacaatgcat gcg                                33

<210> SEQ ID NO 199
<211> LENGTH: 33
<212> TYPE: DNA
<213> ORGANISM: Artificial sequence
<220> FEATURE:
<223> OTHER INFORMATION: /note="HPV molecular beacon probe"

<400> SEQUENCE: 199
ccgtcggaac cacaacgtca cacaatgcga cgg                                33

<210> SEQ ID NO 200
<211> LENGTH: 33
<212> TYPE: DNA
<213> ORGANISM: Artificial sequence
<220> FEATURE:
<223> OTHER INFORMATION: /note="HPV molecular beacon probe"

<400> SEQUENCE: 200
cggaccgaac cacaacgtca cacaatgggt ccg                                33

<210> SEQ ID NO 201
<211> LENGTH: 33
<212> TYPE: DNA
<213> ORGANISM: Artificial sequence
<220> FEATURE:
<223> OTHER INFORMATION: /note="HPV molecular beacon probe"

<400> SEQUENCE: 201
cgatcggaac cacaacgtca cacaatgcga tcg                                33

<210> SEQ ID NO 202
<211> LENGTH: 40
<212> TYPE: DNA
<213> ORGANISM: Artificial sequence
<220> FEATURE:
<223> OTHER INFORMATION: /note="HPV NASBA Primer"

<400> SEQUENCE: 202
gatgcaaggt cgcatatgag ttccggttga ccttctatgt                         40

<210> SEQ ID NO 203
<211> LENGTH: 51
<212> TYPE: DNA
<213> ORGANISM: Artificial sequence
<220> FEATURE:
<223> OTHER INFORMATION: /note="HPV NASBA Primer"

<400> SEQUENCE: 203
aattctaata cgactcacta tagggagaag ggtcgtctg ctgagctttc t             51

<210> SEQ ID NO 204
<211> LENGTH: 41
<212> TYPE: DNA
<213> ORGANISM: Artificial sequence
<220> FEATURE:
<223> OTHER INFORMATION: /note="HPV NASBA Primer"

<400> SEQUENCE: 204
gatgcaaggt cgcatatgag gcaagacata gaaataacct g                       41
```

<210> SEQ ID NO 205
<211> LENGTH: 49
<212> TYPE: DNA
<213> ORGANISM: Artificial sequence
<220> FEATURE:
<223> OTHER INFORMATION: /note="HPV NASBA Primer"

<400> SEQUENCE: 205
aattctaata cgactcacta tagggagaag gacccagtgt tagttagtt          49

<210> SEQ ID NO 206
<211> LENGTH: 40
<212> TYPE: DNA
<213> ORGANISM: Artificial sequence
<220> FEATURE:
<223> OTHER INFORMATION: /note="HPV NASBA Primer"

<400> SEQUENCE: 206
gatgcaaggt cgcatatgag ggaaataccc tacgatgaac                    40

<210> SEQ ID NO 207
<211> LENGTH: 51
<212> TYPE: DNA
<213> ORGANISM: Artificial sequence
<220> FEATURE:
<223> OTHER INFORMATION: /note="HPV NASBA Primer"

<400> SEQUENCE: 207
aattctaata cgactcacta tagggagaag gggacacaac ggtctttgac a        51

<210> SEQ ID NO 208
<211> LENGTH: 42
<212> TYPE: DNA
<213> ORGANISM: Artificial sequence
<220> FEATURE:
<223> OTHER INFORMATION: /note="HPV NASBA Primer"

<400> SEQUENCE: 208
gatgcaaggt cgcatatgag ggaaataccc tacgatgaac ta                 42

<210> SEQ ID NO 209
<211> LENGTH: 53
<212> TYPE: DNA
<213> ORGANISM: Artificial sequence
<220> FEATURE:
<223> OTHER INFORMATION: /note="HPV NASBA Primer"

<400> SEQUENCE: 209
aattctaata cgactcacta tagggagaag gctggacaca acggtctttg aca     53

<210> SEQ ID NO 210
<211> LENGTH: 40
<212> TYPE: DNA
<213> ORGANISM: Artificial sequence
<220> FEATURE:
<223> OTHER INFORMATION: /note="HPV NASBA Primer"

<400> SEQUENCE: 210
gatgcaaggt cgcatatgag actgacctcc actgttatga                    40

<210> SEQ ID NO 211
<211> LENGTH: 51
<212> TYPE: DNA
<213> ORGANISM: Artificial sequence
<220> FEATURE:
<223> OTHER INFORMATION: /note="HPV NASBA Primer"

```
<400> SEQUENCE: 211
aattctaata cgactcacta tagggagaag gtatctactt gtgtgctctg t      51

<210> SEQ ID NO 212
<211> LENGTH: 44
<212> TYPE: DNA
<213> ORGANISM: Artificial sequence
<220> FEATURE:
<223> OTHER INFORMATION: /note="HPV NASBA Primer"

<400> SEQUENCE: 212
gatgcaaggt cgcatatgag tgacctccac tgttatgagc aatt             44

<210> SEQ ID NO 213
<211> LENGTH: 57
<212> TYPE: DNA
<213> ORGANISM: Artificial sequence
<220> FEATURE:
<223> OTHER INFORMATION: /note="HPV NASBA Primer"

<400> SEQUENCE: 213
aattctaata cgactcacta tagggagaag gtgcgaatat ctacttgtgt gctctgt   57

<210> SEQ ID NO 214
<211> LENGTH: 40
<212> TYPE: DNA
<213> ORGANISM: Artificial sequence
<220> FEATURE:
<223> OTHER INFORMATION: /note="HPV molecular beacon probe"

<400> SEQUENCE: 214
ccgaagggga caagcagaac cggacacatc caaccttcgg              40

<210> SEQ ID NO 215
<211> LENGTH: 38
<212> TYPE: DNA
<213> ORGANISM: Artificial sequence
<220> FEATURE:
<223> OTHER INFORMATION: /note="HPV molecular beacon probe"

<400> SEQUENCE: 215
ccgtcgggac aagcagaacc ggacacatcc aacgacgg                38

<210> SEQ ID NO 216
<211> LENGTH: 40
<212> TYPE: DNA
<213> ORGANISM: Artificial sequence
<220> FEATURE:
<223> OTHER INFORMATION: /note="HPV molecular beacon probe"

<400> SEQUENCE: 216
cacgtcggga caagcagaac cggacacatc caacgacgtg              40

<210> SEQ ID NO 217
<211> LENGTH: 38
<212> TYPE: DNA
<213> ORGANISM: Artificial sequence
<220> FEATURE:
<223> OTHER INFORMATION: /note="HPV molecular beacon probe"

<400> SEQUENCE: 217
cgcagcggac aagcagaacc ggacacatcc aagctgcg                38

<210> SEQ ID NO 218
<211> LENGTH: 38
<212> TYPE: DNA
```

<213> ORGANISM: Artificial sequence
<220> FEATURE:
<223> OTHER INFORMATION: /note="HPV molecular beacon probe"

<400> SEQUENCE: 218
cgatcgggac aagcagaacc ggacacatcc aacgatcg                          38

<210> SEQ ID NO 219
<211> LENGTH: 38
<212> TYPE: DNA
<213> ORGANISM: Artificial sequence
<220> FEATURE:
<223> OTHER INFORMATION: /note="HPV NASBA Primer"

<400> SEQUENCE: 219
gatgcaaggt cgcatatgag actgacctcc actgttat                          38

<210> SEQ ID NO 220
<211> LENGTH: 52
<212> TYPE: DNA
<213> ORGANISM: Artificial sequence
<220> FEATURE:
<223> OTHER INFORMATION: /note="HPV NASBA Primer"

<400> SEQUENCE: 220
aattctaata cgactcacta tagggagaag gcacgattcc aaatgagccc at          52

<210> SEQ ID NO 221
<211> LENGTH: 42
<212> TYPE: DNA
<213> ORGANISM: Artificial sequence
<220> FEATURE:
<223> OTHER INFORMATION: /note="HPV NASBA Primer"

<400> SEQUENCE: 221
gatgcaaggt cgcatatgag tatcctgaac caactgacct at                     42

<210> SEQ ID NO 222
<211> LENGTH: 50
<212> TYPE: DNA
<213> ORGANISM: Artificial sequence
<220> FEATURE:
<223> OTHER INFORMATION: /note="HPV NASBA Primer"

<400> SEQUENCE: 222
aattctaata cgactcacta tagggagaag gttgacacat aaacgaactg             50

<210> SEQ ID NO 223
<211> LENGTH: 40
<212> TYPE: DNA
<213> ORGANISM: Artificial sequence
<220> FEATURE:
<223> OTHER INFORMATION: /note="HPV NASBA Primer"

<400> SEQUENCE: 223
gatgcaaggt cgcatatgag tcctgaacca actgacctat                        40

<210> SEQ ID NO 224
<211> LENGTH: 51
<212> TYPE: DNA
<213> ORGANISM: Artificial sequence
<220> FEATURE:
<223> OTHER INFORMATION: /note="HPV NASBA Primer"

<400> SEQUENCE: 224
aattctaata cgactcacta tagggagaag gcccataagt agttgctgta t           51

<210> SEQ ID NO 225
<211> LENGTH: 35
<212> TYPE: DNA
<213> ORGANISM: Artificial sequence
<220> FEATURE:
<223> OTHER INFORMATION: /note="HPV molecular beacon probe"

<400> SEQUENCE: 225
ccaagcggac aagcacaacc agccacagcg cttgg                         35

<210> SEQ ID NO 226
<211> LENGTH: 37
<212> TYPE: DNA
<213> ORGANISM: Artificial sequence
<220> FEATURE:
<223> OTHER INFORMATION: /note="HPV molecular beacon probe"

<400> SEQUENCE: 226
ccaagcggga caagcacaac cagccacagc cgcttgg                       37

<210> SEQ ID NO 227
<211> LENGTH: 35
<212> TYPE: DNA
<213> ORGANISM: Artificial sequence
<220> FEATURE:
<223> OTHER INFORMATION: /note="HPV molecular beacon probe"

<400> SEQUENCE: 227
cccagcggac aagcacaacc agccacagcg ctggg                         35

<210> SEQ ID NO 228
<211> LENGTH: 37
<212> TYPE: DNA
<213> ORGANISM: Artificial sequence
<220> FEATURE:
<223> OTHER INFORMATION: /note="HPV molecular beacon probe"

<400> SEQUENCE: 228
ccaaagcgga caagcacaac cagccacagc gctttgg                       37

<210> SEQ ID NO 229
<211> LENGTH: 33
<212> TYPE: DNA
<213> ORGANISM: Artificial sequence
<220> FEATURE:
<223> OTHER INFORMATION: /note="HPV molecular beacon probe"

<400> SEQUENCE: 229
cctgcggaca agcacaacca gccacagcgc agg                           33

<210> SEQ ID NO 230
<211> LENGTH: 35
<212> TYPE: DNA
<213> ORGANISM: Artificial sequence
<220> FEATURE:
<223> OTHER INFORMATION: /note="HPV molecular beacon probe"

<400> SEQUENCE: 230
cgatcgggac aagcacaacc agccacagcc gatcg                         35

<210> SEQ ID NO 231
<211> LENGTH: 40
<212> TYPE: DNA
<213> ORGANISM: Artificial sequence
<220> FEATURE:
<223> OTHER INFORMATION: /note="HPV NASBA Primer"

```
<400> SEQUENCE: 231
gatgcaaggt cgcatatgag gacctttgtg tcctcaagaa                    40

<210> SEQ ID NO 232
<211> LENGTH: 51
<212> TYPE: DNA
<213> ORGANISM: Artificial sequence
<220> FEATURE:
<223> OTHER INFORMATION: /note="HPV NASBA Primer"

<400> SEQUENCE: 232
aattctaata cgactcacta tagggagaag gaggtcagtt ggttcaggat a        51

<210> SEQ ID NO 233
<211> LENGTH: 40
<212> TYPE: DNA
<213> ORGANISM: Artificial sequence
<220> FEATURE:
<223> OTHER INFORMATION: /note="HPV NASBA Primer"

<400> SEQUENCE: 233
gatgcaaggt cgcatatgag attacagcgg agtgaggtat                    40

<210> SEQ ID NO 234
<211> LENGTH: 51
<212> TYPE: DNA
<213> ORGANISM: Artificial sequence
<220> FEATURE:
<223> OTHER INFORMATION: /note="HPV NASBA Primer"

<400> SEQUENCE: 234
aattctaata cgactcacta tagggagaag ggtctttgct tttcaactgg a        51

<210> SEQ ID NO 235
<211> LENGTH: 42
<212> TYPE: DNA
<213> ORGANISM: Artificial sequence
<220> FEATURE:
<223> OTHER INFORMATION: /note="HPV NASBA Primer"

<400> SEQUENCE: 235
gatgcaaggt cgcatatgag tcagaggagg aggaagatac ta                 42

<210> SEQ ID NO 236
<211> LENGTH: 51
<212> TYPE: DNA
<213> ORGANISM: Artificial sequence
<220> FEATURE:
<223> OTHER INFORMATION: /note="HPV NASBA Primer"

<400> SEQUENCE: 236
aattctaata cgactcacta tagggagaag ggattatgct ctctgtgaac a        51

<210> SEQ ID NO 237
<211> LENGTH: 40
<212> TYPE: DNA
<213> ORGANISM: Artificial sequence
<220> FEATURE:
<223> OTHER INFORMATION: /note="HPV NASBA Primer"

<400> SEQUENCE: 237
gatgcaaggt cgcatatgag cccgaggcaa ctgacctata                    40

<210> SEQ ID NO 238
<211> LENGTH: 51
<212> TYPE: DNA
```

```
<213> ORGANISM: Artificial sequence
<220> FEATURE:
<223> OTHER INFORMATION: /note="HPV NASBA Primer"

<400> SEQUENCE: 238
aattctaata cgactcacta tagggagaag ggtcaatgtg tgtgctctgt a        51

<210> SEQ ID NO 239
<211> LENGTH: 42
<212> TYPE: DNA
<213> ORGANISM: Artificial sequence
<220> FEATURE:
<223> OTHER INFORMATION: /note="HPV NASBA Primer"

<400> SEQUENCE: 239
gatgcaaggt cgcatatgag ttgtgtgagg tgctggaaga at                  42

<210> SEQ ID NO 240
<211> LENGTH: 49
<212> TYPE: DNA
<213> ORGANISM: Artificial sequence
<220> FEATURE:
<223> OTHER INFORMATION: /note="HPV NASBA Primer"

<400> SEQUENCE: 240
aattctaata cgactcacta tagggagaag gccctctctt ctaatgttt           49

<210> SEQ ID NO 241
<211> LENGTH: 40
<212> TYPE: DNA
<213> ORGANISM: Artificial sequence
<220> FEATURE:
<223> OTHER INFORMATION: /note="HPV NASBA Primer"

<400> SEQUENCE: 241
gatgcaaggt cgcatatgag gtgcctacgc ttttatcta                      40

<210> SEQ ID NO 242
<211> LENGTH: 53
<212> TYPE: DNA
<213> ORGANISM: Artificial sequence
<220> FEATURE:
<223> OTHER INFORMATION: /note="HPV NASBA Primer"

<400> SEQUENCE: 242
aattctaata cgactcacta tagggagaag gggggtctcc aacactctga aca      53

<210> SEQ ID NO 243
<211> LENGTH: 38
<212> TYPE: DNA
<213> ORGANISM: Artificial sequence
<220> FEATURE:
<223> OTHER INFORMATION: /note="HPV NASBA Primer"

<400> SEQUENCE: 243
gatgcaaggt cgcatatgag tcaggcgttg gagacatc                       38

<210> SEQ ID NO 244
<211> LENGTH: 49
<212> TYPE: DNA
<213> ORGANISM: Artificial sequence
<220> FEATURE:
<223> OTHER INFORMATION: /note="HPV NASBA Primer"

<400> SEQUENCE: 244
aattctaata cgactcacta tagggagaag gagcaatcgt aagcacact           49
```

<210> SEQ ID NO 245
<211> LENGTH: 38
<212> TYPE: DNA
<213> ORGANISM: Artificial sequence
<220> FEATURE:
<223> OTHER INFORMATION: /note="HPV NASBA Primer"

<400> SEQUENCE: 245
gatgcaaggt cgcatatgag tctgtgcatg aaatcgaa              38

<210> SEQ ID NO 246
<211> LENGTH: 49
<212> TYPE: DNA
<213> ORGANISM: Artificial sequence
<220> FEATURE:
<223> OTHER INFORMATION: /note="HPV NASBA Primer"

<400> SEQUENCE: 246
aattctaata cgactcacta tagggagaag gagcacactt tacatactg              49

<210> SEQ ID NO 247
<211> LENGTH: 38
<212> TYPE: DNA
<213> ORGANISM: Artificial sequence
<220> FEATURE:
<223> OTHER INFORMATION: /note="HPV NASBA Primer"

<400> SEQUENCE: 247
gatgcaaggt cgcatatgag tacactgctg gacaacat              38

<210> SEQ ID NO 248
<211> LENGTH: 49
<212> TYPE: DNA
<213> ORGANISM: Artificial sequence
<220> FEATURE:
<223> OTHER INFORMATION: /note="HPV NASBA Primer"

<400> SEQUENCE: 248
aattctaata cgactcacta tagggagaag gtcatcttct gagctgtct              49

<210> SEQ ID NO 249
<211> LENGTH: 41
<212> TYPE: DNA
<213> ORGANISM: Artificial sequence
<220> FEATURE:
<223> OTHER INFORMATION: /note="HPV NASBA Primer"

<400> SEQUENCE: 249
gatgcaaggt cgcatatgag tacactgctg gacaacatgc a              41

<210> SEQ ID NO 250
<211> LENGTH: 54
<212> TYPE: DNA
<213> ORGANISM: Artificial sequence
<220> FEATURE:
<223> OTHER INFORMATION: /note="HPV NASBA Primer"

<400> SEQUENCE: 250
aattctaata cgactcacta tagggagaag ggtcacatcc acagcaacag gtca              54

<210> SEQ ID NO 251
<211> LENGTH: 42
<212> TYPE: DNA
<213> ORGANISM: Artificial sequence
<220> FEATURE:
<223> OTHER INFORMATION: /note="HPV NASBA Primer"

```
<400> SEQUENCE: 251
gatgcaaggt cgcatatgag tgacctgttg ctgtggatgt ga                    42

<210> SEQ ID NO 252
<211> LENGTH: 50
<212> TYPE: DNA
<213> ORGANISM: Artificial sequence
<220> FEATURE:
<223> OTHER INFORMATION: /note="HPV NASBA Primer"

<400> SEQUENCE: 252
aattctaata cgactcacta tagggagaag gtacctgaat cgtccgccat            50

<210> SEQ ID NO 253
<211> LENGTH: 39
<212> TYPE: DNA
<213> ORGANISM: Artificial sequence
<220> FEATURE:
<223> OTHER INFORMATION: /note="HPV NASBA Primer"

<400> SEQUENCE: 253
gatgcaaggt cgcatatgag catgccataa atgtataga                        39

<210> SEQ ID NO 254
<211> LENGTH: 51
<212> TYPE: DNA
<213> ORGANISM: Artificial sequence
<220> FEATURE:
<223> OTHER INFORMATION: /note="HPV NASBA Primer"

<400> SEQUENCE: 254
aattctaata cgactcacta tagggagaag gcaccgcagg caccttatta a          51

<210> SEQ ID NO 255
<211> LENGTH: 41
<212> TYPE: DNA
<213> ORGANISM: Artificial sequence
<220> FEATURE:
<223> OTHER INFORMATION: /note="HPV NASBA Primer"

<400> SEQUENCE: 255
gatgcaaggt cgcatatgag gcagacgacc actacagcaa a                     41

<210> SEQ ID NO 256
<211> LENGTH: 50
<212> TYPE: DNA
<213> ORGANISM: Artificial sequence
<220> FEATURE:
<223> OTHER INFORMATION: /note="HPV NASBA Primer"

<400> SEQUENCE: 256
aattctaata cgactcacta tagggagaag gacaccgagt ccgagtaata            50

<210> SEQ ID NO 257
<211> LENGTH: 39
<212> TYPE: DNA
<213> ORGANISM: Artificial sequence
<220> FEATURE:
<223> OTHER INFORMATION: /note="HPV NASBA Primer"

<400> SEQUENCE: 257
gatgcaaggt cgcatatgag tattactcgg actcggtgt                        39

<210> SEQ ID NO 258
<211> LENGTH: 52
<212> TYPE: DNA
```

```
<213> ORGANISM: Artificial sequence
<220> FEATURE:
<223> OTHER INFORMATION: /note="HPV NASBA Primer"

<400> SEQUENCE: 258
aattctaata cgactcacta tagggagaag gcttgggttt ctcttcgtgt ta        52

<210> SEQ ID NO 259
<211> LENGTH: 40
<212> TYPE: DNA
<213> ORGANISM: Artificial sequence
<220> FEATURE:
<223> OTHER INFORMATION: /note="HPV NASBA Primer"

<400> SEQUENCE: 259
gatgcaaggt cgcatatgag gaaatagatg aacccgacca                      40

<210> SEQ ID NO 260
<211> LENGTH: 51
<212> TYPE: DNA
<213> ORGANISM: Artificial sequence
<220> FEATURE:
<223> OTHER INFORMATION: /note="HPV NASBA Primer"

<400> SEQUENCE: 260
aattctaata cgactcacta tagggagaag ggcacaccac ggacacacaa a         51

<210> SEQ ID NO 261
<211> LENGTH: 41
<212> TYPE: DNA
<213> ORGANISM: Artificial sequence
<220> FEATURE:
<223> OTHER INFORMATION: /note="HPV NASBA Primer"

<400> SEQUENCE: 261
gatgcaaggt cgcatatgag aaccattgaa cccagcagaa a                    41

<210> SEQ ID NO 262
<211> LENGTH: 53
<212> TYPE: DNA
<213> ORGANISM: Artificial sequence
<220> FEATURE:
<223> OTHER INFORMATION: /note="HPV NASBA Primer"

<400> SEQUENCE: 262
aattctaata cgactcacta tagggagaag gtctttcttg ccgtgcctgg tca       53

<210> SEQ ID NO 263
<211> LENGTH: 41
<212> TYPE: DNA
<213> ORGANISM: Artificial sequence
<220> FEATURE:
<223> OTHER INFORMATION: /note="HPV NASBA Primer"

<400> SEQUENCE: 263
gatgcaaggt cgcatatgag aaccattgaa cccagcagaa a                    41

<210> SEQ ID NO 264
<211> LENGTH: 53
<212> TYPE: DNA
<213> ORGANISM: Artificial sequence
<220> FEATURE:
<223> OTHER INFORMATION: /note="HPV NASBA Primer"

<400> SEQUENCE: 264
aattctaata cgactcacta tagggagaag gtctttcttg ccgtgcctgg tca       53
```

<210> SEQ ID NO 265
<211> LENGTH: 44
<212> TYPE: DNA
<213> ORGANISM: Artificial sequence
<220> FEATURE:
<223> OTHER INFORMATION: /note="HPV NASBA Primer"

<400> SEQUENCE: 265
gatgcaaggt cgcatatgag gaaaccattg aacccagcag aaaa           44

<210> SEQ ID NO 266
<211> LENGTH: 55
<212> TYPE: DNA
<213> ORGANISM: Artificial sequence
<220> FEATURE:
<223> OTHER INFORMATION: /note="HPV NASBA Primer"

<400> SEQUENCE: 266
aattctaata cgactcacta tagggagaag gttgctatac ttgtgtttcc ctacg    55

<210> SEQ ID NO 267
<211> LENGTH: 45
<212> TYPE: DNA
<213> ORGANISM: Artificial sequence
<220> FEATURE:
<223> OTHER INFORMATION: /note="HPV NASBA Primer"

<400> SEQUENCE: 267
gatgcaaggt cgcatatgag gttgacctgt tgtgttacca gcaat          45

<210> SEQ ID NO 268
<211> LENGTH: 55
<212> TYPE: DNA
<213> ORGANISM: Artificial sequence
<220> FEATURE:
<223> OTHER INFORMATION: /note="HPV NASBA Primer"

<400> SEQUENCE: 268
aattctaata cgactcacta tagggagaag gcaccacgga cacacaaagg acaag    55

<210> SEQ ID NO 269
<211> LENGTH: 42
<212> TYPE: DNA
<213> ORGANISM: Artificial sequence
<220> FEATURE:
<223> OTHER INFORMATION: /note="HPV NASBA Primer"

<400> SEQUENCE: 269
gatgcaaggt cgcatatgag ctgttgacct gttgtgttac ga             42

<210> SEQ ID NO 270
<211> LENGTH: 53
<212> TYPE: DNA
<213> ORGANISM: Artificial sequence
<220> FEATURE:
<223> OTHER INFORMATION: /note="HPV NASBA Primer"

<400> SEQUENCE: 270
aattctaata cgactcacta tagggagaag gccacggaca cacaaaggac aag      53

<210> SEQ ID NO 271
<211> LENGTH: 40
<212> TYPE: DNA
<213> ORGANISM: Artificial sequence
<220> FEATURE:
<223> OTHER INFORMATION: /note="HPV NASBA Primer"

```
<400> SEQUENCE: 271
gatgcaaggt cgcatatgag gttgacctgt tgtgttacga                            40

<210> SEQ ID NO 272
<211> LENGTH: 51
<212> TYPE: DNA
<213> ORGANISM: Artificial sequence
<220> FEATURE:
<223> OTHER INFORMATION: /note="HPV NASBA Primer"

<400> SEQUENCE: 272
aattctaata cgactcacta tagggagaag gacggacaca caaaggacaa g              51

<210> SEQ ID NO 273
<211> LENGTH: 40
<212> TYPE: DNA
<213> ORGANISM: Artificial sequence
<220> FEATURE:
<223> OTHER INFORMATION: /note="HPV NASBA Primer"

<400> SEQUENCE: 273
gatgcaaggt cgcatatgag ggaggaggat gaagtagata                            40

<210> SEQ ID NO 274
<211> LENGTH: 51
<212> TYPE: DNA
<213> ORGANISM: Artificial sequence
<220> FEATURE:
<223> OTHER INFORMATION: /note="HPV NASBA Primer"

<400> SEQUENCE: 274
aattctaata cgactcacta tagggagaag ggcccattaa catctgctgt a              51

<210> SEQ ID NO 275
<211> LENGTH: 43
<212> TYPE: DNA
<213> ORGANISM: Artificial sequence
<220> FEATURE:
<223> OTHER INFORMATION: /note="HPV NASBA Primer"

<400> SEQUENCE: 275
gatgcaaggt cgcatatgag agaggaggag gatgaagtag ata                       43

<210> SEQ ID NO 276
<211> LENGTH: 51
<212> TYPE: DNA
<213> ORGANISM: Artificial sequence
<220> FEATURE:
<223> OTHER INFORMATION: /note="HPV NASBA Primer"

<400> SEQUENCE: 276
aattctaata cgactcacta tagggagaag gacgggcaaa ccaggcttag t              51

<210> SEQ ID NO 277
<211> LENGTH: 44
<212> TYPE: DNA
<213> ORGANISM: Artificial sequence
<220> FEATURE:
<223> OTHER INFORMATION: /note="HPV NASBA Primer"

<400> SEQUENCE: 277
gatgcaaggt cgcatatgag ttggggtgct ggagacaaac atct                      44

<210> SEQ ID NO 278
<211> LENGTH: 55
<212> TYPE: DNA
```

```
<213> ORGANISM: Artificial sequence
<220> FEATURE:
<223> OTHER INFORMATION: /note="HPV NASBA Primer"

<400> SEQUENCE: 278
aattctaata cgactcacta tagggagaag gttcatcctc atcctcatcc tctga          55

<210> SEQ ID NO 279
<211> LENGTH: 42
<212> TYPE: DNA
<213> ORGANISM: Artificial sequence
<220> FEATURE:
<223> OTHER INFORMATION: /note="HPV NASBA Primer"

<400> SEQUENCE: 279
gatgcaaggt cgcatatgag tggggtgctg gagacaaaca tc                       42

<210> SEQ ID NO 280
<211> LENGTH: 53
<212> TYPE: DNA
<213> ORGANISM: Artificial sequence
<220> FEATURE:
<223> OTHER INFORMATION: /note="HPV NASBA Primer"

<400> SEQUENCE: 280
aattctaata cgactcacta tagggagaag gcatcctcat cctcatcctc tga            53

<210> SEQ ID NO 281
<211> LENGTH: 42
<212> TYPE: DNA
<213> ORGANISM: Artificial sequence
<220> FEATURE:
<223> OTHER INFORMATION: /note="HPV NASBA Primer"

<400> SEQUENCE: 281
gatgcaaggt cgcatatgag ttggggtgct ggagacaaac at                       42

<210> SEQ ID NO 282
<211> LENGTH: 53
<212> TYPE: DNA
<213> ORGANISM: Artificial sequence
<220> FEATURE:
<223> OTHER INFORMATION: /note="HPV NASBA Primer"

<400> SEQUENCE: 282
aattctaata cgactcacta tagggagaag gccacaaact tacactcaca aca            53

<210> SEQ ID NO 283
<211> LENGTH: 40
<212> TYPE: DNA
<213> ORGANISM: Artificial sequence
<220> FEATURE:
<223> OTHER INFORMATION: /note="HPV NASBA Primer"

<400> SEQUENCE: 283
gatgcaaggt cgcatatgag gattttcctt atgcagtgtg                          40

<210> SEQ ID NO 284
<211> LENGTH: 51
<212> TYPE: DNA
<213> ORGANISM: Artificial sequence
<220> FEATURE:
<223> OTHER INFORMATION: /note="HPV NASBA Primer"

<400> SEQUENCE: 284
aattctaata cgactcacta tagggagaag ggacatctgt agcaccttat t              51
```

```
<210> SEQ ID NO 285
<211> LENGTH: 34
<212> TYPE: DNA
<213> ORGANISM: Artificial sequence
<220> FEATURE:
<223> OTHER INFORMATION: /note="HPV molecular beacon probe"

<400> SEQUENCE: 285
cgcatgcaac tgayctmyac tgttatgaca tgcg                                  34

<210> SEQ ID NO 286
<211> LENGTH: 34
<212> TYPE: DNA
<213> ORGANISM: Artificial sequence
<220> FEATURE:
<223> OTHER INFORMATION: /note="HPV molecular beacon probe"

<400> SEQUENCE: 286
ccgtcgcaac tgayctmyac tgttatgacg acgg                                  34

<210> SEQ ID NO 287
<211> LENGTH: 34
<212> TYPE: DNA
<213> ORGANISM: Artificial sequence
<220> FEATURE:
<223> OTHER INFORMATION: /note="HPV molecular beacon probe"

<400> SEQUENCE: 287
ccaccccaac tgayctmyac tgttatgagg gtgg                                  34

<210> SEQ ID NO 288
<211> LENGTH: 34
<212> TYPE: DNA
<213> ORGANISM: Artificial sequence
<220> FEATURE:
<223> OTHER INFORMATION: /note="HPV molecular beacon probe"

<400> SEQUENCE: 288
cgatcgcaac tgayctmyac tgttatgacg atcg                                  34

<210> SEQ ID NO 289
<211> LENGTH: 36
<212> TYPE: DNA
<213> ORGANISM: Artificial sequence
<220> FEATURE:
<223> OTHER INFORMATION: /note="HPV molecular beacon probe"

<400> SEQUENCE: 289
ccaagcgaam caactgacct aywctgctat gcttgg                                36

<210> SEQ ID NO 290
<211> LENGTH: 38
<212> TYPE: DNA
<213> ORGANISM: Artificial sequence
<220> FEATURE:
<223> OTHER INFORMATION: /note="HPV molecular beacon probe"

<400> SEQUENCE: 290
ccaagccgaa mcaactgacc taywctgcta tggcttgg                              38

<210> SEQ ID NO 291
<211> LENGTH: 38
<212> TYPE: DNA
<213> ORGANISM: Artificial sequence
<220> FEATURE:
<223> OTHER INFORMATION: /note="HPV molecular beacon probe"
```

```
<400> SEQUENCE: 291
ccaagcggaa mcaactgacc taywctgcta tcgcttgg                              38

<210> SEQ ID NO 292
<211> LENGTH: 36
<212> TYPE: DNA
<213> ORGANISM: Artificial sequence
<220> FEATURE:
<223> OTHER INFORMATION: /note="HPV molecular beacon probe"

<400> SEQUENCE: 292
ccagcggaam caactgacct aywctgctat cgctgg                                36

<210> SEQ ID NO 293
<211> LENGTH: 36
<212> TYPE: DNA
<213> ORGANISM: Artificial sequence
<220> FEATURE:
<223> OTHER INFORMATION: /note="HPV molecular beacon probe"

<400> SEQUENCE: 293
cgatcggaam caactgacct aywctgctat cgatcg                                36

<210> SEQ ID NO 294
<211> LENGTH: 30
<212> TYPE: DNA
<213> ORGANISM: Artificial sequence
<220> FEATURE:
<223> OTHER INFORMATION: /note="HPV molecular beacon probe"

<400> SEQUENCE: 294
ccaagcaaga cattattcag actcgcttgg                                       30

<210> SEQ ID NO 295
<211> LENGTH: 30
<212> TYPE: DNA
<213> ORGANISM: Artificial sequence
<220> FEATURE:
<223> OTHER INFORMATION: /note="HPV molecular beacon probe"

<400> SEQUENCE: 295
cgcatgaaga cattattcag actccatgcg                                       30

<210> SEQ ID NO 296
<211> LENGTH: 30
<212> TYPE: DNA
<213> ORGANISM: Artificial sequence
<220> FEATURE:
<223> OTHER INFORMATION: /note="HPV molecular beacon probe"

<400> SEQUENCE: 296
cccagcaaga cattattcag actcgctggg                                       30

<210> SEQ ID NO 297
<211> LENGTH: 30
<212> TYPE: DNA
<213> ORGANISM: Artificial sequence
<220> FEATURE:
<223> OTHER INFORMATION: /note="HPV molecular beacon probe"

<400> SEQUENCE: 297
cgatcgaaga cattattcag actccgatcg                                       30

<210> SEQ ID NO 298
<211> LENGTH: 40
<212> TYPE: DNA
```

<213> ORGANISM: Artificial sequence
<220> FEATURE:
<223> OTHER INFORMATION: /note="HPV NASBA Primer"

<400> SEQUENCE: 298
gatgcaaggt cgcatatgag aatggcattt gttggggtaa                40

<210> SEQ ID NO 299
<211> LENGTH: 50
<212> TYPE: DNA
<213> ORGANISM: Artificial sequence
<220> FEATURE:
<223> OTHER INFORMATION: /note="HPV NASBA Primer"

<400> SEQUENCE: 299
aattctaata cgactcacta tagggagaag gtcatattcc tccccatgtc        50

<210> SEQ ID NO 300
<211> LENGTH: 40
<212> TYPE: DNA
<213> ORGANISM: Artificial sequence
<220> FEATURE:
<223> OTHER INFORMATION: /note="HPV NASBA Primer"

<400> SEQUENCE: 300
gatgcaaggt cgcatatgag aatggcattt gttggsrhaa                40

<210> SEQ ID NO 301
<211> LENGTH: 50
<212> TYPE: DNA
<213> ORGANISM: Artificial sequence
<220> FEATURE:
<223> OTHER INFORMATION: /note="HPV NASBA Primer"

<400> SEQUENCE: 301
aattctaata cgactcacta tagggagaag gtcatattcc tcmmcatgdc        50

<210> SEQ ID NO 302
<211> LENGTH: 40
<212> TYPE: DNA
<213> ORGANISM: Artificial sequence
<220> FEATURE:
<223> OTHER INFORMATION: /note="HPV NASBA Primer"
<220> FEATURE:
<221> NAME/KEY: misc_feature
<222> LOCATION: (37)..(37)
<223> OTHER INFORMATION: "n" represents inosine
<220> FEATURE:
<221> NAME/KEY: misc_feature
<222> LOCATION: (38)..(38)
<223> OTHER INFORMATION: "n" represents inosine

<400> SEQUENCE: 302
gatgcaaggt cgcatatgag aatggcattt gttggsnnaa                40

<210> SEQ ID NO 303
<211> LENGTH: 40
<212> TYPE: DNA
<213> ORGANISM: Artificial sequence
<220> FEATURE:
<223> OTHER INFORMATION: /note="HPV NASBA Primer"
<220> FEATURE:
<221> NAME/KEY: misc_feature
<222> LOCATION: (36)..(36)
<223> OTHER INFORMATION: "n" represents inosine
<220> FEATURE:
<221> NAME/KEY: misc_feature
<222> LOCATION: (37)..(37)
<223> OTHER INFORMATION: "n" represents inosine

<400> SEQUENCE: 303
gatgcaaggt cgcatatgag aatggcattt gttggnnhaa                            40

<210> SEQ ID NO 304
<211> LENGTH: 40
<212> TYPE: DNA
<213> ORGANISM: Artificial sequence
<220> FEATURE:
<223> OTHER INFORMATION: /note="HPV NASBA Primer"
<220> FEATURE:
<221> NAME/KEY: misc_feature
<222> LOCATION: (36)..(36)
<223> OTHER INFORMATION: "n" represents inosine
<220> FEATURE:
<221> NAME/KEY: misc_feature
<222> LOCATION: (38)..(38)
<223> OTHER INFORMATION: "n" represents inosine

<400> SEQUENCE: 304
gatgcaaggt cgcatatgag aatggcattt gttggnrnaa                            40

<210> SEQ ID NO 305
<211> LENGTH: 40
<212> TYPE: DNA
<213> ORGANISM: Artificial sequence
<220> FEATURE:
<223> OTHER INFORMATION: /note="HPV NASBA Primer"

<400> SEQUENCE: 305
gatgcaaggt cgcatatgag aatggcattt gttggggtaa                            40

<210> SEQ ID NO 306
<211> LENGTH: 40
<212> TYPE: DNA
<213> ORGANISM: Artificial sequence
<220> FEATURE:
<223> OTHER INFORMATION: /note="HPV NASBA Primer"

<400> SEQUENCE: 306
gatgcaaggt cgcatatgag aatggcattt gttggggaaa                            40

<210> SEQ ID NO 307
<211> LENGTH: 40
<212> TYPE: DNA
<213> ORGANISM: Artificial sequence
<220> FEATURE:
<223> OTHER INFORMATION: /note="HPV NASBA Primer"

<400> SEQUENCE: 307
gatgcaaggt cgcatatgag aatggcattt gttggcataa                            40

<210> SEQ ID NO 308
<211> LENGTH: 40
<212> TYPE: DNA
<213> ORGANISM: Artificial sequence
<220> FEATURE:
<223> OTHER INFORMATION: /note="HPV NASBA Primer"

<400> SEQUENCE: 308
gatgcaaggt cgcatatgag aatggcattt gttggggcaa                            40

<210> SEQ ID NO 309
<211> LENGTH: 40
<212> TYPE: DNA
<213> ORGANISM: Artificial sequence
<220> FEATURE:
<223> OTHER INFORMATION: /note="HPV NASBA Primer"

<400> SEQUENCE: 309
gatgcaaggt cgcatatgag aatggcattt gttggcacaa        40

<210> SEQ ID NO 310
<211> LENGTH: 50
<212> TYPE: DNA
<213> ORGANISM: Artificial sequence
<220> FEATURE:
<223> OTHER INFORMATION: /note="HPV NASBA Primer"
<220> FEATURE:
<221> NAME/KEY: misc_feature
<222> LOCATION: (44)..(44)
<223> OTHER INFORMATION: "n" represents inosine
<220> FEATURE:
<221> NAME/KEY: misc_feature
<222> LOCATION: (49)..(49)
<223> OTHER INFORMATION: "n" represents inosine

<400> SEQUENCE: 310
aattctaata cgactcacta tagggagaag gtcatattcc tcmncatgnc        50

<210> SEQ ID NO 311
<211> LENGTH: 50
<212> TYPE: DNA
<213> ORGANISM: Artificial sequence
<220> FEATURE:
<223> OTHER INFORMATION: /note="HPV NASBA Primer"
<220> FEATURE:
<221> NAME/KEY: misc_feature
<222> LOCATION: (49)..(49)
<223> OTHER INFORMATION: "n" represents inosine

<400> SEQUENCE: 311
aattctaata cgactcacta tagggagaag gtcatattcc tcaacatgnc        50

<210> SEQ ID NO 312
<211> LENGTH: 50
<212> TYPE: DNA
<213> ORGANISM: Artificial sequence
<220> FEATURE:
<223> OTHER INFORMATION: /note="HPV NASBA Primer"
<220> FEATURE:
<221> NAME/KEY: misc_feature
<222> LOCATION: (43)..(43)
<223> OTHER INFORMATION: "n" represents inosine
<220> FEATURE:
<221> NAME/KEY: misc_feature
<222> LOCATION: (44)..(44)
<223> OTHER INFORMATION: "n" represents inosine

<400> SEQUENCE: 312
aattctaata cgactcacta tagggagaag gtcatattcc tcnncatgtc        50

<210> SEQ ID NO 313
<211> LENGTH: 50
<212> TYPE: DNA
<213> ORGANISM: Artificial sequence
<220> FEATURE:
<223> OTHER INFORMATION: /note="HPV NASBA Primer"
<220> FEATURE:
<221> NAME/KEY: misc_feature
<222> LOCATION: (43)..(43)
<223> OTHER INFORMATION: "n" represents inosine
<220> FEATURE:
<221> NAME/KEY: misc_feature
<222> LOCATION: (44)..(44)
<223> OTHER INFORMATION: "n" represents inosine

<400> SEQUENCE: 313
aattctaata cgactcacta tagggagaag gtcatattcc tcnncatggc        50

```
<210> SEQ ID NO 314
<211> LENGTH: 50
<212> TYPE: DNA
<213> ORGANISM: Artificial sequence
<220> FEATURE:
<223> OTHER INFORMATION: /note="HPV NASBA Primer"
<220> FEATURE:
<221> NAME/KEY: misc_feature
<222> LOCATION: (43)..(43)
<223> OTHER INFORMATION: "n" represents inosine
<220> FEATURE:
<221> NAME/KEY: misc_feature
<222> LOCATION: (44)..(44)
<223> OTHER INFORMATION: "n" represents inosine

<400> SEQUENCE: 314
aattctaata cgactcacta tagggagaag gtcatattcc tcnncatgac          50

<210> SEQ ID NO 315
<211> LENGTH: 50
<212> TYPE: DNA
<213> ORGANISM: Artificial sequence
<220> FEATURE:
<223> OTHER INFORMATION: /note="HPV NASBA Primer"
<220> FEATURE:
<221> NAME/KEY: misc_feature
<222> LOCATION: (43)..(43)
<223> OTHER INFORMATION: "n" represents inosine
<220> FEATURE:
<221> NAME/KEY: misc_feature
<222> LOCATION: (44)..(44)
<223> OTHER INFORMATION: "n" represents inosine

<400> SEQUENCE: 315
aattctaata cgactcacta tagggagaag gtcatattcc tcnncatgcc          50

<210> SEQ ID NO 316
<211> LENGTH: 18
<212> TYPE: DNA
<213> ORGANISM: Artificial sequence
<220> FEATURE:
<223> OTHER INFORMATION: primer

<400> SEQUENCE: 316
tacactgctg gacaacat                                              18

<210> SEQ ID NO 317
<211> LENGTH: 18
<212> TYPE: DNA
<213> ORGANISM: Artificial sequence
<220> FEATURE:
<223> OTHER INFORMATION: primer

<400> SEQUENCE: 317
tcatcttctg agctgtct                                              18

<210> SEQ ID NO 318
<211> LENGTH: 21
<212> TYPE: DNA
<213> ORGANISM: Artificial sequence
<220> FEATURE:
<223> OTHER INFORMATION: primer

<400> SEQUENCE: 318
tcaaaagcca ctgtgtcctg a                                          21

<210> SEQ ID NO 319
<211> LENGTH: 21
<212> TYPE: DNA
```

```
<213> ORGANISM: Artificial sequence
<220> FEATURE:
<223> OTHER INFORMATION: primer

<400> SEQUENCE: 319
cgtgttcttg atgatctgca a                                              21

<210> SEQ ID NO 320
<211> LENGTH: 20
<212> TYPE: DNA
<213> ORGANISM: Artificial sequence
<220> FEATURE:
<223> OTHER INFORMATION: primer

<400> SEQUENCE: 320
ttccggttga ccttctatgt                                                20

<210> SEQ ID NO 321
<211> LENGTH: 20
<212> TYPE: DNA
<213> ORGANISM: Artificial sequence
<220> FEATURE:
<223> OTHER INFORMATION: primer

<400> SEQUENCE: 321
ggtcgtctgc tgagctttct                                                20

<210> SEQ ID NO 322
<211> LENGTH: 23
<212> TYPE: DNA
<213> ORGANISM: Artificial sequence
<220> FEATURE:
<223> OTHER INFORMATION: primer

<400> SEQUENCE: 322
ctacagtaag cattgtgcta tgc                                            23

<210> SEQ ID NO 323
<211> LENGTH: 26
<212> TYPE: DNA
<213> ORGANISM: Artificial sequence
<220> FEATURE:
<223> OTHER INFORMATION: primer

<400> SEQUENCE: 323
acgtaatgga gaggttgcaa taaccc                                         26

<210> SEQ ID NO 324
<211> LENGTH: 21
<212> TYPE: DNA
<213> ORGANISM: Artificial sequence
<220> FEATURE:
<223> OTHER INFORMATION: primer

<400> SEQUENCE: 324
aacgccatga gaggacacaa g                                              21

<210> SEQ ID NO 325
<211> LENGTH: 21
<212> TYPE: DNA
<213> ORGANISM: Artificial sequence
<220> FEATURE:
<223> OTHER INFORMATION: primer

<400> SEQUENCE: 325
acacataaac gaactgtggt g                                              21
```

```
<210> SEQ ID NO 326
<211> LENGTH: 20
<212> TYPE: DNA
<213> ORGANISM: Artificial sequence
<220> FEATURE:
<223> OTHER INFORMATION: primer

<400> SEQUENCE: 326
cccgaggcaa ctgacctata                                              20

<210> SEQ ID NO 327
<211> LENGTH: 20
<212> TYPE: DNA
<213> ORGANISM: Artificial sequence
<220> FEATURE:
<223> OTHER INFORMATION: primer

<400> SEQUENCE: 327
ggggcacact attccaaatg                                              20

<210> SEQ ID NO 328
<211> LENGTH: 21
<212> TYPE: DNA
<213> ORGANISM: Artificial sequence
<220> FEATURE:
<223> OTHER INFORMATION: primer

<400> SEQUENCE: 328
gcagacgacc actacagcaa a                                            21

<210> SEQ ID NO 329
<211> LENGTH: 19
<212> TYPE: DNA
<213> ORGANISM: Artificial sequence
<220> FEATURE:
<223> OTHER INFORMATION: primer

<400> SEQUENCE: 329
acaccgagtc cgagtaata                                               19

<210> SEQ ID NO 330
<211> LENGTH: 24
<212> TYPE: DNA
<213> ORGANISM: Artificial sequence
<220> FEATURE:
<223> OTHER INFORMATION: primer

<400> SEQUENCE: 330
gaaaccattg aacccagcag aaaa                                         24

<210> SEQ ID NO 331
<211> LENGTH: 24
<212> TYPE: DNA
<213> ORGANISM: Artificial sequence
<220> FEATURE:
<223> OTHER INFORMATION: primer

<400> SEQUENCE: 331
ttgctatact tgtgtttccc tacg                                         24

<210> SEQ ID NO 332
<211> LENGTH: 20
<212> TYPE: DNA
<213> ORGANISM: Artificial sequence
<220> FEATURE:
<223> OTHER INFORMATION: primer
```

<400> SEQUENCE: 332
ggaggaggat gaagtagata                                              20

<210> SEQ ID NO 333
<211> LENGTH: 20
<212> TYPE: DNA
<213> ORGANISM: Artificial sequence
<220> FEATURE:
<223> OTHER INFORMATION: primer

<400> SEQUENCE: 333
gcccattaac atctgctgta                                              20

<210> SEQ ID NO 334
<211> LENGTH: 20
<212> TYPE: DNA
<213> ORGANISM: Artificial sequence
<220> FEATURE:
<223> OTHER INFORMATION: primer

<400> SEQUENCE: 334
gtgcctacgc tttttatcta                                              20

<210> SEQ ID NO 335
<211> LENGTH: 22
<212> TYPE: DNA
<213> ORGANISM: Artificial sequence
<220> FEATURE:
<223> OTHER INFORMATION: primer

<400> SEQUENCE: 335
ggggtctcca acactctgaa ca                                           22

<210> SEQ ID NO 336
<211> LENGTH: 18
<212> TYPE: DNA
<213> ORGANISM: Artificial sequence
<220> FEATURE:
<223> OTHER INFORMATION: primer

<400> SEQUENCE: 336
tcaggcgttg gagacatc                                                18

<210> SEQ ID NO 337
<211> LENGTH: 18
<212> TYPE: DNA
<213> ORGANISM: Artificial sequence
<220> FEATURE:
<223> OTHER INFORMATION: primer

<400> SEQUENCE: 337
agcaatcgta agcacact                                                18

<210> SEQ ID NO 338
<211> LENGTH: 23
<212> TYPE: DNA
<213> ORGANISM: Artificial sequence
<220> FEATURE:
<223> OTHER INFORMATION: primer

<400> SEQUENCE: 338
tttgttactg tggtagatac tac                                          23

<210> SEQ ID NO 339
<211> LENGTH: 25
<212> TYPE: DNA

```
<213> ORGANISM: Artificial sequence
<220> FEATURE:
<223> OTHER INFORMATION: primer

<400> SEQUENCE: 339
gaaaaataaa ctgtaaatca tattc                                          25

<210> SEQ ID NO 340
<211> LENGTH: 20
<212> TYPE: DNA
<213> ORGANISM: Artificial sequence
<220> FEATURE:
<223> OTHER INFORMATION: primer

<400> SEQUENCE: 340
acacaactgt gttcactagc                                                20

<210> SEQ ID NO 341
<211> LENGTH: 20
<212> TYPE: DNA
<213> ORGANISM: Artificial sequence
<220> FEATURE:
<223> OTHER INFORMATION: primer

<400> SEQUENCE: 341
gaaacccaag agtcttctct                                                20

<210> SEQ ID NO 342
<211> LENGTH: 32
<212> TYPE: DNA
<213> ORGANISM: Artificial sequence
<220> FEATURE:
<223> OTHER INFORMATION: /note="HPV molecular beacon probe"

<400> SEQUENCE: 342
cgatcggtac cgagggcagt gtaatacgat cg                                  32

<210> SEQ ID NO 343
<211> LENGTH: 32
<212> TYPE: DNA
<213> ORGANISM: Artificial sequence
<220> FEATURE:
<223> OTHER INFORMATION: /note="HPV molecular beacon probe"

<400> SEQUENCE: 343
cgatcggtgc ctacgctttt tatctacgat cg                                  32

<210> SEQ ID NO 344
<211> LENGTH: 34
<212> TYPE: DNA
<213> ORGANISM: Artificial sequence
<220> FEATURE:
<223> OTHER INFORMATION: /note="HPV molecular beacon probe"

<400> SEQUENCE: 344
ccgtcgttgc agcgatctga ggtatatgcg acgg                                34

<210> SEQ ID NO 345
<211> LENGTH: 36
<212> TYPE: DNA
<213> ORGANISM: Artificial sequence
<220> FEATURE:
<223> OTHER INFORMATION: /note="HPV molecular beacon probe"

<400> SEQUENCE: 345
cgatcgtggc agtggaaagc agtggagaca cgatcg                              36
```

```
<210> SEQ ID NO 346
<211> LENGTH: 21
<212> TYPE: DNA
<213> ORGANISM: Artificial sequence
<220> FEATURE:
<223> OTHER INFORMATION: primer

<400> SEQUENCE: 346
acacataaac gaactgtgtg t                                              21
```